US007462486B2

(12) United States Patent
Vandenbark

(10) Patent No.: US 7,462,486 B2
(45) Date of Patent: Dec. 9, 2008

(54) METHODS OF SELECTING T CELL RECEPTOR V PEPTIDES FOR THERAPEUTIC USE

(75) Inventor: Arthur A. Vandenbark, Portland, OR (US)

(73) Assignees: Oregon Health & Science University, Portland, OR (US); The United States of America as represented by the Department of Veterans Affairs, Washington, DC (US)

( * ) Notice: Subject to any disclaimer, the term of this patent is extended or adjusted under 35 U.S.C. 154(b) by 519 days.

(21) Appl. No.: 10/438,729

(22) Filed: May 14, 2003

(65) Prior Publication Data
US 2003/0190665 A1 Oct. 9, 2003

Related U.S. Application Data

(63) Continuation-in-part of application No. 09/853,830, filed on May 10, 2001, now abandoned.

(60) Provisional application No. 60/203,984, filed on May 12, 2000, provisional application No. 60/380,731, filed on May 14, 2002.

(51) Int. Cl.
C12N 5/00 (2006.01)
C12N 5/02 (2006.01)
A61K 38/00 (2006.01)
C07K 2/00 (2006.01)
C07K 4/00 (2006.01)
C07K 5/00 (2006.01)
C07K 7/00 (2006.01)
C07K 14/00 (2006.01)
C07K 16/00 (2006.01)
C07K 17/00 (2006.01)

(52) U.S. Cl. ..................... 435/375; 530/300
(58) Field of Classification Search ................ None
See application file for complete search history.

(56) References Cited

U.S. PATENT DOCUMENTS

| 5,194,425 | A | | 3/1993 | Sharma et al. |
| 5,223,426 | A | | 6/1993 | Skibbens et al. |
| 5,569,585 | A | * | 10/1996 | Goodwin et al. ............ 435/6 |
| 5,612,035 | A | | 3/1997 | Howell et al. |
| 5,614,192 | A | | 3/1997 | Vandenbark |
| 5,776,459 | A | | 7/1998 | Vandenbark |
| 5,837,246 | A | | 11/1998 | Howell et al. |
| 5,856,446 | A | | 1/1999 | Weiner et al. |
| 5,858,968 | A | | 1/1999 | Weiner et al. |
| 5,869,093 | A | | 2/1999 | Weiner et al. |
| 5,939,281 | A | | 8/1999 | Lehmann et al. |
| 5,939,400 | A | | 8/1999 | Steinman et al. |
| 6,019,971 | A | | 2/2000 | Weiner et al. |
| 6,039,947 | A | | 3/2000 | Weiner et al. |
| 6,045,796 | A | | 4/2000 | Sriram et al. |
| 6,090,387 | A | | 7/2000 | Howell et al. |
| 6,113,903 | A | | 9/2000 | Albertini et al. |
| 6,159,470 | A | | 12/2000 | Howell et al. |
| 6,197,926 | B1 | | 3/2001 | Gaur et al. |
| 6,207,645 | B1 | | 3/2001 | Howell et al. |
| 6,218,132 | B1 | | 4/2001 | Spack et al. |
| 6,221,352 | B1 | | 4/2001 | Howell et al. |
| 6,958,327 | B1 | | 10/2005 | Hillisch et al. |
| 2002/0183299 | A1 | | 12/2002 | Voskuhl |

FOREIGN PATENT DOCUMENTS

| EP | 0 159 739 A1 | 10/1985 |
| EP | 0957359 | 11/1999 |
| JP | 10175854 | 6/1998 |
| WO | WO 94/25063 | 11/1994 |
| WO | WO 99/58977 | 11/1999 |

OTHER PUBLICATIONS

Vandenbark et al., 2005, Current Drug Targets, vol. 4: 217-229.*
Thornton et al., 1998, J. Exp. Med. vol. 188: 287-296.*
Venken et al., 2006, J. Neur. Res. vol. 83: 1432-1446.*
Vandenbark et al., 2000, Crit. Rev. Immunology, vol. 20: 57-83.*
Vandenbark et al., 2001, J. Neur. Res. vol. 66: 171-176.*
Janeway and Travers, 1997, Immunobiology, pp. 7:26-7:27.*
Arden et al., "Human T-cell receptor variable gene segment families," *Immunogenetics* 42:455-500, 1995.
Brosterhaus et al., "Enrichment and detection of live antigen-specific CD4+ T cells based on cytokine secretion," *Eur. J. Immunol.* 29:4053-4059, 1999.
Choi et al., "Interaction of *Staphylococcus aureus* toxin 'superantigens' with human T cells," *Proc. Natl. Acad. Sci. USA* 86:8941-8945, 1989.
Chou et al., "Immunity to TCR peptides in multiple sclerosis," *J. Immunol.* 152:2520-2529, 1994.
Chou et al., "MHC-restriction, cytokine profile, and immunoregulatory effects of human T cells specific for TCR Vβ CDR2 peptides: comparison with myelin basic protein-specific T cells," *J. Neuroscience Res.* 45:838-851, 1996.
Cochlovius et al., "In vitro and in vivo induction of a Th cell response toward peptides of the melanoma-associated glycoprotein 100 protein selected by the Tepitope program," *J. Immunol.* 165:4731-4741, 2000.
Concannon et al., "Diversity and structure of human T-cell receptor β-chain variable region genes," *Proc. Natl. Acad. Sci. USA* 83:6598-6602, 1986.

(Continued)

*Primary Examiner*—G. R. Ewoldt
*Assistant Examiner*—Amy Juedes
(74) *Attorney, Agent, or Firm*—Klarquist Sparkman, LLP

(57) ABSTRACT

A method is disclosed to identify a T cell receptor (TCR) variable (V) peptide of use as a therapeutic agent in a subject. A method is also disclosed for monitoring the efficacy of a T Cell Receptor (TCR) V peptide for the treatment of a subject. In another embodiment, a method is disclosed for selecting a TCR V peptide of use in therapy for a subject having an autoimmune disease.

14 Claims, 11 Drawing Sheets

OTHER PUBLICATIONS

Czerkinsky et al., "Reverse ELISPOT assay for clonal analysis of cytokine production," *J. Immunol. Methods* 110:29-36, 1998.

Evavold et al., "Tickling the TCR: selective T-cell functions stimulated by altered peptide ligands," *Immunology Today* 14:602-609, 1993.

Fairchild, "Altered peptide ligands: prospects for immune intervention in autoimmune disease," *Eur. J. Immunogenet.* 24:155-167, 1997.

Genevee et al., "An experimentally validated panel of subfamily-specific oligonucleotide primer (Vα-w29/Vβ1-w24) for the study of human T cell receptor variable V gene segment usage by polymerase chain reaction," *Eur. J. Immunol.* 22:1261-1269, 1992.

Kay et al., "Altered T cell repertoire usage in CD4 and CD8 subsets of multiple myeloma patients, a study of the eastern cooperative oncology group (E9487)," *Leuk. Lymphoma* 33:127-133, 1999.

Kimura et al., "Sequences and repertoire of the human T cell receptor α and β chain variable region genes in thymocytes," *Eur. J. Immunol.* 17:375-383, 1987.

Mancia et al., "Characterization of the T-cell receptor V-β repertoire in Kawasaki disease," *Scand. J. Immunol.* 48:443-449, 1998.

Olsson et al., "Autoreactive T lymphocytes in multiple sclerosis determined by antigen-induced secretion of interferon-γ," *J. Clin. Invest.* 86:981-985, 1990.

Robinson, "The human T cell receptor β-chain gene complex contains at least 57 variable gene segments," *J. Immunol.* 146:4392-4397, 1991.

Savoie et al., "Use of Bonsai decision trees for the identification of potential MHC class I peptide epitope motifs," *Pac. Symp. Biocomput.* 1999:182-189, 1999.

Vandenbark et al., "Treatment of multiple sclerosis with T-cell receptor peptides: Results of a double-blind pilot trail," *Nature Med.* 2:1109-1115, 1996.

Acha-Orbea et al., "Limited Heterogeneity of T Cell Receptors from Lymphocytes Mediating Autoimmune Encephalomyelitis Allows Specific Immune Intervention," *Cell* 54:263-273, Jul. 15, 1988.

Gilmore et al., "Effect of Estradiol on Cytokine Secretion by Proteolipid Protein-Specific T Cell Clones Isolated from Multiple Sclerosis Patients and Normal Control Subjects," *J. Immunol.* 158:446-451, (1997).

\* cited by examiner

SEQUENCE LISTING

<160> NUMBER OF SEQ ID NOS: 181

<210> SEQ ID NO 1
<211> LENGTH: 21
<212> TYPE: PRT
<213> ORGANISM: Artificial sequence
<220> FEATURE:
<223> OTHER INFORMATION: synthetic

<400> SEQUENCE: 1

Tyr Pro Gly Gln His Leu Gln Leu Leu Leu Lys Tyr Phe Ser Gly Asp
1               5                   10                  15

Pro Leu Val Lys Gly
            20

```
<210> SEQ ID NO 2
<211> LENGTH: 21
<212> TYPE: PRT
<213> ORGANISM: Artificial sequence
<220> FEATURE:
<223> OTHER INFORMATION: synthetic

<400> SEQUENCE: 2

Tyr Pro Asn Gln Gly Leu Gln Leu Leu Leu Lys Tyr Thr Ser Ala Ala
1               5                   10                  15

Thr Leu Val Lys Gly
            20

<210> SEQ ID NO 3
<211> LENGTH: 21
<212> TYPE: PRT
<213> ORGANISM: Artificial sequence
<220> FEATURE:
<223> OTHER INFORMATION: synthetic

<400> SEQUENCE: 3

Tyr Pro Asn Gln Gly Leu Gln Leu Leu Leu Lys Tyr Thr Thr Gly Ala
1               5                   10                  15

Thr Leu Val Lys Gly
            20

<210> SEQ ID NO 4
<211> LENGTH: 21
<212> TYPE: PRT
<213> ORGANISM: Artificial sequence
<220> FEATURE:
<223> OTHER INFORMATION: synthetic

<400> SEQUENCE: 4

Tyr Pro Asn Gln Gly Leu Gln Leu Leu Leu Lys Tyr Thr Ser Ala Ala
1               5                   10                  15

Thr Leu Val Lys Gly
            20

<210> SEQ ID NO 5
<211> LENGTH: 21
<212> TYPE: PRT
<213> ORGANISM: Artificial sequence
<220> FEATURE:
<223> OTHER INFORMATION: synthetic

<400> SEQUENCE: 5

Tyr Pro Asn Gln Gly Leu Gln Leu Leu Leu Lys Tyr Leu Ser Gly Ser
1               5                   10                  15

Thr Leu Val Glu Ser
            20

<210> SEQ ID NO 6
<211> LENGTH: 21
<212> TYPE: PRT
<213> ORGANISM: Artificial sequence
<220> FEATURE:
<223> OTHER INFORMATION: synthetic

<400> SEQUENCE: 6

Tyr Pro Asn Gln Gly Leu Gln Leu Leu Leu Lys Tyr Leu Ser Gly Ser
1               5                   10                  15

Thr Leu Val Lys Gly
            20
```

```
<210> SEQ ID NO 7
<211> LENGTH: 21
<212> TYPE: PRT
<213> ORGANISM: Artificial sequence
<220> FEATURE:
<223> OTHER INFORMATION: synthetic

<400> SEQUENCE: 7

Ser Pro Gly Gln Gly Leu Gln Leu Leu Lys Tyr Phe Ser Gly Asp
1               5                   10                  15

Thr Leu Val Gln Gly
            20

<210> SEQ ID NO 8
<211> LENGTH: 21
<212> TYPE: PRT
<213> ORGANISM: Artificial sequence
<220> FEATURE:
<223> OTHER INFORMATION: synthetic

<400> SEQUENCE: 8

His Pro Asn Lys Gly Leu Gln Leu Leu Lys Tyr Thr Ser Ala Ala
1               5                   10                  15

Thr Leu Val Lys Gly
            20

<210> SEQ ID NO 9
<211> LENGTH: 21
<212> TYPE: PRT
<213> ORGANISM: Artificial sequence
<220> FEATURE:
<223> OTHER INFORMATION: synthetic

<400> SEQUENCE: 9

Tyr Ser Gly Lys Ser Pro Glu Leu Ile Met Phe Ile Tyr Ser Asn Gly
1               5                   10                  15

Asp Lys Glu Asp Gly
            20

<210> SEQ ID NO 10
<211> LENGTH: 21
<212> TYPE: PRT
<213> ORGANISM: Artificial sequence
<220> FEATURE:
<223> OTHER INFORMATION: synthetic

<400> SEQUENCE: 10

Tyr Ser Gly Lys Ser Pro Glu Leu Ile Met Ser Ile Tyr Ser Asn Gly
1               5                   10                  15

Asp Lys Glu Asp Gly
            20

<210> SEQ ID NO 11
<211> LENGTH: 21
<212> TYPE: PRT
<213> ORGANISM: Artificial sequence
<220> FEATURE:
<223> OTHER INFORMATION: synthetic

<400> SEQUENCE: 11

Tyr Ser Arg Lys Gly Pro Glu Leu Leu Met Tyr Thr Tyr Ser Ser Gly
1               5                   10                  15

Asn Lys Glu Asp Gly
```

```
<210> SEQ ID NO 12
<211> LENGTH: 21
<212> TYPE: PRT
<213> ORGANISM: Artificial sequence
<220> FEATURE:
<223> OTHER INFORMATION: synthetic

<400> SEQUENCE: 12

Tyr Ser Arg Ile Gly Pro Glu Leu Leu Met Tyr Thr Tyr Ser Ser Gly
1               5                   10                  15

Asn Lys Glu Asp Gly
            20

<210> SEQ ID NO 13
<211> LENGTH: 21
<212> TYPE: PRT
<213> ORGANISM: Artificial sequence
<220> FEATURE:
<223> OTHER INFORMATION: synthetic

<400> SEQUENCE: 13

Asp Cys Arg Lys Glu Pro Lys Leu Leu Met Ser Val Tyr Ser Ser Gly
1               5                   10                  15

Asn Glu Asp Gly Arg
            20

<210> SEQ ID NO 14
<211> LENGTH: 21
<212> TYPE: PRT
<213> ORGANISM: Artificial sequence
<220> FEATURE:
<223> OTHER INFORMATION: synthetic

<400> SEQUENCE: 14

Asn Ser Gly Arg Gly Leu Val His Leu Ile Leu Ile Arg Ser Asn Glu
1               5                   10                  15

Arg Glu Lys His Ser
            20

<210> SEQ ID NO 15
<211> LENGTH: 21
<212> TYPE: PRT
<213> ORGANISM: Artificial sequence
<220> FEATURE:
<223> OTHER INFORMATION: synthetic

<400> SEQUENCE: 15

Leu Pro Ser Gln Gly Pro Glu Tyr Val Ile His Gly Leu Thr Ser Asn
1               5                   10                  15

Val Asn Asn Arg Met
            20

<210> SEQ ID NO 16
<211> LENGTH: 21
<212> TYPE: PRT
<213> ORGANISM: Artificial sequence
<220> FEATURE:
<223> OTHER INFORMATION: synthetic

<400> SEQUENCE: 16

Ile His Ser Gln Gly Pro Gln Tyr Ile Ile His Gly Leu Lys Asn Asn
1               5                   10                  15
```

```
Glu Thr Asn Glu Met
            20

<210> SEQ ID NO 17
<211> LENGTH: 21
<212> TYPE: PRT
<213> ORGANISM: Artificial sequence
<220> FEATURE:
<223> OTHER INFORMATION: synthetic

<400> SEQUENCE: 17

Ile His Ser Gln Gly Pro Gln Asn Ile Ile His Gly Leu Lys Asn Asn
1               5                   10                  15

Glu Thr Asn Glu Met
            20

<210> SEQ ID NO 18
<211> LENGTH: 21
<212> TYPE: PRT
<213> ORGANISM: Artificial sequence
<220> FEATURE:
<223> OTHER INFORMATION: synthetic

<400> SEQUENCE: 18

Asp Pro Gly Arg Gly Pro Val Phe Leu Leu Ile Arg Glu Asn Glu
1               5                   10                  15

Lys Glu Lys Arg Lys
            20

<210> SEQ ID NO 19
<211> LENGTH: 21
<212> TYPE: PRT
<213> ORGANISM: Artificial sequence
<220> FEATURE:
<223> OTHER INFORMATION: synthetic

<400> SEQUENCE: 19

Ser Ser Gly Glu Met Ile Phe Leu Ile Tyr Gln Gly Ser Tyr Asp Gln
1               5                   10                  15

Gln Asn Ala Thr Glu
            20

<210> SEQ ID NO 20
<211> LENGTH: 21
<212> TYPE: PRT
<213> ORGANISM: Artificial sequence
<220> FEATURE:
<223> OTHER INFORMATION: synthetic

<400> SEQUENCE: 20

Ser Ser Gly Glu Met Ile Phe Leu Ile Tyr Gln Gly Ser Tyr Asp Glu
1               5                   10                  15

Gln Asn Ala Thr Glu
            20

<210> SEQ ID NO 21
<211> LENGTH: 21
<212> TYPE: PRT
<213> ORGANISM: Artificial sequence
<220> FEATURE:
<223> OTHER INFORMATION: synthetic

<400> SEQUENCE: 21

His Asp Gly Gly Ala Pro Thr Phe Leu Ser Tyr Asn Ala Leu Asp Gly
1               5                   10                  15
```

Leu Glu Glu Thr Gly
            20

<210> SEQ ID NO 22
<211> LENGTH: 21
<212> TYPE: PRT
<213> ORGANISM: Artificial sequence
<220> FEATURE:
<223> OTHER INFORMATION: synthetic

<400> SEQUENCE: 22

His Asp Gly Gly Ala Pro Thr Phe Leu Ser Tyr Asn Gly Leu Asp Gly
1               5                   10                  15

Leu Glu Glu Thr Gly
            20

<210> SEQ ID NO 23
<211> LENGTH: 21
<212> TYPE: PRT
<213> ORGANISM: Artificial sequence
<220> FEATURE:
<223> OTHER INFORMATION: synthetic

<400> SEQUENCE: 23

His Ala Gly Glu Ala Pro Thr Phe Leu Ser Tyr Asn Val Leu Asp Gly
1               5                   10                  15

Leu Glu Glu Lys Gly
            20

<210> SEQ ID NO 24
<211> LENGTH: 21
<212> TYPE: PRT
<213> ORGANISM: Artificial sequence
<220> FEATURE:
<223> OTHER INFORMATION: synthetic

<400> SEQUENCE: 24

Glu Leu Gly Lys Arg Pro Gln Leu Ile Ile Asp Ile Arg Ser Asn Val
1               5                   10                  15

Gly Glu Lys Lys Asp
            20

<210> SEQ ID NO 25
<211> LENGTH: 21
<212> TYPE: PRT
<213> ORGANISM: Artificial sequence
<220> FEATURE:
<223> OTHER INFORMATION: synthetic

<400> SEQUENCE: 25

Glu Leu Gly Lys Gly Pro Gln Leu Ile Ile Asp Ile Arg Ser Asn Val
1               5                   10                  15

Gly Glu Lys Lys Asp
            20

<210> SEQ ID NO 26
<211> LENGTH: 21
<212> TYPE: PRT
<213> ORGANISM: Artificial sequence
<220> FEATURE:
<223> OTHER INFORMATION: synthetic

<400> SEQUENCE: 26

Glu Ser Gly Lys Gly Pro Gln Phe Ile Ile Asp Ile Arg Ser Asn Met

Asp Lys Arg Gln Gly
        20

<210> SEQ ID NO 27
<211> LENGTH: 21
<212> TYPE: PRT
<213> ORGANISM: Artificial sequence
<220> FEATURE:
<223> OTHER INFORMATION: synthetic

<400> SEQUENCE: 27

Tyr Ser Arg Gln Arg Leu Gln Leu Leu Arg His Ile Ser Arg Glu
1               5                   10                  15

Ser Ile Lys Gly Phe
        20

<210> SEQ ID NO 28
<211> LENGTH: 21
<212> TYPE: PRT
<213> ORGANISM: Artificial sequence
<220> FEATURE:
<223> OTHER INFORMATION: synthetic

<400> SEQUENCE: 28

Glu Pro Gly Glu Gly Pro Val Leu Leu Val Thr Val Val Thr Gly Gly
1               5                   10                  15

Glu Val Lys Lys Leu
        20

<210> SEQ ID NO 29
<211> LENGTH: 21
<212> TYPE: PRT
<213> ORGANISM: Artificial sequence
<220> FEATURE:
<223> OTHER INFORMATION: synthetic

<400> SEQUENCE: 29

Phe Pro Gly Cys Ala Pro Arg Leu Leu Val Lys Gly Ser Lys Pro Ser
1               5                   10                  15

Gln Gln Gly Arg Tyr
        20

<210> SEQ ID NO 30
<211> LENGTH: 21
<212> TYPE: PRT
<213> ORGANISM: Artificial sequence
<220> FEATURE:
<223> OTHER INFORMATION: synthetic

<400> SEQUENCE: 30

Pro Pro Ser Gly Glu Leu Val Phe Leu Ile Arg Arg Asn Ser Phe Asp
1               5                   10                  15

Glu Gln Asn Glu Ile
        20

<210> SEQ ID NO 31
<211> LENGTH: 21
<212> TYPE: PRT
<213> ORGANISM: Artificial sequence
<220> FEATURE:
<223> OTHER INFORMATION: synthetic

<400> SEQUENCE: 31

Asn Pro Trp Gly Gln Leu Ile Asn Leu Phe Tyr Ile Pro Ser Gly Thr
1               5                   10                  15

Lys Gln Asn Gly Arg
            20

<210> SEQ ID NO 32
<211> LENGTH: 21
<212> TYPE: PRT
<213> ORGANISM: Artificial sequence
<220> FEATURE:
<223> OTHER INFORMATION: synthetic

<400> SEQUENCE: 32

Pro Pro Ser Arg Gln Met Ile Leu Val Ile Arg Gln Glu Ala Tyr Lys
1               5                   10                  15

Gln Gln Asn Ala Thr
            20

<210> SEQ ID NO 33
<211> LENGTH: 21
<212> TYPE: PRT
<213> ORGANISM: Artificial sequence
<220> FEATURE:
<223> OTHER INFORMATION: synthetic

<400> SEQUENCE: 33

Glu Pro Gly Ala Gly Leu Gln Leu Leu Thr Tyr Ile Phe Ser Asn Met
1               5                   10                  15

Asp Met Lys Gln Asp
            20

<210> SEQ ID NO 34
<211> LENGTH: 21
<212> TYPE: PRT
<213> ORGANISM: Artificial sequence
<220> FEATURE:
<223> OTHER INFORMATION: synthetic

<400> SEQUENCE: 34

Tyr Pro Asn Arg Gly Leu Gln Phe Leu Leu Lys Tyr Ile Thr Gly Asp
1               5                   10                  15

Asn Leu Val Lys Gly
            20

<210> SEQ ID NO 35
<211> LENGTH: 21
<212> TYPE: PRT
<213> ORGANISM: Artificial sequence
<220> FEATURE:
<223> OTHER INFORMATION: synthetic

<400> SEQUENCE: 35

Phe Pro Gly Lys Gly Pro Ala Leu Leu Ile Ala Ile Arg Pro Asp Val
1               5                   10                  15

Ser Glu Lys Lys Glu
            20

<210> SEQ ID NO 36
<211> LENGTH: 21
<212> TYPE: PRT
<213> ORGANISM: Artificial sequence
<220> FEATURE:
<223> OTHER INFORMATION: synthetic

<400> SEQUENCE: 36

```
Glu Thr Ala Lys Thr Pro Glu Ala Leu Phe Val Met Thr Leu Asn Gly
1               5                   10                  15

Asp Glu Lys Lys Lys
            20

<210> SEQ ID NO 37
<211> LENGTH: 21
<212> TYPE: PRT
<213> ORGANISM: Artificial sequence
<220> FEATURE:
<223> OTHER INFORMATION: synthetic

<400> SEQUENCE: 37

His Pro Gly Gly Gly Ile Val Ser Leu Phe Met Leu Ser Ser Gly Lys
1               5                   10                  15

Lys Lys His Gly Arg
            20

<210> SEQ ID NO 38
<211> LENGTH: 21
<212> TYPE: PRT
<213> ORGANISM: Artificial sequence
<220> FEATURE:
<223> OTHER INFORMATION: synthetic

<400> SEQUENCE: 38

Phe Pro Ser Gln Gly Pro Arg Phe Ile Ile Gln Gly Tyr Lys Thr Lys
1               5                   10                  15

Val Thr Asn Glu Val
            20

<210> SEQ ID NO 39
<211> LENGTH: 21
<212> TYPE: PRT
<213> ORGANISM: Artificial sequence
<220> FEATURE:
<223> OTHER INFORMATION: synthetic

<400> SEQUENCE: 39

Tyr Pro Ala Glu Gly Pro Thr Phe Leu Ile Ser Ile Ser Ser Ile Lys
1               5                   10                  15

Asp Lys Asn Glu Asp
            20

<210> SEQ ID NO 40
<211> LENGTH: 21
<212> TYPE: PRT
<213> ORGANISM: Artificial sequence
<220> FEATURE:
<223> OTHER INFORMATION: synthetic

<400> SEQUENCE: 40

Tyr Pro Gly Glu Gly Leu Gln Leu Leu Leu Lys Ala Thr Lys Ala Asp
1               5                   10                  15

Asp Lys Gly Ser Asn
            20

<210> SEQ ID NO 41
<211> LENGTH: 21
<212> TYPE: PRT
<213> ORGANISM: Artificial sequence
<220> FEATURE:
<223> OTHER INFORMATION: synthetic
```

<400> SEQUENCE: 41

Asp Pro Gly Lys Gly Leu Thr Ser Leu Leu Ile Gln Ser Ser Gln
1               5                   10                  15

Arg Glu Gln Thr Ser
            20

<210> SEQ ID NO 42
<211> LENGTH: 21
<212> TYPE: PRT
<213> ORGANISM: Artificial sequence
<220> FEATURE:
<223> OTHER INFORMATION: synthetic

<400> SEQUENCE: 42

Asp Thr Gly Arg Gly Pro Val Ser Leu Thr Ile Met Thr Phe Ser Glu
1               5                   10                  15

Asn Thr Lys Ser Asn
            20

<210> SEQ ID NO 43
<211> LENGTH: 21
<212> TYPE: PRT
<213> ORGANISM: Artificial sequence
<220> FEATURE:
<223> OTHER INFORMATION: synthetic

<400> SEQUENCE: 43

Asp Pro Gly Glu Gly Pro Val Leu Leu Ile Ala Leu Tyr Lys Ala Gly
1               5                   10                  15

Glu Leu Thr Ser Asn
            20

<210> SEQ ID NO 44
<211> LENGTH: 21
<212> TYPE: PRT
<213> ORGANISM: Artificial sequence
<220> FEATURE:
<223> OTHER INFORMATION: synthetic

<400> SEQUENCE: 44

Lys Tyr Gly Glu Gly Leu Ile Phe Leu Met Met Leu Gln Lys Gly Gly
1               5                   10                  15

Glu Glu Lys Ser His
            20

<210> SEQ ID NO 45
<211> LENGTH: 21
<212> TYPE: PRT
<213> ORGANISM: Artificial sequence
<220> FEATURE:
<223> OTHER INFORMATION: synthetic

<400> SEQUENCE: 45

Asp Pro Gly Lys Ser Leu Glu Ser Leu Phe Val Leu Leu Ser Asn Gly
1               5                   10                  15

Ala Val Lys Gln Glu
            20

<210> SEQ ID NO 46
<211> LENGTH: 21
<212> TYPE: PRT
<213> ORGANISM: Artificial sequence
<220> FEATURE:
<223> OTHER INFORMATION: synthetic

```
<400> SEQUENCE: 46

Gln Glu Lys Lys Ala Pro Thr Phe Leu Phe Met Leu Thr Ser Ser Gly
1               5                   10                  15

Ile Glu Lys Lys Ser
            20

<210> SEQ ID NO 47
<211> LENGTH: 21
<212> TYPE: PRT
<213> ORGANISM: Artificial sequence
<220> FEATURE:
<223> OTHER INFORMATION: synthetic

<400> SEQUENCE: 47

Lys His Gly Glu Ala Pro Val Phe Leu Met Ile Leu Leu Lys Gly Gly
1               5                   10                  15

Glu Gln Met Arg Arg
            20

<210> SEQ ID NO 48
<211> LENGTH: 21
<212> TYPE: PRT
<213> ORGANISM: Artificial sequence
<220> FEATURE:
<223> OTHER INFORMATION: synthetic

<400> SEQUENCE: 48

Lys His Gly Glu Ala Pro Val Phe Leu Met Ile Leu Leu Lys Gly Gly
1               5                   10                  15

Glu Gln Lys Gly His
            20

<210> SEQ ID NO 49
<211> LENGTH: 21
<212> TYPE: PRT
<213> ORGANISM: Artificial sequence
<220> FEATURE:
<223> OTHER INFORMATION: synthetic

<400> SEQUENCE: 49

Asp Pro Gly Lys Gly Pro Glu Phe Leu Phe Thr Leu Tyr Ser Ala Gly
1               5                   10                  15

Glu Glu Lys Glu Lys
            20

<210> SEQ ID NO 50
<211> LENGTH: 21
<212> TYPE: PRT
<213> ORGANISM: Artificial sequence
<220> FEATURE:
<223> OTHER INFORMATION: synthetic

<400> SEQUENCE: 50

Tyr Pro Ser Lys Pro Leu Gln Leu Leu Gln Arg Glu Thr Met Glu Asn
1               5                   10                  15

Ser Lys Asn Phe Gly
            20

<210> SEQ ID NO 51
<211> LENGTH: 21
<212> TYPE: PRT
<213> ORGANISM: Artificial sequence
<220> FEATURE:
```

-continued

```
<223> OTHER INFORMATION: synthetic

<400> SEQUENCE: 51

Arg Pro Gly Gly His Pro Val Phe Leu Ile Gln Leu Val Lys Ser Gly
1               5                   10                  15

Glu Val Lys Lys Gln
            20

<210> SEQ ID NO 52
<211> LENGTH: 21
<212> TYPE: PRT
<213> ORGANISM: Artificial sequence
<220> FEATURE:
<223> OTHER INFORMATION: synthetic

<400> SEQUENCE: 52

Ser Leu Asp Gln Gly Leu Gln Phe Leu Ile Gln Tyr Tyr Asn Gly Glu
1               5                   10                  15

Glu Arg Ala Lys Gly
            20

<210> SEQ ID NO 53
<211> LENGTH: 21
<212> TYPE: PRT
<213> ORGANISM: Artificial sequence
<220> FEATURE:
<223> OTHER INFORMATION: synthetic

<400> SEQUENCE: 53

Ser Leu Asp Gln Gly Leu Gln Phe Leu Ile His Tyr Tyr Asn Gly Glu
1               5                   10                  15

Glu Arg Ala Lys Gly
            20

<210> SEQ ID NO 54
<211> LENGTH: 21
<212> TYPE: PRT
<213> ORGANISM: Artificial sequence
<220> FEATURE:
<223> OTHER INFORMATION: synthetic

<400> SEQUENCE: 54

Phe Pro Lys Gln Ser Leu Met Leu Met Ala Thr Ser Asn Glu Gly Ser
1               5                   10                  15

Lys Ala Thr Tyr Glu
            20

<210> SEQ ID NO 55
<211> LENGTH: 21
<212> TYPE: PRT
<213> ORGANISM: Artificial sequence
<220> FEATURE:
<223> OTHER INFORMATION: synthetic

<400> SEQUENCE: 55

Phe Pro Lys Lys Ser Leu Met Leu Met Ala Thr Ser Asn Glu Gly Ser
1               5                   10                  15

Lys Ala Thr Tyr Glu
            20

<210> SEQ ID NO 56
<211> LENGTH: 21
<212> TYPE: PRT
<213> ORGANISM: Artificial sequence
```

```
<220> FEATURE:
<223> OTHER INFORMATION: synthetic

<400> SEQUENCE: 56

Phe Pro Lys Gln Ser Leu Met Leu Met Ala Thr Ser Asn Glu Gly Cys
1               5                   10                  15

Lys Ala Thr Tyr Glu
            20

<210> SEQ ID NO 57
<211> LENGTH: 21
<212> TYPE: PRT
<213> ORGANISM: Artificial sequence
<220> FEATURE:
<223> OTHER INFORMATION: synthetic

<400> SEQUENCE: 57

Phe Pro Lys Lys Ser Leu Met Gln Ile Ala Thr Ser Asn Glu Gly Ser
1               5                   10                  15

Lys Ala Thr Tyr Glu
            20

<210> SEQ ID NO 58
<211> LENGTH: 21
<212> TYPE: PRT
<213> ORGANISM: Artificial sequence
<220> FEATURE:
<223> OTHER INFORMATION: synthetic

<400> SEQUENCE: 58

Asp Pro Gly Leu Gly Leu Arg Leu Ile Tyr Phe Ser Tyr Asp Val Lys
1               5                   10                  15

Met Lys Glu Lys Gly
            20

<210> SEQ ID NO 59
<211> LENGTH: 21
<212> TYPE: PRT
<213> ORGANISM: Artificial sequence
<220> FEATURE:
<223> OTHER INFORMATION: synthetic

<400> SEQUENCE: 59

Gln Pro Gly Gln Ser Leu Thr Leu Ile Ala Thr Ala Asn Gln Gly Ser
1               5                   10                  15

Glu Ala Thr Tyr Glu
            20

<210> SEQ ID NO 60
<211> LENGTH: 21
<212> TYPE: PRT
<213> ORGANISM: Artificial sequence
<220> FEATURE:
<223> OTHER INFORMATION: synthetic

<400> SEQUENCE: 60

Thr Pro Gly Gln Gly Leu Gln Phe Leu Phe Glu Tyr Phe Ser Glu Thr
1               5                   10                  15

Gln Arg Asn Lys Gly
            20

<210> SEQ ID NO 61
<211> LENGTH: 21
<212> TYPE: PRT
```

```
<213> ORGANISM: Artificial sequence
<220> FEATURE:
<223> OTHER INFORMATION: synthetic

<400> SEQUENCE: 61

Thr Leu Gly Gln Gly Leu Gln Phe Leu Phe Glu Tyr Phe Ser Glu Thr
1               5                   10                  15

Gln Arg Asn Lys Gly
            20

<210> SEQ ID NO 62
<211> LENGTH: 21
<212> TYPE: PRT
<213> ORGANISM: Artificial sequence
<220> FEATURE:
<223> OTHER INFORMATION: synthetic

<400> SEQUENCE: 62

Ala Leu Gly Gln Gly Pro Gln Phe Ile Phe Gln Tyr Tyr Glu Glu Glu
1               5                   10                  15

Glu Arg Gln Arg Gly
            20

<210> SEQ ID NO 63
<211> LENGTH: 21
<212> TYPE: PRT
<213> ORGANISM: Artificial sequence
<220> FEATURE:
<223> OTHER INFORMATION: synthetic

<400> SEQUENCE: 63

Val Leu Gly Gln Gly Pro Gln Phe Ile Phe Gln Tyr Tyr Glu Lys Glu
1               5                   10                  15

Glu Arg Gly Arg Gly
            20

<210> SEQ ID NO 64
<211> LENGTH: 21
<212> TYPE: PRT
<213> ORGANISM: Artificial sequence
<220> FEATURE:
<223> OTHER INFORMATION: synthetic

<400> SEQUENCE: 64

Ala Leu Gly Leu Gly Leu Gln Leu Leu Trp Tyr Asp Glu Gly Glu
1               5                   10                  15

Glu Arg Asn Arg Gly
            20

<210> SEQ ID NO 65
<211> LENGTH: 21
<212> TYPE: PRT
<213> ORGANISM: Artificial sequence
<220> FEATURE:
<223> OTHER INFORMATION: synthetic

<400> SEQUENCE: 65

Ala Leu Gly Leu Gly Leu Gln Phe Leu Leu Trp Tyr Asp Glu Gly Glu
1               5                   10                  15

Glu Arg Asn Arg Gly
            20

<210> SEQ ID NO 66
<211> LENGTH: 21
```

```
<212> TYPE: PRT
<213> ORGANISM: Artificial sequence
<220> FEATURE:
<223> OTHER INFORMATION: synthetic

<400> SEQUENCE: 66

Ala Leu Gly Gln Gly Pro Gln Phe Ile Phe Gln Tyr Tyr Arg Glu Glu
1               5                   10                  15

Glu Asn Gly Arg Gly
            20

<210> SEQ ID NO 67
<211> LENGTH: 21
<212> TYPE: PRT
<213> ORGANISM: Artificial sequence
<220> FEATURE:
<223> OTHER INFORMATION: synthetic

<400> SEQUENCE: 67

Ser Leu Gly Gln Gly Pro Glu Phe Leu Ile Tyr Phe Gln Gly Thr Gly
1               5                   10                  15

Ala Ala Asp Asp Ser
            20

<210> SEQ ID NO 68
<211> LENGTH: 21
<212> TYPE: PRT
<213> ORGANISM: Artificial sequence
<220> FEATURE:
<223> OTHER INFORMATION: synthetic

<400> SEQUENCE: 68

Ser Leu Gly Gln Gly Pro Glu Leu Leu Ile Tyr Phe Gln Gly Thr Gly
1               5                   10                  15

Ala Ala Asp Asp Ser
            20

<210> SEQ ID NO 69
<211> LENGTH: 21
<212> TYPE: PRT
<213> ORGANISM: Artificial sequence
<220> FEATURE:
<223> OTHER INFORMATION: synthetic

<400> SEQUENCE: 69

Ala Leu Gly Gln Gly Pro Glu Phe Leu Thr Tyr Phe Gln Asn Glu Ala
1               5                   10                  15

Gln Leu Asp Lys Ser
            20

<210> SEQ ID NO 70
<211> LENGTH: 21
<212> TYPE: PRT
<213> ORGANISM: Artificial sequence
<220> FEATURE:
<223> OTHER INFORMATION: synthetic

<400> SEQUENCE: 70

Ala Leu Gly Gln Gly Pro Glu Phe Leu Thr Tyr Phe Asn Tyr Glu Ala
1               5                   10                  15

Gln Gln Asp Lys Ser
            20

<210> SEQ ID NO 71
```

```
<211> LENGTH: 21
<212> TYPE: PRT
<213> ORGANISM: Artificial sequence
<220> FEATURE:
<223> OTHER INFORMATION: synthetic

<400> SEQUENCE: 71

Thr Leu Gly Gln Gly Pro Glu Phe Leu Thr Tyr Phe Gln Asn Glu Ala
1               5                   10                  15

Gln Leu Glu Lys Ser
            20

<210> SEQ ID NO 72
<211> LENGTH: 21
<212> TYPE: PRT
<213> ORGANISM: Artificial sequence
<220> FEATURE:
<223> OTHER INFORMATION: synthetic

<400> SEQUENCE: 72

Asn Pro Gly Gln Gly Pro Glu Phe Leu Thr Tyr Phe Gln Asn Glu Ala
1               5                   10                  15

Gln Leu Glu Lys Ser
            20

<210> SEQ ID NO 73
<211> LENGTH: 21
<212> TYPE: PRT
<213> ORGANISM: Artificial sequence
<220> FEATURE:
<223> OTHER INFORMATION: synthetic

<400> SEQUENCE: 73

Ser Leu Gly Gln Gly Leu Glu Phe Leu Ile Tyr Phe Gln Gly Asn Ser
1               5                   10                  15

Ala Pro Asp Lys Ser
            20

<210> SEQ ID NO 74
<211> LENGTH: 21
<212> TYPE: PRT
<213> ORGANISM: Artificial sequence
<220> FEATURE:
<223> OTHER INFORMATION: synthetic

<400> SEQUENCE: 74

Ala Leu Gly Gln Gly Pro Glu Phe Leu Thr Tyr Phe Asn Tyr Glu Ala
1               5                   10                  15

Gln Pro Asp Lys Ser
            20

<210> SEQ ID NO 75
<211> LENGTH: 21
<212> TYPE: PRT
<213> ORGANISM: Artificial sequence
<220> FEATURE:
<223> OTHER INFORMATION: synthetic

<400> SEQUENCE: 75

Thr Leu Gly Gln Gly Ser Glu Val Leu Thr Tyr Ser Gln Ser Asp Ala
1               5                   10                  15

Gln Arg Asp Lys Ser
            20
```

```
<210> SEQ ID NO 76
<211> LENGTH: 21
<212> TYPE: PRT
<213> ORGANISM: Artificial sequence
<220> FEATURE:
<223> OTHER INFORMATION: synthetic

<400> SEQUENCE: 76

Lys Ala Lys Lys Pro Pro Glu Leu Met Phe Val Tyr Ser Tyr Glu Lys
1               5                   10                  15

Leu Ser Ile Asn Glu
            20

<210> SEQ ID NO 77
<211> LENGTH: 21
<212> TYPE: PRT
<213> ORGANISM: Artificial sequence
<220> FEATURE:
<223> OTHER INFORMATION: synthetic

<400> SEQUENCE: 77

Ser Ala Lys Lys Pro Leu Glu Leu Met Phe Val Tyr Ser Leu Glu Glu
1               5                   10                  15

Arg Val Glu Asn Asn
            20

<210> SEQ ID NO 78
<211> LENGTH: 21
<212> TYPE: PRT
<213> ORGANISM: Artificial sequence
<220> FEATURE:
<223> OTHER INFORMATION: synthetic

<400> SEQUENCE: 78

Ser Ala Lys Lys Pro Leu Glu Leu Met Phe Val Tyr Asn Phe Lys Glu
1               5                   10                  15

Gln Thr Glu Asn Asn
            20

<210> SEQ ID NO 79
<211> LENGTH: 21
<212> TYPE: PRT
<213> ORGANISM: Artificial sequence
<220> FEATURE:
<223> OTHER INFORMATION: synthetic

<400> SEQUENCE: 79

Thr Met Met Arg Gly Leu Glu Leu Leu Ile Tyr Phe Asn Asn Asn Val
1               5                   10                  15

Pro Ile Asp Asp Ser
            20

<210> SEQ ID NO 80
<211> LENGTH: 21
<212> TYPE: PRT
<213> ORGANISM: Artificial sequence
<220> FEATURE:
<223> OTHER INFORMATION: synthetic

<400> SEQUENCE: 80

Thr Met Met Gln Gly Leu Glu Leu Leu Ala Tyr Phe Arg Asn Arg Ala
1               5                   10                  15

Pro Leu Asp Asp Ser
            20
```

```
<210> SEQ ID NO 81
<211> LENGTH: 21
<212> TYPE: PRT
<213> ORGANISM: Artificial sequence
<220> FEATURE:
<223> OTHER INFORMATION: synthetic

<400> SEQUENCE: 81

Asp Ser Lys Lys Phe Leu Lys Ile Met Phe Ser Tyr Asn Asn Lys Glu
1               5                   10                  15

Leu Ile Ile Asn Glu
            20

<210> SEQ ID NO 82
<211> LENGTH: 21
<212> TYPE: PRT
<213> ORGANISM: Artificial sequence
<220> FEATURE:
<223> OTHER INFORMATION: synthetic

<400> SEQUENCE: 82

Lys Leu Glu Glu Glu Leu Lys Phe Leu Val Tyr Phe Gln Asn Glu Glu
1               5                   10                  15

Leu Ile Gln Lys Ala
            20

<210> SEQ ID NO 83
<211> LENGTH: 21
<212> TYPE: PRT
<213> ORGANISM: Artificial sequence
<220> FEATURE:
<223> OTHER INFORMATION: synthetic

<400> SEQUENCE: 83

Thr Leu Glu Glu Glu Leu Lys Phe Phe Ile Tyr Phe Gln Asn Glu Glu
1               5                   10                  15

Ile Ile Gln Lys Ala
            20

<210> SEQ ID NO 84
<211> LENGTH: 21
<212> TYPE: PRT
<213> ORGANISM: Artificial sequence
<220> FEATURE:
<223> OTHER INFORMATION: synthetic

<400> SEQUENCE: 84

Asp Pro Gly Met Glu Leu His Leu Ile His Tyr Ser Tyr Gly Val Asn
1               5                   10                  15

Ser Thr Glu Lys Gly
            20

<210> SEQ ID NO 85
<211> LENGTH: 21
<212> TYPE: PRT
<213> ORGANISM: Artificial sequence
<220> FEATURE:
<223> OTHER INFORMATION: synthetic

<400> SEQUENCE: 85

Asp Pro Gly His Gly Leu Arg Leu Ile His Tyr Ser Tyr Gly Val Lys
1               5                   10                  15

Asp Thr Asp Lys Gly
            20
```

<210> SEQ ID NO 86
<211> LENGTH: 21
<212> TYPE: PRT
<213> ORGANISM: Artificial sequence
<220> FEATURE:
<223> OTHER INFORMATION: synthetic

<400> SEQUENCE: 86

Asp Leu Gly His Gly Leu Arg Leu Ile His Tyr Ser Tyr Gly Val Gln
1               5                   10                  15

Asp Thr Asn Lys Gly
            20

<210> SEQ ID NO 87
<211> LENGTH: 21
<212> TYPE: PRT
<213> ORGANISM: Artificial sequence
<220> FEATURE:
<223> OTHER INFORMATION: synthetic

<400> SEQUENCE: 87

Asp Leu Gly His Gly Leu Arg Leu Ile His Tyr Ser Tyr Gly Val Lys
1               5                   10                  15

Asp Thr Asn Lys Gly
            20

<210> SEQ ID NO 88
<211> LENGTH: 21
<212> TYPE: PRT
<213> ORGANISM: Artificial sequence
<220> FEATURE:
<223> OTHER INFORMATION: synthetic

<400> SEQUENCE: 88

Asp Leu Gly His Gly Leu Arg Leu Ile His Tyr Ser Tyr Gly Val His
1               5                   10                  15

Asp Thr Asn Lys Gly
            20

<210> SEQ ID NO 89
<211> LENGTH: 21
<212> TYPE: PRT
<213> ORGANISM: Artificial sequence
<220> FEATURE:
<223> OTHER INFORMATION: synthetic

<400> SEQUENCE: 89

Asp Leu Gly His Gly Leu Arg Leu Ile Tyr Tyr Ser Ala Ala Ala Asp
1               5                   10                  15

Ile Thr Asp Lys Gly
            20

<210> SEQ ID NO 90
<211> LENGTH: 21
<212> TYPE: PRT
<213> ORGANISM: Artificial sequence
<220> FEATURE:
<223> OTHER INFORMATION: synthetic

<400> SEQUENCE: 90

Asp Pro Gly Met Gly Leu Arg Leu Ile His Tyr Ser Val Gly Ala Gly
1               5                   10                  15

Ile Thr Asp Gln Gly

-continued

<210> SEQ ID NO 91
<211> LENGTH: 21
<212> TYPE: PRT
<213> ORGANISM: Artificial sequence
<220> FEATURE:
<223> OTHER INFORMATION: synthetic

<400> SEQUENCE: 91

Asp Pro Gly Met Gly Leu Arg Leu Ile His Tyr Ser Val Gly Glu Gly
1               5                   10                  15

Thr Thr Ala Lys Gly
            20

<210> SEQ ID NO 92
<211> LENGTH: 21
<212> TYPE: PRT
<213> ORGANISM: Artificial sequence
<220> FEATURE:
<223> OTHER INFORMATION: synthetic

<400> SEQUENCE: 92

Asp Pro Gly Met Gly Leu Arg Leu Ile Tyr Tyr Ser Ala Ser Glu Gly
1               5                   10                  15

Thr Thr Asp Lys Gly
            20

<210> SEQ ID NO 93
<211> LENGTH: 21
<212> TYPE: PRT
<213> ORGANISM: Artificial sequence
<220> FEATURE:
<223> OTHER INFORMATION: synthetic

<400> SEQUENCE: 93

Asp Pro Gly Met Gly Leu Arg Arg Ile His Tyr Ser Val Ala Ala Gly
1               5                   10                  15

Ile Thr Asp Lys Gly
            20

<210> SEQ ID NO 94
<211> LENGTH: 21
<212> TYPE: PRT
<213> ORGANISM: Artificial sequence
<220> FEATURE:
<223> OTHER INFORMATION: synthetic

<400> SEQUENCE: 94

Asp Leu Gly Leu Gly Leu Arg Leu Ile His Tyr Ser Asn Thr Ala Gly
1               5                   10                  15

Thr Thr Gly Lys Gly
            20

<210> SEQ ID NO 95
<211> LENGTH: 21
<212> TYPE: PRT
<213> ORGANISM: Artificial sequence
<220> FEATURE:
<223> OTHER INFORMATION: synthetic

<400> SEQUENCE: 95

Asp Pro Gly Met Gly Leu Lys Leu Ile Tyr Tyr Ser Val Gly Ala Gly
1               5                   10                  15

```
Ile Thr Asp Lys Gly
            20

<210> SEQ ID NO 96
<211> LENGTH: 21
<212> TYPE: PRT
<213> ORGANISM: Artificial sequence
<220> FEATURE:
<223> OTHER INFORMATION: synthetic

<400> SEQUENCE: 96

Asp Pro Gly Met Gly Leu Arg Leu Ile Tyr Tyr Ser Ala Ala Ala Gly
1               5                   10                  15

Thr Thr Asp Lys Glu
            20

<210> SEQ ID NO 97
<211> LENGTH: 21
<212> TYPE: PRT
<213> ORGANISM: Artificial sequence
<220> FEATURE:
<223> OTHER INFORMATION: synthetic

<400> SEQUENCE: 97

Asp Pro Gly Leu Gly Leu Arg Gln Ile Tyr Tyr Ser Met Asn Val Glu
1               5                   10                  15

Val Thr Asp Lys Gly
            20

<210> SEQ ID NO 98
<211> LENGTH: 21
<212> TYPE: PRT
<213> ORGANISM: Artificial sequence
<220> FEATURE:
<223> OTHER INFORMATION: synthetic

<400> SEQUENCE: 98

Asp Pro Gly Leu Gly Leu Arg Leu Ile Tyr Tyr Ser Phe Asp Val Lys
1               5                   10                  15

Asp Ile Asn Lys Gly
            20

<210> SEQ ID NO 99
<211> LENGTH: 21
<212> TYPE: PRT
<213> ORGANISM: Artificial sequence
<220> FEATURE:
<223> OTHER INFORMATION: synthetic

<400> SEQUENCE: 99

Val Met Gly Lys Glu Ile Lys Phe Leu Leu His Phe Val Lys Glu Ser
1               5                   10                  15

Lys Gln Asp Glu Ser
            20

<210> SEQ ID NO 100
<211> LENGTH: 21
<212> TYPE: PRT
<213> ORGANISM: Artificial sequence
<220> FEATURE:
<223> OTHER INFORMATION: synthetic

<400> SEQUENCE: 100

Asp Pro Gly Gln Gly Leu Arg Leu Ile Tyr Tyr Ser Gln Ile Val Asn
1               5                   10                  15
```

Asp Phe Gln Lys Gly
            20

<210> SEQ ID NO 101
<211> LENGTH: 21
<212> TYPE: PRT
<213> ORGANISM: Artificial sequence
<220> FEATURE:
<223> OTHER INFORMATION: synthetic

<400> SEQUENCE: 101

Asp Pro Gly Gln Gly Leu Arg Leu Ile Tyr Tyr Ser His Ile Val Asn
1               5                   10                  15

Asp Phe Gln Lys Gly
            20

<210> SEQ ID NO 102
<211> LENGTH: 21
<212> TYPE: PRT
<213> ORGANISM: Artificial sequence
<220> FEATURE:
<223> OTHER INFORMATION: synthetic

<400> SEQUENCE: 102

Leu Pro Glu Glu Gly Leu Lys Phe Met Val Tyr Leu Gln Lys Glu Asn
1               5                   10                  15

Ile Ile Asp Glu Ser
            20

<210> SEQ ID NO 103
<211> LENGTH: 21
<212> TYPE: PRT
<213> ORGANISM: Artificial sequence
<220> FEATURE:
<223> OTHER INFORMATION: synthetic

<400> SEQUENCE: 103

Asn Gln Asn Lys Glu Phe Met Leu Leu Ile Ser Phe Gln Asn Glu Gln
1               5                   10                  15

Val Leu Gln Glu Thr
            20

<210> SEQ ID NO 104
<211> LENGTH: 21
<212> TYPE: PRT
<213> ORGANISM: Artificial sequence
<220> FEATURE:
<223> OTHER INFORMATION: synthetic

<400> SEQUENCE: 104

Asn Gln Asn Lys Glu Phe Met Phe Leu Ile Ser Phe Gln Asn Glu Gln
1               5                   10                  15

Val Leu Gln Glu Met
            20

<210> SEQ ID NO 105
<211> LENGTH: 21
<212> TYPE: PRT
<213> ORGANISM: Artificial sequence
<220> FEATURE:
<223> OTHER INFORMATION: synthetic

<400> SEQUENCE: 105

Ala Ala Gly Arg Gly Leu Gln Leu Leu Phe Tyr Ser Val Gly Ile Gly

```
                1               5                  10                 15

Gln Ile Ser Ser Glu
                20

<210> SEQ ID NO 106
<211> LENGTH: 21
<212> TYPE: PRT
<213> ORGANISM: Artificial sequence
<220> FEATURE:
<223> OTHER INFORMATION: synthetic

<400> SEQUENCE: 106

Ala Ala Gly Arg Gly Leu Gln Leu Leu Phe Tyr Ser Ile Gly Ile Asp
1               5                   10                  15

Gln Ile Ser Ser Glu
                20

<210> SEQ ID NO 107
<211> LENGTH: 21
<212> TYPE: PRT
<213> ORGANISM: Artificial sequence
<220> FEATURE:
<223> OTHER INFORMATION: synthetic

<400> SEQUENCE: 107

Ile Leu Gly Gln Gly Pro Glu Leu Leu Val Gln Phe Gln Asp Glu Ser
1               5                   10                  15

Val Val Asp Asp Ser
                20

<210> SEQ ID NO 108
<211> LENGTH: 21
<212> TYPE: PRT
<213> ORGANISM: Artificial sequence
<220> FEATURE:
<223> OTHER INFORMATION: synthetic

<400> SEQUENCE: 108

Asn Leu Gly Gln Gly Pro Glu Leu Leu Ile Arg Tyr Glu Asn Glu Glu
1               5                   10                  15

Ala Val Asp Asp Ser
                20

<210> SEQ ID NO 109
<211> LENGTH: 21
<212> TYPE: PRT
<213> ORGANISM: Artificial sequence
<220> FEATURE:
<223> OTHER INFORMATION: synthetic

<400> SEQUENCE: 109

Ile Leu Gly Gln Gly Pro Lys Leu Leu Ile Gln Phe Gln Asn Asn Gly
1               5                   10                  15

Val Val Asp Asp Ser
                20

<210> SEQ ID NO 110
<211> LENGTH: 21
<212> TYPE: PRT
<213> ORGANISM: Artificial sequence
<220> FEATURE:
<223> OTHER INFORMATION: synthetic

<400> SEQUENCE: 110
```

```
Ile Leu Gly Gln Lys Val Glu Phe Leu Val Ser Phe Tyr Asn Asn Glu
1               5                   10                  15

Ile Ser Glu Lys Ser
            20
```

<210> SEQ ID NO 111
<211> LENGTH: 21
<212> TYPE: PRT
<213> ORGANISM: Artificial sequence
<220> FEATURE:
<223> OTHER INFORMATION: synthetic

<400> SEQUENCE: 111

```
Gly Pro Gly Gln Asp Pro Gln Phe Phe Ile Ser Phe Tyr Glu Lys Met
1               5                   10                  15

Gln Ser Asp Lys Gly
            20
```

<210> SEQ ID NO 112
<211> LENGTH: 21
<212> TYPE: PRT
<213> ORGANISM: Artificial sequence
<220> FEATURE:
<223> OTHER INFORMATION: synthetic

<400> SEQUENCE: 112

```
Gly Pro Gly Gln Asp Pro Gln Phe Leu Ile Ser Phe Tyr Glu Lys Met
1               5                   10                  15

Gln Ser Asp Lys Gly
            20
```

<210> SEQ ID NO 113
<211> LENGTH: 21
<212> TYPE: PRT
<213> ORGANISM: Artificial sequence
<220> FEATURE:
<223> OTHER INFORMATION: synthetic

<400> SEQUENCE: 113

```
Lys Ser Ser Gln Ala Pro Lys Leu Leu Phe His Tyr Tyr Asn Lys Asp
1               5                   10                  15

Phe Asn Asn Glu Ala
            20
```

<210> SEQ ID NO 114
<211> LENGTH: 21
<212> TYPE: PRT
<213> ORGANISM: Artificial sequence
<220> FEATURE:
<223> OTHER INFORMATION: synthetic

<400> SEQUENCE: 114

```
Lys Ser Ser Gln Ala Pro Lys Leu Leu Phe His Tyr Tyr Asp Lys Asp
1               5                   10                  15

Phe Asn Asn Glu Ala
            20
```

<210> SEQ ID NO 115
<211> LENGTH: 21
<212> TYPE: PRT
<213> ORGANISM: Artificial sequence
<220> FEATURE:
<223> OTHER INFORMATION: synthetic

<400> SEQUENCE: 115

Val Leu Lys Asn Glu Phe Lys Phe Leu Ile Ser Phe Gln Asn Glu Asn
1               5                   10                  15

Val Phe Asp Glu Thr
            20

<210> SEQ ID NO 116
<211> LENGTH: 21
<212> TYPE: PRT
<213> ORGANISM: Artificial sequence
<220> FEATURE:
<223> OTHER INFORMATION: synthetic

<400> SEQUENCE: 116

Val Leu Lys Asn Glu Phe Lys Phe Leu Val Ser Phe Gln Asn Glu Asn
1               5                   10                  15

Val Phe Asp Glu Thr
            20

<210> SEQ ID NO 117
<211> LENGTH: 24
<212> TYPE: DNA
<213> ORGANISM: Artificial sequence
<220> FEATURE:
<223> OTHER INFORMATION: synthetic

<400> SEQUENCE: 117
ggcattaacg gttttgaggc tgga                                      24

<210> SEQ ID NO 118
<211> LENGTH: 24
<212> TYPE: DNA
<213> ORGANISM: Artificial sequence
<220> FEATURE:
<223> OTHER INFORMATION: synthetic

<400> SEQUENCE: 118
cagtgttcca gagggagcca ttgt                                      24

<210> SEQ ID NO 119
<211> LENGTH: 24
<212> TYPE: DNA
<213> ORGANISM: Artificial sequence
<220> FEATURE:
<223> OTHER INFORMATION: synthetic

<400> SEQUENCE: 119
ccgggcagca gacactgctt ctta                                      24

<210> SEQ ID NO 120
<211> LENGTH: 24
<212> TYPE: DNA
<213> ORGANISM: Artificial sequence
<220> FEATURE:
<223> OTHER INFORMATION: synthetic

<400> SEQUENCE: 120
ttggtatcga cagcttcact ccca                                      24

<210> SEQ ID NO 121
<211> LENGTH: 24
<212> TYPE: DNA
<213> ORGANISM: Artificial sequence
<220> FEATURE:
<223> OTHER INFORMATION: synthetic

<400> SEQUENCE: 121
cggccaccct gacctgcaac tata                                          24

<210> SEQ ID NO 122
<211> LENGTH: 24
<212> TYPE: DNA
<213> ORGANISM: Artificial sequence
<220> FEATURE:
<223> OTHER INFORMATION: synthetic

<400> SEQUENCE: 122
tccgccaacc ttgtcatctc cgct                                          24

<210> SEQ ID NO 123
<211> LENGTH: 24
<212> TYPE: DNA
<213> ORGANISM: Artificial sequence
<220> FEATURE:
<223> OTHER INFORMATION: synthetic

<400> SEQUENCE: 123
gcaacatgct ggcggagcac ccac                                          24

<210> SEQ ID NO 124
<211> LENGTH: 24
<212> TYPE: DNA
<213> ORGANISM: Artificial sequence
<220> FEATURE:
<223> OTHER INFORMATION: synthetic

<400> SEQUENCE: 124
cattcgttca aatgtgggca aaag                                          24

<210> SEQ ID NO 125
<211> LENGTH: 22
<212> TYPE: DNA
<213> ORGANISM: Artificial sequence
<220> FEATURE:
<223> OTHER INFORMATION: synthetic

<400> SEQUENCE: 125
gtgaatggag agaatgtgga gc                                            22

<210> SEQ ID NO 126
<211> LENGTH: 21
<212> TYPE: DNA
<213> ORGANISM: Artificial sequence
<220> FEATURE:
<223> OTHER INFORMATION: synthetic

<400> SEQUENCE: 126
tgagcagagg agagagtgtg g                                             21

<210> SEQ ID NO 127
<211> LENGTH: 24
<212> TYPE: DNA
<213> ORGANISM: Artificial sequence
<220> FEATURE:
<223> OTHER INFORMATION: synthetic

<400> SEQUENCE: 127
ccagtactcc agacaacgcc tgca                                          24

<210> SEQ ID NO 128
<211> LENGTH: 24

```
<212> TYPE: DNA
<213> ORGANISM: Artificial sequence
<220> FEATURE:
<223> OTHER INFORMATION: synthetic

<400> SEQUENCE: 128
cactgcggcc cagcctggtg atac                                              24

<210> SEQ ID NO 129
<211> LENGTH: 24
<212> TYPE: DNA
<213> ORGANISM: Artificial sequence
<220> FEATURE:
<223> OTHER INFORMATION: synthetic

<400> SEQUENCE: 129
cgctgctcat cctccaggtg cggg                                              24

<210> SEQ ID NO 130
<211> LENGTH: 24
<212> TYPE: DNA
<213> ORGANISM: Artificial sequence
<220> FEATURE:
<223> OTHER INFORMATION: synthetic

<400> SEQUENCE: 130
tcgtcggaac tcttttgatg agca                                              24

<210> SEQ ID NO 131
<211> LENGTH: 24
<212> TYPE: DNA
<213> ORGANISM: Artificial sequence
<220> FEATURE:
<223> OTHER INFORMATION: synthetic

<400> SEQUENCE: 131
ttcatcaaaa cccttgggga cagc                                              24

<210> SEQ ID NO 132
<211> LENGTH: 24
<212> TYPE: DNA
<213> ORGANISM: Artificial sequence
<220> FEATURE:
<223> OTHER INFORMATION: synthetic

<400> SEQUENCE: 132
cccagcaggc agatgattct cgtt                                              24

<210> SEQ ID NO 133
<211> LENGTH: 24
<212> TYPE: DNA
<213> ORGANISM: Artificial sequence
<220> FEATURE:
<223> OTHER INFORMATION: synthetic

<400> SEQUENCE: 133
ttgcagacac cgagactggg gact                                              24

<210> SEQ ID NO 134
<211> LENGTH: 24
<212> TYPE: DNA
<213> ORGANISM: Artificial sequence
<220> FEATURE:
<223> OTHER INFORMATION: synthetic

<400> SEQUENCE: 134
```

-continued

```
tcaacgttgc tgaagggaat cctc                                              24
```

<210> SEQ ID NO 135
<211> LENGTH: 24
<212> TYPE: DNA
<213> ORGANISM: Artificial sequence
<220> FEATURE:
<223> OTHER INFORMATION: synthetic

<400> SEQUENCE: 135

```
tgggaaaggc cgtgcattat tgat                                              24
```

<210> SEQ ID NO 136
<211> LENGTH: 24
<212> TYPE: DNA
<213> ORGANISM: Artificial sequence
<220> FEATURE:
<223> OTHER INFORMATION: synthetic

<400> SEQUENCE: 136

```
cagcaccaat ttcacctgca gctt                                              24
```

<210> SEQ ID NO 137
<211> LENGTH: 24
<212> TYPE: DNA
<213> ORGANISM: Artificial sequence
<220> FEATURE:
<223> OTHER INFORMATION: synthetic

<400> SEQUENCE: 137

```
acactggctg caacagcatc cagg                                              24
```

<210> SEQ ID NO 138
<211> LENGTH: 24
<212> TYPE: DNA
<213> ORGANISM: Artificial sequence
<220> FEATURE:
<223> OTHER INFORMATION: synthetic

<400> SEQUENCE: 138

```
tccctgttta tccctgccga caga                                              24
```

<210> SEQ ID NO 139
<211> LENGTH: 24
<212> TYPE: DNA
<213> ORGANISM: Artificial sequence
<220> FEATURE:
<223> OTHER INFORMATION: synthetic

<400> SEQUENCE: 139

```
agcaaaattc accatccctg agcg                                              24
```

<210> SEQ ID NO 140
<211> LENGTH: 24
<212> TYPE: DNA
<213> ORGANISM: Artificial sequence
<220> FEATURE:
<223> OTHER INFORMATION: synthetic

<400> SEQUENCE: 140

```
cctgaaagcc acgaaggctg atga                                              24
```

<210> SEQ ID NO 141
<211> LENGTH: 24
<212> TYPE: DNA
<213> ORGANISM: Artificial sequence

```
<220> FEATURE:
<223> OTHER INFORMATION: synthetic

<400> SEQUENCE: 141
tgcctcgctg gataaatcat cagg                                          24

<210> SEQ ID NO 142
<211> LENGTH: 24
<212> TYPE: DNA
<213> ORGANISM: Artificial sequence
<220> FEATURE:
<223> OTHER INFORMATION: synthetic

<400> SEQUENCE: 142
ctggatgcag acacaaagca gagc                                          24

<210> SEQ ID NO 143
<211> LENGTH: 24
<212> TYPE: DNA
<213> ORGANISM: Artificial sequence
<220> FEATURE:
<223> OTHER INFORMATION: synthetic

<400> SEQUENCE: 143
tggctacggt acaagccgga ccct                                          24

<210> SEQ ID NO 144
<211> LENGTH: 24
<212> TYPE: DNA
<213> ORGANISM: Artificial sequence
<220> FEATURE:
<223> OTHER INFORMATION: synthetic

<400> SEQUENCE: 144
agcgcagcca tgcaggcatg tacc                                          24

<210> SEQ ID NO 145
<211> LENGTH: 24
<212> TYPE: DNA
<213> ORGANISM: Artificial sequence
<220> FEATURE:
<223> OTHER INFORMATION: synthetic

<400> SEQUENCE: 145
aagcccgtct cagcaccctc caca                                          24

<210> SEQ ID NO 146
<211> LENGTH: 24
<212> TYPE: DNA
<213> ORGANISM: Artificial sequence
<220> FEATURE:
<223> OTHER INFORMATION: synthetic

<400> SEQUENCE: 146
tggttgtgca cgagcgagac actg                                          24

<210> SEQ ID NO 147
<211> LENGTH: 24
<212> TYPE: DNA
<213> ORGANISM: Artificial sequence
<220> FEATURE:
<223> OTHER INFORMATION: synthetic

<400> SEQUENCE: 147
gaagggtgga gaacagatgc gtcg                                          24
```

```
<210> SEQ ID NO 148
<211> LENGTH: 20
<212> TYPE: DNA
<213> ORGANISM: Artificial sequence
<220> FEATURE:
<223> OTHER INFORMATION: synthetic

<400> SEQUENCE: 148
agagtctctc agctggtaca                                              20

<210> SEQ ID NO 149
<211> LENGTH: 20
<212> TYPE: DNA
<213> ORGANISM: Artificial sequence
<220> FEATURE:
<223> OTHER INFORMATION: synthetic

<400> SEQUENCE: 149
gtctctcagc tggtacacgg                                              20

<210> SEQ ID NO 150
<211> LENGTH: 23
<212> TYPE: DNA
<213> ORGANISM: Artificial sequence
<220> FEATURE:
<223> OTHER INFORMATION: synthetic

<400> SEQUENCE: 150
gaaccctgac cctgccgtgt acc                                          23

<210> SEQ ID NO 151
<211> LENGTH: 22
<212> TYPE: DNA
<213> ORGANISM: Artificial sequence
<220> FEATURE:
<223> OTHER INFORMATION: synthetic

<400> SEQUENCE: 151
atcataaatt cgggtaggat cc                                           22

<210> SEQ ID NO 152
<211> LENGTH: 24
<212> TYPE: DNA
<213> ORGANISM: Artificial sequence
<220> FEATURE:
<223> OTHER INFORMATION: synthetic

<400> SEQUENCE: 152
gcacaacagt tccctgactt gcac                                         24

<210> SEQ ID NO 153
<211> LENGTH: 24
<212> TYPE: DNA
<213> ORGANISM: Artificial sequence
<220> FEATURE:
<223> OTHER INFORMATION: synthetic

<400> SEQUENCE: 153
tcatcaacca tgcaagcctg acct                                         24

<210> SEQ ID NO 154
<211> LENGTH: 24
<212> TYPE: DNA
<213> ORGANISM: Artificial sequence
<220> FEATURE:
<223> OTHER INFORMATION: synthetic
```

<400> SEQUENCE: 154
gtctctagag agaagaagga gcgc                24

<210> SEQ ID NO 155
<211> LENGTH: 24
<212> TYPE: DNA
<213> ORGANISM: Artificial sequence
<220> FEATURE:
<223> OTHER INFORMATION: synthetic

<400> SEQUENCE: 155
acatatgaga gtggatttgt catt                24

<210> SEQ ID NO 156
<211> LENGTH: 25
<212> TYPE: DNA
<213> ORGANISM: Artificial sequence
<220> FEATURE:
<223> OTHER INFORMATION: synthetic

<400> SEQUENCE: 156
atacttcagt gagacacaga gaaac               25

<210> SEQ ID NO 157
<211> LENGTH: 24
<212> TYPE: DNA
<213> ORGANISM: Artificial sequence
<220> FEATURE:
<223> OTHER INFORMATION: synthetic

<400> SEQUENCE: 157
ttccctaact atagctctga gctg                24

<210> SEQ ID NO 158
<211> LENGTH: 20
<212> TYPE: DNA
<213> ORGANISM: Artificial sequence
<220> FEATURE:
<223> OTHER INFORMATION: synthetic

<400> SEQUENCE: 158
aggcctgagg gatccgtctc                     20

<210> SEQ ID NO 159
<211> LENGTH: 22
<212> TYPE: DNA
<213> ORGANISM: Artificial sequence
<220> FEATURE:
<223> OTHER INFORMATION: synthetic

<400> SEQUENCE: 159
cctgaatgcc ccaacagctc tc                  22

<210> SEQ ID NO 160
<211> LENGTH: 24
<212> TYPE: DNA
<213> ORGANISM: Artificial sequence
<220> FEATURE:
<223> OTHER INFORMATION: synthetic

<400> SEQUENCE: 160
atttacttta acaacaacgt tccg                24

<210> SEQ ID NO 161

<211> LENGTH: 24
<212> TYPE: DNA
<213> ORGANISM: Artificial sequence
<220> FEATURE:
<223> OTHER INFORMATION: synthetic

<400> SEQUENCE: 161
cctaaatctc cagacaaagc tcac                                24

<210> SEQ ID NO 162
<211> LENGTH: 24
<212> TYPE: DNA
<213> ORGANISM: Artificial sequence
<220> FEATURE:
<223> OTHER INFORMATION: synthetic

<400> SEQUENCE: 162
ctccaaaaac tcatcctgta cctt                                24

<210> SEQ ID NO 163
<211> LENGTH: 24
<212> TYPE: DNA
<213> ORGANISM: Artificial sequence
<220> FEATURE:
<223> OTHER INFORMATION: synthetic

<400> SEQUENCE: 163
tcaacagtct ccagaataag gacg                                24

<210> SEQ ID NO 164
<211> LENGTH: 24
<212> TYPE: DNA
<213> ORGANISM: Artificial sequence
<220> FEATURE:
<223> OTHER INFORMATION: synthetic

<400> SEQUENCE: 164
actgacaaag gagaagtctc agat                                24

<210> SEQ ID NO 165
<211> LENGTH: 25
<212> TYPE: DNA
<213> ORGANISM: Artificial sequence
<220> FEATURE:
<223> OTHER INFORMATION: synthetic

<400> SEQUENCE: 165
cactgaccaa ggagaagtcc ccaat                               25

<210> SEQ ID NO 166
<211> LENGTH: 25
<212> TYPE: DNA
<213> ORGANISM: Artificial sequence
<220> FEATURE:
<223> OTHER INFORMATION: synthetic

<400> SEQUENCE: 166
ctcagttggt gagggtacaa ctgcc                               25

<210> SEQ ID NO 167
<211> LENGTH: 24
<212> TYPE: DNA
<213> ORGANISM: Artificial sequence
<220> FEATURE:
<223> OTHER INFORMATION: synthetic

<400> SEQUENCE: 167

```
gtctctcgaa aagagaagag gaat                                              24

<210> SEQ ID NO 168
<211> LENGTH: 24
<212> TYPE: DNA
<213> ORGANISM: Artificial sequence
<220> FEATURE:
<223> OTHER INFORMATION: synthetic

<400> SEQUENCE: 168
agtgtctctc gacaggcaca ggct                                              24

<210> SEQ ID NO 169
<211> LENGTH: 24
<212> TYPE: DNA
<213> ORGANISM: Artificial sequence
<220> FEATURE:
<223> OTHER INFORMATION: synthetic

<400> SEQUENCE: 169
aaagagtcta aacaggatga gtcc                                              24

<210> SEQ ID NO 170
<211> LENGTH: 28
<212> TYPE: DNA
<213> ORGANISM: Artificial sequence
<220> FEATURE:
<223> OTHER INFORMATION: synthetic

<400> SEQUENCE: 170
ctactcacag atagtaaatg actttcag                                          28

<210> SEQ ID NO 171
<211> LENGTH: 24
<212> TYPE: DNA
<213> ORGANISM: Artificial sequence
<220> FEATURE:
<223> OTHER INFORMATION: synthetic

<400> SEQUENCE: 171
gatgagtcag gaatgccaaa ggaa                                              24

<210> SEQ ID NO 172
<211> LENGTH: 24
<212> TYPE: DNA
<213> ORGANISM: Artificial sequence
<220> FEATURE:
<223> OTHER INFORMATION: synthetic

<400> SEQUENCE: 172
caatgcccca agaacgcacc ctgc                                              24

<210> SEQ ID NO 173
<211> LENGTH: 24
<212> TYPE: DNA
<213> ORGANISM: Artificial sequence
<220> FEATURE:
<223> OTHER INFORMATION: synthetic

<400> SEQUENCE: 173
agctctgagg tgccccagaa tctc                                              24

<210> SEQ ID NO 174
<211> LENGTH: 24
<212> TYPE: DNA
```

-continued

```
<213> ORGANISM: Artificial sequence
<220> FEATURE:
<223> OTHER INFORMATION: synthetic

<400> SEQUENCE: 174
tgtggctttt tggtgcaatc ctat                                            24

<210> SEQ ID NO 175
<211> LENGTH: 24
<212> TYPE: DNA
<213> ORGANISM: Artificial sequence
<220> FEATURE:
<223> OTHER INFORMATION: synthetic

<400> SEQUENCE: 175
gttttatgaa aagatgcaga gcga                                            24

<210> SEQ ID NO 176
<211> LENGTH: 24
<212> TYPE: DNA
<213> ORGANISM: Artificial sequence
<220> FEATURE:
<223> OTHER INFORMATION: synthetic

<400> SEQUENCE: 176
ataatgaaat ctcagagaag tctg                                            24

<210> SEQ ID NO 177
<211> LENGTH: 21
<212> TYPE: DNA
<213> ORGANISM: Artificial sequence
<220> FEATURE:
<223> OTHER INFORMATION: synthetic

<400> SEQUENCE: 177
gcagacaccc ctgataactt c                                               21

<210> SEQ ID NO 178
<211> LENGTH: 30
<212> TYPE: DNA
<213> ORGANISM: Artificial sequence
<220> FEATURE:
<223> OTHER INFORMATION: synthetic

<400> SEQUENCE: 178
cgtagaattc gacttgacag cggaagtggt                                      30

<210> SEQ ID NO 179
<211> LENGTH: 22
<212> TYPE: DNA
<213> ORGANISM: Artificial sequence
<220> FEATURE:
<223> OTHER INFORMATION: synthetic

<400> SEQUENCE: 179
ctgcttctga tggctcaaac ac                                              22

<210> SEQ ID NO 180
<211> LENGTH: 20
<212> TYPE: DNA
<213> ORGANISM: Artificial sequence
<220> FEATURE:
<223> OTHER INFORMATION: synthetic

<400> SEQUENCE: 180
cgctgtcaag tccagttcta                                                 20
```

```
<210> SEQ ID NO 181
<211> LENGTH: 20
<212> TYPE: DNA
<213> ORGANISM: Artificial sequence
<220> FEATURE:
<223> OTHER INFORMATION: synthetic

<400> SEQUENCE: 181
tctcttgacc atggccatca                                              20
```

METHODS OF SELECTING T CELL RECEPTOR V PEPTIDES FOR THERAPEUTIC USE

PRIORITY CLAIM

This is a continuation-in-part of U.S. application Ser. No. 09/853,830, filed May 10, 2001, now abandoned which claims the benefit of U.S. Provisional Application No. 60/203,984, filed May 12, 2000, both of which are incorporated by reference herein in their entirety. This case also claims the benefit of U.S. Provisional Application No. 60/380,731, filed May 14, 2002, which is incorporated by reference in its entirety.

STATEMENT OF GOVERNMENT SUPPORT

This invention was made with United States government support pursuant to grant NS23221, from the National Institutes of Health and support from the Department of Veterans Affairs; the United States government has certain rights in the invention.

FIELD

This invention relates to the field of immunology and, more specifically, to methods of selecting T cell receptor peptides for therapeutic use.

BACKGROUND

Autoimmune diseases affect about 5% of the human population, often causing chronic, debilitating illnesses. Although all individuals have immune cells that potentially react with antigens present on their own tissues, these autoreactive cells are normally held in check by complex and currently poorly understood regulatory mechanisms. In individuals who develop autoimmune disease, these regulatory mechanisms are proposed to be somehow defective, which allows autoreactive cells to mount an immunological attack against host tissues.

Animal models have aided in understanding the mechanisms underlying autoimmune diseases. For example, experimental allergic encephalomyelitis (EAE) is an autoimmune disease of the central nervous system that can be induced in mice and rats by immunization with myelin basic protein (MBP). Histologically and clinically, EAE resembles multiple sclerosis (MS) in humans. EAE is mediated by T cells having specificity for myelin antigens, such as MBP, as evidenced by the ability of MBP- or other myelin-reactive T cells to induce EAE when adoptively transferred to healthy hosts. Analysis of the antigen-binding receptor, or T cell receptor (TCR), expressed by MBP-reactive T cells has generally revealed that these T cells express a limited number of TCR V alpha (AV, α) and TCR V beta (BV, β) polypeptide chains.

The TCR is a heterodimeric glycoprotein present on the surface of T cells. The TCR exists in two forms, one consisting of an alpha chain and a beta chain, the second consisting of a gamma chain and a delta chain. Each TCR polypeptide chain is encoded by a genetic locus containing multiple discontinuous gene segments. These include variable (V) region gene segments, joining (J) region gene segments and constant (C) region gene segments. Beta and delta chains contain an additional element termed the diversity (D) gene segment. The TCR gene segments become rearranged during T cell maturation to form VJ or VDJ genes, which are then expressed as polypeptide chains. There are at least 50 different human Vα (or AV), 57-70 Vβ (or BV), 3 Vδ (or GV) and 7Vγ (or DV) gene segments, which are categorized into various families, with members of a family sharing substantial nucleotide and amino acid sequence identity.

EAE has successfully been prevented or treated by various methods that selectively target the TCR V genes present on encephalitogenic T cells. Such therapeutic methods include immunization with TCR V region peptides to induce an immune response against the autoreactive T cells, and administering anti-TCR V region antibodies to bind and either kill or inactivate the autoreactive T cells. Once the disease-associated TCR V genes are identified in humans, analogous immunotherapeutic methods that target T cells expressing these V genes are also expected to be effective. However, a need remains to provide an efficient and effective means to identify TCR V genes of use in therapeutic strategies.

Human autoimmune diseases have proven to be more complex than experimental animal models, in part because there are numerous autoantigens implicated in human diseases, and human responses to different autoantigens depend on multiple genetic factors. In certain studies, T cells from individuals with autoimmune disease that react to proposed autoantigens have been demonstrated to express a limited subset of V genes. However, the relevance of these T cells to the disease is as yet unclear, because the particular antigen used in assessing T cell reactivity is not necessarily involved in the etiology of the disease in that individual. In certain studies, T cells obtained from the site of the pathology from individuals with autoimmune disease have been demonstrated to express a limited subset of V genes. Unfortunately, the currently available methods of identifying TCR V gene usage do not take into account the regulatory mechanisms that may be acting in a particular individual to control the activity of the relevant T cells.

Thus, there exists a need for an improved method of identifying disease-associated T cells in individuals, including both autoreactive T cells and regulatory T cells. Once the identity of the disease-associated T cells is known, appropriate, individualized therapies can be selected to prevent or treat the disease. Thus, there also exists a need for assays to efficiently and effectively select therapeutic agents of use.

SUMMARY

A method is disclosed herein to identify a T cell receptor (TCR) variable (V) peptide of use as a therapeutic agent in a subject. The method includes screening TCR V beta peptides, TCR V alpha peptides, or both TCR V beta peptides and TCR V alpha peptides to select a TCR V peptide that produces altered expression of a cytokine elicited in response to the TCR V peptide by T cells from the subject, and determining a regulatory activity of CD4+CD25+ T cells isolated from the subject elicited in response to the TCR V polypeptide. In one embodiment, the subject has an autoimmune disease.

In one embodiment, a method is also disclosed for monitoring the efficacy of a T Cell Receptor (TCR) V peptide for the treatment of a subject. The method includes exposing CD4+ cells from the subject to the TCR V peptide; and determining a T cell regulatory activity of CD4+CD25+ T cells isolated from the subject.

In another embodiment, a method is disclosed that is of use for selecting a therapy for a subject having an autoimmune disease. The method includes identifying a T Cell Receptor Variable (TCR V) gene expressed by target T cells in the subject by determining expression of a TCR V gene by activated T cells from the individual; and determining expression of a cytokine elicited in response to one or more TCR V peptides corresponding to the TCR V gene by T cells from the individual, thereby identifying a TCR V gene expressed by target T cells. The method also includes identifying a TCR V peptide corresponding to the TCR V gene that elicits T cell regulatory activity by a T cell isolated from the subject.

The foregoing and other features and advantages will become more apparent from the following detailed description of several embodiments, which proceeds with reference to the accompanying figures.

BRIEF DESCRIPTION OF THE FIGURES

FIG. 4 is a set of bar graphs showing the average IL-10 responses from subjects.

FIG. 5 is a series of bar graphs showing detection of Treg activity in the blood from a healthy control and a TCR-specific T cell line, but not in blood from an MS patient.

FIG. 7 is a set of bar graphs showing Treg activity. FIG. 7C is a bar graph of MS-111 (peptide/IFA) PBMC Treg assay.

SEQUENCE LISTING

Figure 1:
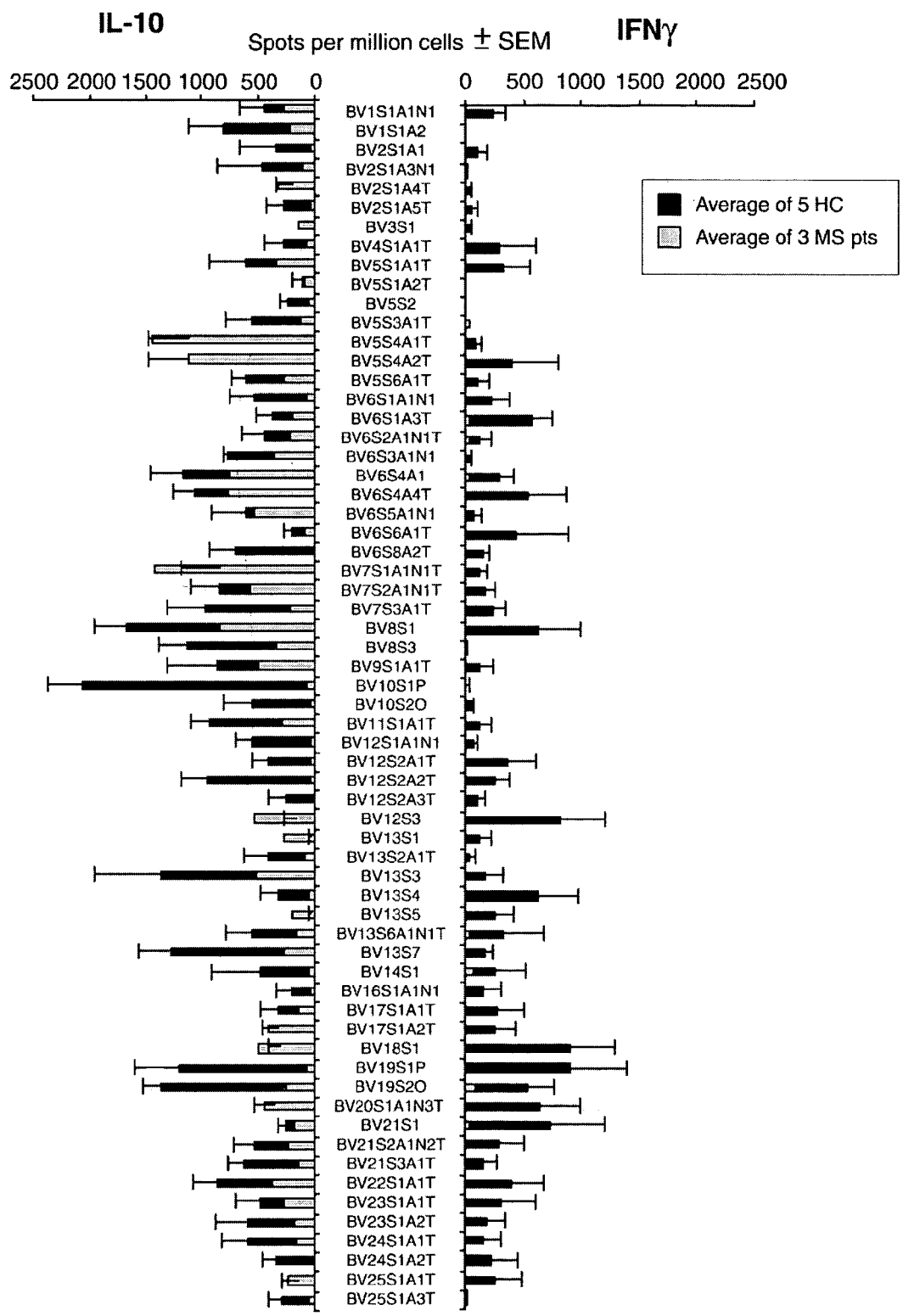
FIG. 1 is a bar graph showing cytokine production in response to BV CDR2 peptides. Solid bars represent mean frequencies per million PBMC±SEM of TCR BV specific IL-10 or IFN-γ-secreting cells (background subtracted) for 5 healthy controls. Superimposed gray bars represent mean frequencies for 3 MS patients (error bars not given for clarity). In some cases where mean frequency for MS donors is greater than HC (i.e. BV5S4A1T), the solid bar is obscured, but the mean frequency for HC can be discerned by locating the origin of the error bar. Designations: B=beta chain; V=variable region; BV1-25=family; S1-8=subfamily; A1-6=allele; N1-4=single nucleotide difference; T=tentative; O=orphon gene (located on different chromosome from TCR complex); P=pseudogene (contains a stop codon within the coding region).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

DETAILED DESCRIPTION

I.

| Abbreviations | |
|---|---|
| APC | antigen presenting cell |
| CD | cluster of differentiation |
| CDR | complementarity determining region |
| Cpm | counts per minute |
| FACS | fluorescence activated cell sorting |
| IFN | interferon |
| IL | interleukin |
| HC | healthy control |
| MS | multiple sclerosis |
| PBMC | peripheral blood mononuclear cells |
| TCR | T Cell Receptor |
| Treg | Regulatory T cell |
| $I_{50}$ | Inhibitory dose (50%) |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes.

Autoimmune disease: A disease in which the immune system produces an immune response (e.g. a B cell or a T cell response) against an antigen that is part of the normal host, with consequent injury to tissues. An autoantigen may be derived from a host cell, or may be derived from a commensal organism such as the microorganisms (known as commensal organisms) that normally colonise mucosal surfaces.

Exemplary autoimmune diseases affecting mammals include rheumatoid arthritis (RA), juvenile oligoarthritis, collagen-induced arthritis, adjuvant-induced arthritis, Sjogren's syndrome, multiple sclerosis (MS), experimental autoimmune encephalomyelitis (EAE), inflammatory bowel disease (e.g. Crohn's disease, ulceritive colitis), autoimmune gastric atrophy, pemphigus vulgaris, psoriasis, vitiligo, type I diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia pernicious anemia, and the like.

CD4: Cluster of differentiation factor 4 polypeptide, a T cell surface protein that mediates interaction with the MHC class II molecule. A T cell that expresses CD4 is a "CD4+" T cell.

CD4+ T cell mediated immunity: An immune response implemented by CD4+ T cells.

CD25: Cluster of differentiation factor 25, the IL-2 receptor alpha chain. A T cell that expresses CD25 is a "CD25+" T cell.

Cytokine: Proteins made by cells that affect the behavior of other cells, such as lymphocytes. In one embodiment, a cytokine is a chemokine, a molecule whose functions include the direction of cellular trafficking. A "regulatory cytokine" is intended to include Th2 cytokines such as interleukin-10 (IL-10), IL-4, IL-13, transforming growth factor beta (TGFβ), and other cytokines that are predominantly anti-inflammatory. Other cytokines that under appropriate conditions have anti-inflammatory effects include IL-5, TNF-α, IL-9, IFNβ and IFN-γ.

Immune response: A response of a cell of the immune system, such as a B cell, T cell, macrophage or polymorphonucleocyte, to a stimulus. An immune response can include any cell of the body involved in a host defense response for example, an epithelial cell that secretes interferon or a chemokine. An immune response includes, but is not limited to, an innate immune response or inflammation. In one embodiment, the immune response is specific for a particular antigen (an "antigen-specific immune response"). In one embodiment, an immune response is a T cell response, such as a Th1, Th2, or Th3 response.

Immunoregulatory response: An immune response that regulates a subsequent inflammatory response or an immune response. An immunoregulatory response can be a suppressive response, which suppresses another immune response or inflammatory response. In one non-limiting example, a suppressive immune response involves immunoregulatory T cells (Treg) or T suppressor cells. In one non-limiting example, an immunoregulatory response involves the production of anti-inflammatory cytokines. An immunoregulatory response can be an activating response, which activates another immune response or inflammatory response. In one specific, non-limiting example, an activating immune response involves the up-regulation of cytokines. An assay for a "regulatory activity" of a T cell is a functional assay for immunoregulatory activity. Thus, not only must expression of a cytokine be determined, but it must be shown that the cytokine has an effect on a cell. In one specific, non-limiting example, a regulatory activity requires cell-to-cell contact.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a host cell as well as chemically synthesized nucleic acids.

Leukocyte: Cells in the blood, also termed "white cells," that are involved in defending the body against infective organisms and foreign substances. Leukocytes are produced in the bone marrow. There are 5 main types of white blood cell, subdivided between 2 main groups: polymorphonuclear leukocytes (neutrophils, eosinophils, basophils) and mononuclear leukocytes (monocytes and lymphocytes). When an infection is present, the production of leukocytes increases.

Lymphocytes: A type of white blood cell that is involved in the immune defenses of the body. There are two main types of lymphocytes: B cells and T cells.

Lymphoproliferation: An increase in the production of lymphocytes.

Mammal: This term includes both human and non-human mammals. Similarly, the term "subject" includes both human and veterinary subjects.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide: A linear polynucleotide sequence of up to about 200 nucleotide bases in length, for example a polynucleotide (such as DNA or RNA) which is at least 6 nucleotides, for example at least 15, 50, 100 or even 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Similarly, an IRES (internal ribosomal entry site) is operably linked to a coding sequence if it allows entry of a ribosome, and subsequent translation of the coding sequence. Generally, operably linked DNA sequences are contiguous. Expression of two genes encoded by the same plasmid is regarded as operably linked if they are driven by one promoter and an IRES.

Pharmaceutical agent or drug: A chemical compound, peptide or other composition capable of inducing a desired therapeutic or prophylactic effect when properly administered to a subject.

Pharmaceutically acceptable carriers: The pharmaceutically acceptable carriers useful in this invention are conventional. *Remington's Pharmaceutical Sciences,* by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: A linear nucleotide sequence, including sequences of greater than 100 nucleotide bases in length.

Polypeptide: Any chain of amino acids, regardless of length or post-translational modification (e.g., glycosylation or phosphorylation). A "peptide" is a chain of less than amino acids, such as a chain of about 10, 15, 20, 25, 30, 35, 40, 50, 75 or 100 amino acids in length.

Preventing or treating a disease: "Preventing" a disease refers to inhibiting the full development of a disease, for example in a person who is known to have a predisposition to a disease such as an autoimmune disorder. An example of a person with a known predisposition is someone with a history of multiple sclerosis in the family, or who has been exposed to factors that predispose the subject to a condition, such as lupus or rheumatoid arthritis. "Treatment" refers to a therapeutic intervention that ameliorates a sign or symptom of a disease or pathological condition, such as the symptoms associated with organ transplant rejection. As used herein, the term "ameliorating," with reference to an autoimmune pathology, refers to any observable beneficial effect of the treatment. The beneficial effect can be evidenced, for example, by a delayed onset of clinical symptoms in a susceptible mammal, a reduction in severity of some or all clinical symptoms of the disease, a slower progression of the disease, a reduction in the number of relapses of the disease, a reduction in the number or activity (such as cytokine secretion) of pathogenic T cells at the site of pathology or in the circulation, an improvement in the overall health or well-being of the individual, or by other parameters well known in the art that are specific to the particular disease. Those skilled in the art can determine, based on knowledge of the expected course of the particular disease, whether there is a delayed onset of clinical symptoms. Those skilled in the art can also determine whether there is an amelioration of the clinical symptoms or reduction in the number or activity of pathogenic T cells following treatment as compared with before treatment or as compared to an untreated subject.

Portion of a nucleic acid sequence: At least 10, 20, 30 or 40 contiguous nucleotides of the relevant sequence, such as a sequence encoding an antigen. In some instances it would be advantageous to use a portion consisting of 50 or more nucleotides. In one specific non-limiting example, when describing a portion of an TCR V polypeptide it may be advantageous to utilize a relevant sequence encoding at least 10, 20, 30, 40, 50 or 100 amino acids of the TCR V polypeptide.

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. The promoter can be a constitutive or an inducible promoter. A specific, non-limiting example of a promoter is the HCMV IE promoter.

Purified: The term purified does not require absolute purity; rather, it is intended as a relative term. Thus, for example, a purified peptide preparation is one in which the peptide or protein is more enriched than the peptide or protein is in its natural environment within a cell. Preferably, a preparation is purified such that the protein or peptide represents at least 50% of the total peptide or protein content of the preparation. In several embodiments, a peptide is substantially purified if it is 85%, 90%, 95%, or 99% purified.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. Similarly, a recombinant protein is one encoded for by a recombinant nucleic acid molecule.

Regulatory activity of a T Cell: A detectable property that correlates with Th2-type, anti-inflammatory T cell activity. The particular regulatory activity to detect in the method will depend on the type and sensitivity of the assay used, and can be chosen by one of skill in the art. In one embodiment, a regulatory activity is demonstrated by CD4+CD25+ T cells. In this embodiment, an assay can be used that determines the regulatory activity of a CD4+CD25+ T cell. In one specific, non-limiting example, CD4+CD25+ T cells isolated from a subject are contacted with a TCR V peptide of interest, and the proliferation of CD4+CD25− T cells isolated from the subject that are co-incubated with the CD4+CD25+ T cells is assessed (see the Examples below). In anther specific, non-limiting example, secretion of a cytokine is assessed.

Subject: Living, multicellular vertebrate organisms, a category that includes both human and veterinary subjects for example, mammals, birds and primates.

Therapeutically effective dose: A dose sufficient to have a therapeutic effect, for example to prevent advancement, or to cause regression of a disease, such as an autoimmune disease. A therapeutically effective dose can also be a dose which is capable of relieving symptoms caused by the disease, such as pain or swelling.

T Cells and Immunoregulatory T Cells: T cells are a key cell type in the human cellular immune system, providing both function and biochemical control. T cells are classified based on which cell surface receptors and cytokines they express. The expression of cell surface receptors CD4 and/or CD8 are generally used to define two broad classes of T cells; these cell surface receptors are involved in recognizing antigens presented to the T cells by antigen presenting cells (APC). Certain mature T cells express only CD4 but not CD8 (termed CD4+ cells), while other mature T cells express CD8 but not CD4 (termed CD8+ cells).

CD8+ cells recognize peptide antigens that are presented on MHC class I molecules. Upon activation by an APC (which involves binding of both a stimulatory antigen and a costimulatory ligand), a CD8+ T cell matures into a cytotoxic T cell, which has defined functions and characteristics. CD4+ T cells recognize antigens that are presented on MHC class II molecules. When activated by an APC, CD4+ T cells can differentiate into T helper (Th) cells. Th cells have been divided into subclasses based on their cytokine secretion profiles. Th1 cells secrete a specific set of cytokines, including interferon-γ (IFN-γ) and interleukin-12 (IL-12), interleukin-2 (IL-2), interferon-γ and lymphotoxin and activate the cellular immunity processes (such as macrophage activation and induction of IgG antibodies by B cells). Th2 cells secrete different cytokines (particularly IL-4, IL-5 and IL-10), and mediate humoral immunity and allergic reactions.

An "immunoregulatory T cell" (Treg) is a CD4+ cell that inhibits proliferation of other cell populations in vitro. In one embodiment, an immunoregulatory T cell is a CD4+CD25+ T cell. Without being bound by theory, Treg cells are a product of normal thymic selection, and may arise from relatively high avidity interaction with self-peptide-MHC complexes. IL-10, and perhaps TGF-β, but not IL-4 appear to be crucial for the differentiation of Treg cells. Suppressive activity requires activation of Treg cells through their TCR, does not involve killing of responder cells, and is mediated in part through a contact dependent mechanism. The properties of CD4+CD25+ cells have recently been reviewed (see Baecher-Allan et al., *J. Immunol.* 167:1245-53, 2001). An assay for detecting T cell regulatory activity is disclosed herein.

T Cell Receptor (TCR) and TCR Receptor Peptides: Membrane-bound proteins composed of two transmembrane chains that are found on T cells. The T cell receptor recognizes antigen peptides presented in the context of the Major Histocompatibility Complex (MHC) proteins. In the case of CD4+ T cells, the antigen peptides must be presented on Class II MHC, and in the case of CD8+ T cells, the antigen peptides must be presented on Class I MHC. The T cell antigen receptor consists of either an alpha/beta chain or a gamma/delta chain associated with the CD3 molecular complex. The two transmembrane chains consist of two domains, called a "variable" and a "constant" domain, and a short hinge that connects the two domains. The V domains include V-, D-, and J-immunoglobulin like elements in the β chanin and V- and J-like elements in the a chain.

A "TCR V" peptide is a portion of the variable (V) region of the TCR itself, such as a peptide that includes about 10, 20, 30, 40 or about 50 consecutive amino acids of the V region of the TCR, or a variant thereof. A "variant" of a TCR peptide is a molecule substantially similar to either the entire peptide or a fragment thereof, such as about 75%, 80%, 90%, 95%, or 99% similar. In one embodiment, a variant includes an amino acid substitution, such as at least one conservative amino acid substitution. Conservative" amino acid substitutions include those listed below.

| Original Residue | Conservative Substitutions |
|---|---|
| Ala | Ser; Gly |
| Arg | Lys |
| Asn | Gly, His |
| Asp | Glu |
| Cys | Ser |
| Gln | Asn |
| Glu | Asp |
| Gly | Ala; Pro |
| His | Asn; Gln |
| Ile | Leu, Val |
| Leu | Ile; Val |
| Lys | Arg; Gln; Glu |
| Met | Leu; Ile; Tyr |
| Phe | Met; Leu; Tyr |
| Ser | Thr |
| Thr | Ser |
| Trp | Tyr |
| Tyr | Trp; Phe |
| Val | Ile; Leu |

Variant peptides may be conveniently prepared by direct chemical synthesis or by molecular techniques well known to one of skill in the art. For example, amino acid sequence variants of a TCR V peptide can be prepare by mutations in the nucleic acid encoding the peptide. Such variants include, for example, deletions from, or insertions or substitutions of, residues within the amino acid sequence. However, a variant must not create complementary regions that provide secondary mRNA structure. Suitable variants are described in U.S. Pat. No. 5,614,192, which is incorporated herein by reference in its entirety.

In one specific, non-limiting example, the TCR V peptide is a "TCR V beta (β) peptide. In another specific, non-limiting example, the TCR peptide corresponds to the VDJ region of the TCR β chain or the V region of the TCR V α chain. In another embodiment, the peptide corresponds to at least part of one of the three complementarity determining regions (CDR) of the TCR heterodimer, such as the second CDR (CDR2). TCR V peptides are described below in the Examples section, and are also described in U.S. Pat. Nos. 5,614,192; 5,776,459; U.S. patent application Ser. No. 09/853,830, all of which are incorporated herein by reference in their entirety.

Transduced and Transformed: A virus or vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: In one embodiment a nucleic acid molecule as introduced into a host cell, thereby producing a transformed host cell. A vector may include nucleic acid sequences that permit it to replicate in the host cell, such as an origin of replication. A vector may also include one or more selectable marker genes and other genetic elements known in the art. In one embodiment the term "vector" includes viral vectors, such as adenoviruses, adeno-associated viruses, vaccinia, and retroviral vectors. In one embodiment the term vector includes bacterial vectors.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Method for Screening for TCR V Peptides

A method is disclosed herein for identifying a T cell receptor (TCR) variable (V) peptide of use as a therapeutic agent in a subject. In one embodiment, the subject has an autoimmune disease. A method is provided herein to screen TCR alpha chain peptides, TCR beta chain peptides, or both TCR alpha and TCR beta chain peptides to select a TCR V peptide of use in inducing the activity of regulatory T cells (Treg). Thus, using the screening methods provided herein, one of skill in the art can select a TCR V peptide that induces maximal Treg activity for use in a subject having an autoimmune disorder. These TCR V peptides can be utilized to produce an increase in Treg cells in the subject, such that Treg cells can be detected as a component of the peripheral blood mononuclear cells.

The method includes selecting a TCR V peptide that produces altered expression of a cytokine elicited in response to the TCR V peptide by T cells from the subject. The method also includes determining a regulatory activity of CD4+ T cells isolated from the subject elicited in response to the TCR V polypeptide. Generally, determining a regulatory activity is an assay that demonstrates the function of the cells. These assays can be performed simultaneously or sequentially, in any order.

The T cells of use in the assay can be derived from any convenient T cell source in the subject, such as lymphatic tissue, spleen cells, blood, cerebrospinal fluid (CSF) or synovial fluid. The T cells can be enriched, if desired, by standard positive and negative selection methods (see below). If enriched, the T cell population should retain a sufficient number of antigen-presenting cells to present the TCR peptide to the regulatory T cells. A convenient source of T cells to use in a cytokine assay are peripheral blood mononuclear cells (PBMC), which can be readily prepared from blood by density gradient separation, by leukapheresis or by other standard procedures known in the art.

TCR peptides are well known in the art (see for example, U.S. Pat. Nos. 5,614,192, 5,776,459; and U.S. patent application Ser. No. 09/853,830, all of which are incorporated by reference herein in their entirety). The TCR peptide can contain the complete V chain, or any immunogenic portion of the V region that is characteristic of the particular TCR V gene or gene family of interest. Such a peptide can have a sequence that is identical to that of the naturally occurring V chain. In one embodiment, a TCR V peptide includes one or more substitutions, such as a TCR V peptide that contains 1, 2 or several substitutions that do not alter its specificity for the TCR V gene or gene family of interest.

Useful TCR V peptides will generally be from about 8 to about 100 amino acids in length, such as from about 10 to about 50 amino acids, including from about 15 to about 30 amino acids. TCR V peptides having any amino acids sequence of interest can be prepared by methods known in the art, including chemical synthesis and recombinant methods.

The CDR2 region, which corresponds to amino acids 38-58 of alpha (A) V and beta (B) V chains, is a region that is characteristic of each TCR V chain. The amino acid sequences of peptides corresponding to amino acids 38-58 of each of the 116 known AV and BV chains are shown in Tables 2 and 3. Within a given family (e.g. BV6) or subfamily (e.g. BV6S1) of V chains, amino acids 38-58 generally differ at only one or several positions. Accordingly, if desired, a consensus CDR2 peptide can be prepared, which does not necessarily have the exact sequence of any naturally occurring V chain, but which stimulates T cells that are reactive against all members of the family or subfamily.

Appropriate TCR V peptides to use in the methods disclosed herein can be determined by those skilled in the art. The immunogenicity of a given peptide can be predicted using well-known algorithms that predict T cell epitopes (see, for example, Savoie et al., *Pac. Symp. Biocomput.* 1999:182-189, 1999; Cochlovius et al., *J. Immunol.* 165:4731-4741, 2000). Both the immunogenicity and the specificity of a given peptide can be confirmed by standard immunological assays that measure in vivo or in vitro T cell responses (e.g. T cell proliferation assays, delayed type hypersensitivity assays, ELISA assays, ELISPOT assays and the like).

In one specific, non-limiting example, T cells from the subject are contacted with a TCR V peptide of interest and the expression of a cytokine is detected. A variety of methods can be used to detect and quantitate cytokine expression by T cells. For example, an immunospot assay, such as the enzyme-linked immunospot or "ELISPOT" assay, can be used. The immunospot assay is a highly sensitive and quantitative assay for detecting cytokine secretion at the single cell level. Immunospot methods and applications are well known in the art and are described, for example in Czerkinsky et al., J. Immunol. Methods 110:29-36, 1988; Olsson et al. J. Clin. Invest. 86:981-985, 1990; and EP 957359.

In general, the immunospot assay uses microtiter plates containing membranes that are precoated with a capture agent, such as an anti-cytokine antibody, specific for the cytokine to be detected. T cells of interest are plated together with a test immunogen, which in the invention method is a TCR V peptide. The T cells that respond to the immunogen secrete various cytokines. As the cytokine of interest is locally released by the T cells, it is captured by the membrane-bound antibody. After a suitable period of time the cell culture is terminated, the T cells are removed and the plate-bound cytokine is visualized by an appropriate detection system. Each cytokine-secreting T cell will ideally be represented as a detectable spot. The number of spots, and thus the number of T cells secreting the particular cytokine of interest, can be counted manually (e.g. by visualization by light microscopy) or by using an automated scanning system (e.g. an Immunospot Reader from Cellular Technology Ltd.). Examples I and II describe the use of an ELISPOT assay to quantitate and compare the number of regulatory T cells that secrete IL-10 (and/or IFN-γ) in response to different TCR V peptides in different individuals.

Variations of the standard immunospot assay are well known in the art and can be used to detect cytokine secretion in the methods of the invention. For example, U.S. Pat. No. 6,218,132 describes a modified immunospot assay in which antigen-responsive T cells are allowed to proliferate in response to stimulation with the immunogen before detection of the cytokine of interest. This method, although more time-consuming, can be used to increase the sensitivity of the assay for detecting T cells present at a low frequency in the starting population.

U.S. Pat. No. 5,939,281 describes an improved immunospot assay that uses a hydrophobic membrane instead of the conventional nitrocellulose membrane, to bind the cytokine capture reagent. This variation can be used to reduce the nonspecific background and increase the sensitivity of the assay. Other modifications to the standard immunospot assay that increase the speed of processing multiple samples, decrease the amount of reagents and T cells needed in the assay, or increase the sensitivity or reliability of the assay, are contemplated herein and can be determined by those skilled in the art.

Antibodies suitable for use in immunospot assays, which are specific for secreted cytokines, as well as detection reagents and automated detection systems, are well known in the art and generally are commercially available. Appropriate detection reagents are also well known in the art and commercially available, and include, for example, secondary antibodies conjugated to fluorochromes, colored beads, and enzymes whose substrates can be converted to colored products (e.g., horseradish peroxidase and alkaline phosphatase). Other suitable detection reagents include secondary agents conjugated to ligands (e.g. biotin) that can be detected with a tertiary reagent (e.g. streptaviden) that is detectably labeled as above.

Other methods for detecting and quantifying cytokine expression by T cells are well known in the art, and can be used as an alternative to immunospot assays in the methods of the invention. Such methods include the ELISA assay, which can be used to measure the amount of cytokine secreted by T cells into a supernatant (see, for example, Vandenbark et al., Nature Med. 2:1109-1115, 1996). Alternatively, the expression of cytokine mRNA can be determined by standard immunological methods, which include RT-PCR and in-situ hybridization.

In one embodiment, the assay for expression of a cytokine involves an initial comparison between cytokine expression in response to a TCR V peptide in a test subject and a normal value for the same regulatory activity. The normal value can be a value obtained from a single healthy control individual, or can be an average of values obtained from a number of healthy control individuals. Suitable healthy control individuals can be identified by one of skill in the art, but generally will be appropriately matched for age, gender and other variables that can affect immunological activity. In one specific, non-limiting example, the control is one or more individuals of the same relative age and sex, but these individuals do not have an autoimmune disease. The normal value for cytokine expression can be determined at the same time, prior to or after assaying for cytokine expression in the test individual.

As used herein, the term "low" or "reduced" or "decreased" with respect to cytokine expression refers to an activity that is significantly reduced in a test individual compared to the normal value for that activity. The extent of reduction required for significance will vary depending on the sensitivity and reproducibility of the method, but will generally be at least 25% lower than a normal value obtained for the same activity or response, such as at least 40%, 50%, 70%, 80% or 90% lower than the normal value. The term "low" also includes a complete absence of detectable activity, as evidenced by a background level of activity. Thus, in one embodiment, a TCR V beta peptide is identified that induces reduced expression of a cytokine in a subject with an autoimmune disorder as compared to a control.

As used herein, the term "high" or "increased" with respect to cytokine expression refers to an activity that is significantly increased in a test individual compared to the normal value for that activity. The extent of increase required for significance will vary depending on the sensitivity and reproducibility of the method, but will generally be at least 25% higher than a normal value obtained for the same activity or response, such as at least 40%, 50%, 70%, 80% or 90% higher than the normal value. Thus, in one embodiment, a TCR V beta peptide is identified that induces increased expression of a cytokine in a subject with an autoimmune disorder as compared to a control.

The method further includes an assay to identify a TCR V peptide that induces regulatory T cell (Treg) activity in T cell isolated from the subject. Treg activity can be assayed by any means known to one of skill in the art. Generally, an assay for Treg activity is an assay that demonstrates a function of the T cells. In one specific, non-limiting example, CD4+ T cells are isolated from a subject, and used to assay Treg activity.

Method for isolated CD4+, CD4+CD25+ T cells, CD4+ CD25− T cells, or other populations of T cells, are well known in the art. Typically, labeled antibodies specifically directed to the marker are used to identify the cell population. The antibodies can be conjugated to other compounds including, but not limited to, enzymes, magnetic beads, colloidal magnetic beads, haptens, fluorochromes, metal compounds, radioactive compounds or drugs. The enzymes that can be conjugated to the antibodies include, but are not limited to, alkaline phosphatase, peroxidase, urease and β-galactosidase. The fluorochromes that can be conjugated to the antibodies include, but are not limited to, fluorescein isothiocyanate, tetramethylrhodamine isothiocyanate, phycoerythrin, allophycocyanins and Texas Red. For additional fluorochromes that can be conjugated to antibodies see Haugland, R. P., Molecular Probes: Handbook of Fluorescent Probes and Research Chemicals (1992-1994). The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxigenin, oxazalone, and nitrophenol. The radioactive compounds that can be conjugated or incorporated into the antibodies are known to the art, and include but are not limited to technetium 99m ($^{99}$Tc), $^{125}$I and amino acids comprising any radionuclides, including, but not limited to, $^{14}$C, $^{3}$H and $^{35}$S.

Fluorescence activated cell sorting (FACS) can be used to sort cells that express CD4, CD25, or both CD4 and CD25, by contacting the cells with an appropriately labeled antibody (e.g., see Example 12). However, other techniques of differing efficacy may be employed to purify and isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

Separation procedures may include magnetic separation, using antibody-coated magnetic beads, affinity chromatography, cytotoxic agents, either joined to a monoclonal antibody or used in conjunction with complement, and "panning," which utilizes a monoclonal antibody attached to a solid matrix, or another convenient technique. Antibodies attached to magnetic beads and other solid matrices, such as agarose beads, polystyrene beads, hollow fiber membranes and plastic petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well within the skill in the art.

The unbound cells then can be eluted or washed away with physiologic buffer after sufficient time has been allowed for the cells expressing a marker of interest (e.g. CD4 and/or) to bind to the solid-phase linked antibodies. The bound cells are then separated from the solid phase by any appropriate method, depending mainly upon the nature of the solid phase and the antibody employed.

Antibodies may be conjugated to biotin, which then can be removed with avidin or streptavidin bound to a support, or fluorochromes, which can be used with a fluorescence activated cell sorter (FACS), to enable cell separation, as known in the art.

In one embodiment, CD4$^+$ T cells are contacted with the TCR V peptide of interest to produce regulatory CD4+ CD25+ T cells. The regulatory CD4+CD25+ are then contacted with CD4+CD25− responder cells. Thus, in one specific, non-limiting example, the assay for Treg activity requires cell-to cell-contact. In one embodiment, the CD4+ CD25− cells are isolated from the same subject as the CD4+ CD25+ cells. In another embodiment, the CD4+CD25− cells are isolated from a different subject than CD4+CD25+ cells. These cells are further contacted with an agent that induces proliferation. In one embodiment, the agent that induces proliferation activates the T cell through the T cell receptor. In one specific, non-limiting example the agent that induces proliferation is an antibody that specifically binds CD3 and an antibody that specifically binds CD28. In another specific non-limiting example, the agent that induces proliferation is a specific antigen. In yet another specific non-limiting example, the agent that induces proliferation is concavalin A (ConA).

Proliferation is then assessed. One of skill in the art can readily identify suitable assays for proliferation. These assays include, but are not limited to, assays for $^{3}$H-thymidine uptake, assays for bromodeoxyuridine uptake, and assays determining cell number. In one embodiment, an assay to detect cytokine release is utilized. Thus, a functional assay is performed.

In one embodiment, Treg activity is indicated by reduced proliferation of CD4+CD25− responder cells in the presence of graded doses of CD4+CD25+ T cells, when stimulated with agents that induce proliferation as compared to control CD4+CD25− T cells that exhibit full proliferation response. In one specific, non-limiting example, a dose response curve is generated. Typically, the CD4+CD25+ cells do not proliferate well to the same stimulus, although these T cells may become activated to exert Treg activity by anti-CD3/CD28 or specific antigens such as TCR peptides.

Changes in T cell regulatory activity in a single individual can be monitored over time to determine development or progression of an autoimmune disease, to monitor the efficacy of a therapy in restoring normal regulatory activity, or to determine an appropriate time to initiate, stop or readminister a therapy to boost regulatory activity. In performing such comparative assays, T cell samples obtained at various times can be frozen, and multiple assays performed simultaneously to minimize experimental variables. Assays can also be repeated several times and values averaged to increase the significance of observed differences.

In one embodiment, the T Cell Receptor Variable (TCR V) gene usage by target T cells in the subject is assayed. Thus, the expression of a TCR V genes by activated T cells from the subject is determined, and a TCR that is preferentially expressed is identified.

Without being bound by theory, one component of the mechanism underlying autoimmune disease is unregulated expansion of autoreactive T cells. These T cells have escaped normal regulation by V-specific regulatory T cells, and will preferentially express a corresponding V gene or limited set of V genes.

As used herein, the term "preferentially expressed" indicates that the particular TCR gene is expressed at a significantly higher level among activated T cells in an individual than among unselected T cells from the same individual. The term "unselected T cells" encompasses any T cell population that has not been preselected for activated T cells, or which is not expected to be enriched (in comparison with PBMCs) for activated T cells. Exemplary populations of unselected T cells include, for example, peripheral blood mononuclear cells and CD4+ enriched blood cells. The level of enhanced TCR V gene expression required for significance, and thus for "preferential expression," will vary depending on the sensitivity and reproducibility of the method, but will generally be at least a 20% increase, such as a 30%, 40%, 50%, 75%, 100% or greater increase in expression in the activated population than in the unselected T cell population.

Activated T cells are CD4+ T cells that have undergone characteristic phenotypic and functional changes as a result of interacting with antigen presented in the context of class II MHC. Such phenotypic and functional changes can include, for example, expression of activation surface markers, secretion of Th1 cytokines, and proliferation.

Activation surface markers include CD25 (which is the IL-2 receptor) CD134 (OX-40), which is a cell surface glycoprotein in the tumor necrosis factor receptor family, as well as CD30, CD27, HLA-DR, and CD69. The structural and functional properties of T cell activation surface markers, as well as reagents suitable for detecting such markers, are well known in the art (see, for example, Barclay et al., "The Leucocyte Antigen FactsBook," Academic Press, San Diego, Calif. (1993)).

Activated T cells can further express surface marker profiles characteristic of memory T cells, which include, for example, expression of CD45RO+ and lack of expression of CD45RA. Therefore, in one embodiment, the method in practiced by determining TCR V gene expression among activated, memory T cells.

Secreted cytokines that are characteristic of activated CD4+ T cells include, for example, interleukin-2 (IL-2), IL-4, IL-5, and γ-interferon (IFN-γ). The structural and functional properties of various cytokines, as well as reagents suitable for detecting cytokine expression and secretion, are well known in the art (see, for example, Thomson, ed., "The Cytokine Handbook," $2^{nd}$ ed., Academic Press Ltd., San Diego, Calif. (1994)).

A population of cells that contains activated T cells can be obtained from a variety of sources, including the peripheral blood, lymph, and the site of the pathology. The peripheral blood is generally the most convenient source of cells. However, appropriate pathological sites include the CNS (and particularly the cerebrospinal fluid) for multiple sclerosis and other autoimmune neurological disorders; the synovial fluid or synovial membrane for rheumatoid arthritis and other autoimmune arthritic disorders; and skin lesions for psoriasis, pemphigus vulgaris and other autoimmune skin disorders, any of which can be readily obtained from the individual. As available, biopsy samples of other affected tissues can be used as the source of T cells, such as intestinal tissues for autoimmune gastric and bowel disorders, thyroid for autoimmune thyroid diseases, pancreatic tissue for diabetes, and the like.

The cell population need not be pure, or even highly enriched for activated T cells, so long as the method allows for a comparison of TCR gene expression by activated and unselected T cells. For example, by FACS analysis the expression of both an activation surface marker and a V chain polypeptide can be detected simultaneously, without enrichment for activated T cells, and the number of activated and non-activated (or total) T cells expressing the V chain compared.

Depending on the assay method, it may be desirable to start with a cell population that is partially enriched, or highly enriched, for activated T cells. Methods for enriching for desired T cell types are well known in the art, and include positive selection for the desired cells, negative selection to remove undesired cells, and combinations of both methods.

Enrichment methods are conveniently performed by first contacting the cell population with a binding agent specific for a particular T cell surface activation marker or combination of markers. Appropriate binding agents include polyclonal and monoclonal antibodies, which can be labeled with a detectable moiety, such as a fluorescent or magnetic moiety, or with biotin or other ligand. If desired, the T cells can be further contacted with a labeled secondary binding agent specific for the primary binding agent. The bound cells can then be detected, and either collected or discarded, using a method appropriate for the particular binding agent, such as a fluorescence activated cell sorter (FACS), an immunomagnetic cell separator, or an affinity column (e.g. an avidin column or a Protein G column). Other methods of enriching cells by positive and negative selection are well known in the art.

Analogous methods have recently been developed for enriching for cells that secrete activation cytokines. In such methods a bivalent binding agent (e.g. a bivalent antibody) with specificity for both the secreted molecule and a cell surface molecule are allowed to contact the T cells. The secreted molecule, now relocated to the affinity matrix, is then contacted with a binding agent and bound cells sorted or separate by standard methods (see, for example, WO 99/58977 and Brosterhaus et al., Eur. J. Immunol., 29:4053-4059, 1999).

TCR V gene expression by the selected or unselected T cell population can be determined by a variety of methods. For example, such methods can be based on detection and quantification of expressed TCR V polypeptide chains, TCR V gene transcripts, or rearranged V genes.

Detection and quantification of V polypeptide expression can be practiced using agents that specifically bind particular V polypeptides, such as anti-V chain antibodies. Antibodies specific for a variety of Vα, Vβ, Vδ, and Vγ chains are available in the art (see, for example, Kay et al., Leuk. Lymphoma 33:127-133, 1999; Mancia et al., Scand. J. Immunol. 48:443-449, 1998). Alternatively, suitable polyclonal or monoclonal antibodies can be prepared by standard methods (see, for example, Harlow and Lane, Antibodies: A laboratory manual (Cold Spring Harbor Laboratory Press 1988); Ausubel et al., Current Protocols in Molecular Biology, John Wiley and Sons, Baltimore, Md. (2001)), starting from a V chain peptide.

Methods of detecting V polypeptide expression can be practiced using either whole cells or cell extracts. For example, whole cells can be contacted with appropriate detectably labeled antibodies and/or detectably labeled secondary antibodies. Cells that specifically bind the particular anti-V antibody are then detected and quantified by standard methods appropriate for the particular detectable label, such as FACS or immunofluorescence microscopy for fluorescently labeled molecules, scintillation counting for radioactively labeled molecules, and the like. Alternatively, cell extracts can be contacted with appropriate anti-V antibodies, and V polypeptide expression analyzed using standard methods, such as immunoprecipitation, immunoblotting or ELISA (see, for example, Ausubel et al., Current Protocols in Molecular Biology, John Wiley and Sons, Baltimore, Md. (2001)).

Methods for detecting and quantifying TCR V gene transcripts or rearranged V genes generally involve specific hybridization of nucleic acid probes or primers to mRNA, cDNA, or genomic DNA, as appropriate, from the T cells of interest. The nucleotide sequences of Vα, Vβ, Vδ, and Vγ genes are well known in the art (see, for example, Genevee et al., Eur. J. Immunol. 22:1261-1269, 1992; Arden et al., Immunogenetics 42:455-500, 1995; Choi et al., Proc. Natl. Acad. Sci. USA 86:8941-8945, 1989; Concannon et al., Proc. Natl. Acad. Sci. USA 83:6598-6602, 1986; Kimura et al., Eur. J. Immunol. 17:375-383, 1987; Robinson, J. Immunol. 146: 4392-4397, 1991; and the EMBL alignment database under alignment accession number DS23485). Therefore, the skilled person can readily prepare probes and primers specific for any TCR V gene of interest, appropriate for the particular detection method.

Exemplary detection methods include, for example, reverse-transcriptase polymerase chain reaction (RT-PCR), Northern blots, RNase protection assays, in situ hybridization, and the like. Detection methods can conveniently employ radiolabeled or fluorescently labeled nucleotides, such that the amount of hybridization or amount of amplified product can be detected by a commercially available phosphorimaging apparatus. Suitable methods for detecting and quantitating mRNA expression are described, for example, in Ausubel et al., supra (2001) and other standard molecular biology manuals.

Automated assays for simultaneously detecting and quantitating expression of a plurality of genes are also well known in the art, and are contemplated herein for determining V gene expression. For example, nucleic acid molecules specific for all or a particular subset of V genes can be attached to a solid support, such as a plate, slide, chip or bead, which can then be contacted with the appropriate T cells, T cell extracts, or T cell nucleic acid molecules, under suitable hybridization conditions, and processed automatically by standard methods. Likewise, immunological assays for simultaneously detecting expression of a plurality of polypeptides are well known in the art. Such methods generally involve the use of a plurality of different antibodies bound to a solid support, and binding can be detected by automated detection systems.

Thus, in one embodiment, a preferentially expressed TCR V gene is identified, and TCR V peptides corresponding to the TCR V gene are selected. TCR V peptides corresponding to the preferentially expressed TCR V gene are then used to in a assay of the T cells of the subject of interest, such as a functional assay. The TCR V peptides corresponding to the preferentially expressed V gene are used to assay the expression of a cytokine elicited in response to one or more TCR V peptides, and are used to determine if the TCR V peptides induce Treg activity. Thus, using the methods disclosed herein, the TCR V peptides that are not recognized well in a subject with an autoimmune disorder, or that are recognized well but can be amplified by vaccination, are identified.

The methods disclosed herein are illustrated by the following non-limiting Examples.

EXAMPLES

Example 1

Material and Methods

Patients. Study participants included MS patients (ages 24-74) with definite relapsing-remitting or progressive MS, and healthy controls (HC, ages 23-55). MS patients had diagnosed MS for 2-30 years, and were currently not receiving Avonex™, Betaseron™, Copaxone™, or corticosteroids. Blood samples were obtained from the MS clinic after obtaining informed consent.

TCR V gene expression. Peripheral blood mononuclear cells (PBMCs) were obtained and enriched for CD4+ T cells by removal of B cells, monocytes, NK cells and CD8+ T cells using antibody-coated magnetic beads. These cells were then stained with fluorescent mAb specific for CD4, activation (CD25), and naive (CD45RA) T cell markers. CD4+cells were gated and sorted by FACS to obtain activated memory T cells (CD25+, CD45RA−), as well as non-activated naive T cells (CD25−, CD45RA+). mRNA was prepared from the CD4+ starting population, activated memory cells, and resting naive T cells, and evaluated for V gene expression by RT-PCR, essentially as described in Chou et al., *J. Immunol.* 152:2520-2529, 1994, using BV gene specific primers.

Briefly, total RNA was isolated from fresh pelleted cells using the Stratagene RNA Isolation Kit (Stratagene, La Jolla, Calif.). cDNA was synthesized in a 20 µl volume using Superscript II reverse transcriptase (Life Technologies, Rockville, Md.) and an oligo(dT)12-18primer (Life Technologies, Rockville, Md.) following the manufacturer's recommendations. For amplification of TCRBV cDNA, a panel of 26 BV and a single BC primer was used. A portion of the BC primer was labeled (either 2 to 3% was radioactively labeled with $^{32}$P-ATP, or 50% was end labeled at the 5' end with the fluorochrome, Cy3 (Amersham Pharmacia Biotech, Piscataway, N.J.). As a positive control for the reaction, two BC primers (forward and reverse) were used, and the reverse primer was labeled as above. The cDNA from 1500 to 2000 T cells was used in each 15 µl reaction, along with 0.3 µl of each primer, 0.5U Taq DNA polymerase (Promega, Madison, Wis.), 50 mM KCl, 10 mM Tris-HCl (pH 9), 0.1% Triton X-100, 0.2 mM dNTPs, and 2 mM MgCl2. Amplification was carried out for 24-26 cycles (94.5 C×30 seconds, 60 C×1 minute, 72 C×1 minute), followed by a final 5 minutes extension at 72 C. All PCR reactions were performed in a Perkin Elmer GeneAmp 9600 thermocycler (Perkin-Elmer, Norfolk, Conn.).

For the amplification of TCRAV cDNA, a panel of 30 AV primers and a AC primer were used (the AC primer was partially labeled as above). As a positive control for the reactions, two AC primers (forward and reverse) were used, one labeled as above. PCR conditions were as described above. Following amplification, 10 µl of each reaction was loaded on a 6% polyacrylamide gel and run at 250V for 22 minutes. If the DNA was radioactively labeled, the gel was dried for one hour, exposed to a phosphor screen for 30 minutes to hour, and analyzed by phosphor imaging (BioRad Molecular Imager FX, BioRad, Hercules, Calif.). If the DNA was fluorescently labeled, the gel was directly imaged on a fluorescent imager (BioRad Molecular Imager FX, BioRad, Hercules, Calif.). In either case, the PCR products of the correct size were quantitated by measuring phosphor or fluorescent signal intensity, and the background subtracted using an adjacent region below the bands.

Antigens. Antigens used in the ELISPOT assay included ConA (2 µg/ml) and synthetic TCR peptides (25 µg/ml), including 116 known AV and BV gene products.

T cell frequency. To determine antigen-specific T cell frequency by ELISPOT, blood mononuclear cells were separated by Ficoll density gradient centrifugation, resuspended in 2% human AB serum, and aliquotted at 0.5 and 0.25 million cells in triplicate wells of nitrocellulose-coated microtiter plates (Resolution Technologies) pretreated with anti-IFN-γ (Mabtech, Sweden) or anti-IL-10 (PharMingen, San Diego, Calif.) mAb. Peptides, ConA, and medium were added and the plates incubated at 37 C for 24 hours (IFN-γ) or 48 hours (IL-10). Biotin-labeled secondary mAb for each cytokine was added, followed by streptavidin-alkaline phosphatase (Dako Corp., Carpinteria, Calif.) and substrate (BCIP/NBT phosphatase substrate, KPL, Gaithersburg, Md.) to develop optimal blue staining. Cytokine spots were quantified using an AID Immunospot Analyzer (AID, Cleveland, Ohio) equipped with a high resolution lens camera and analytical software designed for use with the AID system. Mean spots/well were calculated for each Ag, and net counts established after subtraction of background (no Ag). The frequency of Ag-specific spot-forming cells per million PBMC was determined from the average net response observed at two different cell concentrations. The mean net frequency+SEM was calculated for MS patients and HC, and differences compared by Student's t test for significance ($p<0.05$).

Preparation of ELISPOT plates. Four flat bottom 96 well plates with nitrocellulose membranes were coated overnight with 4 µg/ml mouse anti-IL-10 monoclonal antibodies (Pharmingen), and an additional 4 plates were coated with 10 µg/ml mouse anti-human INF((Mabtech). Two hours before addition of peptides, plates were washed 3× with sterile PBS, pH 7.2, and blocked for one hour at room temperature with 10% FBS in sterile PBS.

Blood processing. Twelve tubes of blood (approximately 120 ml) were collected from healthy controls and MS patients. The blood was immediately separated over a Ficoll gradient by centrifugation for 25 minutes at 2100 rpm at 25 degrees. Peripheral blood mononuclear cells (PBMC) so obtained were washed 3× with cold RPMI and resuspended to $10 \times 10^6$ cells per ml.

TCR peptide screens. Sterile stocks containing 1 mg/ml peptide were aliquotted among 4 sterile 96 well polypropylene blocks. Blocks were kept refrigerated for up to one month. Precoated and blocked ELIPSOT plates were washed with 1× with blocking solution and 100 µl of stimulation medium was added (5% fetal bovine serum/1% human AB serum/2 mM pyruvate, 2 mM glutamate, and 50 µg/ml penicillin/streptomycin). 10 µl of each peptide was added per well in triplicate wells. The sequence of each Vα (AV) peptide is shown in Table 2, and the sequence of each Vβ (BV) peptide is shown in Table 2. Negative control wells contained RPMI, positive control wells contained 2 µg/ml final concentration ConA. To each well human PBMC were added at a density of $2.5 \times 10^5$ cells per well in a total of 8 plates ($200 \times 10^6$ cells per well). Plates were incubated for 24 hours for INF-γ ELISPOTs and for 48 hours for IL-10 ELISPOTs.

TABLE 1

| Name | Amino Acid Sequence | SEQ ID NO: |
|---|---|---|
| AV1S1 | YPGQHLQLLLKYFSGDPLVKG | 1 |
| AV1S2A1N1T | YPNQGLQLLLKYTSAATLVKG | 2 |
| AV1S2A4T | YPNQGLQLLLKYTTGATLVKG | 3 |
| AV1S2A5T | YPNQGLQLLLKYTSAATLVKG | 4 |
| AV1S3A1T | YPNQGLQLLLKYLSGSTLVES | 5 |
| AV1S3A2T | YPNQGLQLLLKYLSGSTLVKG | 6 |
| AV1S4A1N1T | SPGQGLQLLLKYFSGDTLVQG | 7 |
| AV1S5 | HPNKGLQLLLKYTSAATLVKG | 8 |
| AV2S1A1 | YSGKSPELIMFIYSNGDKEDG | 9 |
| AV2S1A2 | YSGKSPELIMSIYSNGDKEDG | 10 |
| AV2S2A1T | YSRKGPELLMYTYSSGNKEDG | 11 |
| AV2S2A2T | YSRIGPELLMYTYSSGNKEDG | 12 |
| AV2S3A1T | DCRKEPKLLMSVYSSGNEDGR | 13 |
| AV3S1 | NSGRGLVHLILIRSNEREKHS | 14 |
| AV4S1 | LPSQGPEYVIHGLTSNVNNRM | 15 |
| AV4S2A1T | IHSQGPQYIIHGLKNNETNEM | 16 |
| AV4S2A3T | IHSQGPQNIIHGLKNNETNEM | 17 |
| AV5S1 | DPGRGPVFLLLIRENEKERK | 18 |
| ADV6S1A1N1 | SSGEMIFLIYQGSYDQQNATE | 19 |
| AV6S1A2N1 | SSGEMIFLIYQGSYDEQNATE | 20 |
| AV7S1A1 | HDGGAPTFLSYNALDGLEETG | 21 |
| AV7S1A2 | HDGGAPTFLSYNGLDGLEETG | 22 |
| AV7S2 | HAGEAPTFLSYNVLDGLEEKG | 23 |
| AV8S1A1 | ELGKRPQLIIDIRSNVGEKKD | 24 |
| AV8S1A2 | ELGKGPQLIIDIRSNVGEKKD | 25 |
| AV8S2A1N1T | ESGKGPQFIIDIRSNMDKRQG | 26 |

TABLE 1-continued

| Name | Amino Acid Sequence | SEQ ID NO: |
|---|---|---|
| AV9S1 | YSRQRLQLLLRHISRESIKGF | 27 |
| AV10S1A1 | EPGEGPVLLVTVVTGGEVKKL | 28 |
| AV11S1A1T | FPGCAPRLLVKGSKPSQQGRY | 29 |
| AV12S1 | PPSGELVFLIRRNSFDEQNEI | 30 |
| AV13S1 | NPWGQLINLFYIPSGTKQNGR | 31 |
| ADV14S1 | PPSRQMILVIRQEAYKQQNAT | 32 |
| AV15S1 | EPGAGLQLLTYIFSNMDMKQD | 33 |
| AV16S1A1T | YPNRGLQFLLKYITGDNLVKG | 34 |
| ADV17S1A1T | FPGKGPALLIAIRPDVSEKKE | 35 |
| AV18S1 | ETAKTPEALFVMTLNGDEKKK | 36 |
| AV19S1 | HPGGGIVSLFMLSSGKKKHGR | 37 |
| AV20S1 | FPSQGPRFIIQGYKTKVTNEV | 38 |
| AV21S1A1N1 | YPAEGPTFLSISSSIKDKNED | 39 |
| AV22S1A1N1T | YPGEGLQLLLKATKADDKGSN | 40 |
| AV23S1 | DPGKGLTSLLLIQSSQREQTS | 41 |
| AV24S1 | DTGRGPVSLTIMTFSENTKSN | 42 |
| AV25S1 | DPGEGPVLLIALYKAGELTSN | 43 |
| AV26S1 | KYGEGLIFLMMLQKGGEEKSH | 44 |
| AV27S1 | DPGKSLESLFVLLSNGAVKQE | 45 |
| AV28S1A1T | QEKKAPTFLFMLTSSGIEKKS | 46 |
| AV29S1A1T | KHGEAPVFLMILLKGGEQMRR | 47 |
| AV29S1A2T | KHGEAPVFLMILLKGGEQKGH | 48 |
| AV30S1A1T | DPGKGPEFLFTLYSAGEEKEK | 49 |
| AV31S1 | YPSKPLQLLQRETMENSKNFG | 50 |
| AV32S1 | RPGGHPVFLIQLVKSGEVKKQ | 51 |

TABLE 2

| Name | Amino Acid Sequence | SEQ ID NO: |
|---|---|---|
| BV1S1A1N1 | SLDQGLQFLIQYYNGEERAKG | 52 |
| BV1S1A2 | SLDQGLQFLIHYYNGEERAKG | 53 |
| BV2S1A1 | FPKQSLMLMATSNEGSKATYE | 54 |
| BV2S1A3N1 | FPKKSLMLMATSNEGSKATYE | 55 |
| BV2S1A4T | FPKQSLMLMATSNEGCKATYE | 56 |
| BV2S1A5T | FPKKSLMQIATSNEGSKATYE | 57 |
| BV3S1 | DPGLGLRLIYFSYDVKMKEKG | 58 |
| BV4S1A1T | QPGQSLTLIATANQGSEATYE | 59 |
| BV5S1A1T | TPGQGLQFLFEYFSETQRNKG | 60 |
| BV5S1A2T | TLGQGLQFLFEYFSETQRNKG | 61 |

TABLE 2-continued

| Name | Amino Acid Sequence | SEQ ID NO: |
|---|---|---|
| BV5S2 | ALGQGPQFIFQYYEEEERQRG | 62 |
| BV5S3A1T | VLGQGPQFIFQYYEKEERGRG | 63 |
| BV5S4A1T | ALGLGLQLLLWYDEGEERNRG | 64 |
| BV5S4A2T | ALGLGLQFLLWYDEGEERNRG | 65 |
| BV5S6A1T | ALGQGPQFIFQYYREEENGRG | 66 |
| BV6S1A1N1 | SLGQGPEFLIYFQGTGAADDS | 67 |
| BV6S1A3T | SLGQGPELLIYFQGTGAADDS | 68 |
| BV6S2A1N1T | ALGQGPEFLTYFQNEAQLDKS | 69 |
| BV6S3A1N1 | ALGQGPEFLTYFNYEAQQDKS | 70 |
| BV6S4A1 | TLGQGPEFLTYFQNEAQLEKS | 71 |
| BV6S4A4T | NPGQGPEFLTYFQNEAQLEKS | 72 |
| BV6S5A1N1 | SLGQGLEFLIYFQGNSAPDKS | 73 |
| BV6S6A1T | ALGQGPEFLTYFNYEAQPDKS | 74 |
| BV6S8A2T | TLGQGSEVLTYSQSDAQRDKS | 75 |
| BV7S1A1N1T | KAKKPPELMFVYSYEKLSINE | 76 |
| BV7S2A1N1T | SAKKPLELMFVYSLEERVENN | 77 |
| BV7S3A1T | SAKKPLELMFVYNFKEQTENN | 78 |
| BV8S1 | TMMRGLELLIYFNNNVPIDDS | 79 |
| BV8S3 | TMMQGLELLAYFRNRAPLDDS | 80 |
| BV9S1A1T | DSKKFLKIMFSYNNKELIINE | 81 |
| BV10S1P | KLEEELKFLVYFQNEELIQKA | 82 |
| BV10S2O | TLEEELKFFIYFQNEEIIQKA | 83 |
| BV11S1A1T | DPGMELHLIHYSYGVNSTEKG | 84 |
| BV12S1A1N1 | DPGHGLRLIHYSYGVKDTDKG | 85 |
| BV12S2A1T | DLGHGLRLIHYSYGVQDTNKG | 86 |
| BV12S2A2T | DLGHGLRLIHYSYGVKDTNKG | 87 |
| BV12S2A3T | DLGHGLRLIHYSYGVHDTNKG | 88 |
| BV12S3 | DLGHGLRLIYYSAAADITDKG | 89 |
| BV13S1 | DPGMGLRLIHYSVGAGITDQG | 90 |
| BV13S2A1T | DPGMGLRLIHYSVGEGTTAKG | 91 |
| BV13S3 | DPGMGLRLIYYSASEGTTDKG | 92 |
| BV13S4 | DPGMGLRRIHYSVAAGITDKG | 93 |
| BV13S5 | DLGLGLRLIHYSNTAGTTGKG | 94 |
| BV13S6A1N1T | DPGMGLKLIYYSVGAGITDKG | 95 |
| BV13S7 | DPGMGLRLIYYSAAAGTTDKE | 96 |
| BV14S1 | DPGLGLRQIYYSMNVEVTDKG | 97 |
| BV15S1 | DPGLGLRLIYYSFDVKDINKG | 98 |
| BV16S1A1N1 | VMGKEIKFLLHFVKESKQDES | 99 |
| BV17S1A1T | DPGQGLRLIYYSQIVNDFQKG | 100 |
| BV17S1A2T | DPGQGLRLIYYSHIVNDFQKG | 101 |
| BV18S1 | LPEEGLKFMVYLQKENIIDES | 102 |
| BV19S1P | NQNKEFMLLISFQNEQVLQET | 103 |
| BV19S2O | NQNKEFMFLISFQNEQVLQEM | 104 |
| BV20S1A1N1 | AAGRGLQLLFYSVGIGQISSE | 105 |
| BV20S1A1N3T | AAGRGLQLLFYSIGIDQISSE | 106 |
| BV21S1 | ILGQGPELLVQFQDESVVDDS | 107 |
| BV21S2A1N2T | NLGQGPELLIRYENEEAVDDS | 108 |
| BV21S3A1T | ILGQGPKLLIQFQNNGVVDDS | 109 |
| BV22S1A1T | ILGQKVEFLVSFYNNEISEKS | 110 |
| BV23S1A1T | GPGQDPQFFISFYEKMQSDKG | 111 |
| BV23S1A2T | GPGQDPQFLISFYEKMQSDKG | 112 |
| BV24S1A1T | KSSQAPKLLFHYYNKDFNNEA | 113 |
| BV24S1A2T | KSSQAPKLLFHYYDKDFNNEA | 114 |
| BV25S1A1T | VLKNEFKFLISFQNENVFDET | 115 |
| BV25S1A3T | VLKNEFKFLVSFQNENVFDET | 116 |

Detection of cytokine producing cells. PBMC were removed from plates by washing with 3× with PBS and 3× with PBS/0.05% Tween, pH 7.6. To each well was added 100 μl of either anti-IFN-γ (1 μg/ml, Mabtech) or anti-IL-10 (2 μg/ml, Pharmingen) and incubated for 4 hours at room temperature in the dark. Plates were washed 4× with PBS/Tween, then 100 μl per well of alkaline-phosphatase-conjugated streptaviden (DAKO) (1:1000 of stock) was added and plates were incubated for 45 minutes at room temperature. Plates were washed 4× with PBS/Tween and 6× with PBS, 1 minute each. 100 μl of BCIP/NBT substrate (KPL laboratories) was added and the color reaction was allowed to develop for 3-7 minutes. Plates were rinsed 3× with distilled water and dried overnight at room temperature.

Analysis of ELISPOTS. Plates were scanned with an Immunospot Reader (Cellular Technology Limited) with optimized lighting conditions and analyzed according to the predetermined parameters of sensitivity, spot size, and background. The background counts were subtracted, and data was then normalized to cytokine secreting cells per million PBMC plated.

Analysis of TCR gene expression. mRNA is obtained from T cells as described in Example I, and TCR gene expression is determined by RT PCR using the AV primers set forth in Table 3 and the BV primers set forth in Table 4.

TABLE 3

| Name | Nucleotide Sequence (5' to 3') | SEQ ID NO: |
|---|---|---|
| AV1 | GGCATTAACGGTTTTGAGGCTGGA | 117 |
| AV2 | CAGTGTTCCAGAGGGAGCCATTGT | 118 |

TABLE 3-continued

| Name | Nucleotide Sequence (5' to 3') | SEQ ID NO: |
|---|---|---|
| AV3 | CCGGGCAGCAGACACTGCTTCTTA | 119 |
| AV4 | TTGGTATCGACAGCTTCACTCCCA | 120 |
| AV5 | CGGCCACCCTGACCTGCAACTATA | 121 |
| AV6 | TCCGCCAACCTTGTCATCTCCGCT | 122 |
| AV7 | GCAACATGCTGGCGGAGCACCCAC | 123 |
| AV8 | CATTCGTTCAAATGTGGGCAAAAG | 124 |
| AV8.1 | GTGAATGGAGAGAATGTGGAGC | 125 |
| AV8.2 | TGAGCAGAGGAGAGAGTGTGG | 126 |
| AV9 | CCAGTACTCCAGACAACGCCTGCA | 127 |
| AV10 | CACTGCGGCCCAGCCTGGTGATAC | 128 |
| AV11 | CGCTGCTCATCCTCCAGGTGCGGG | 129 |
| AV12 | TCGTCGGAACTCTTTTGATGAGCA | 130 |
| AV13 | TTCATCAAAACCCTTGGGGACAGC | 131 |
| AV14 | CCCAGCAGGCAGATGATTCTCGTT | 132 |
| AV15 | TTGCAGACACCGAGACTGGGGACT | 133 |
| AV16 | TCAACGTTGCTGAAGGGAATCCTC | 134 |
| AV17 | TGGGAAAGGCCGTGCATTATTGAT | 135 |
| AV18 | CAGCACCAATTTCACCTGCAGCTT | 136 |
| AV19 | ACACTGGCTGCAACAGCATCCAGG | 137 |
| AV20 | TCCCTGTTTATCCCTGCCGACAGA | 138 |
| AV21 | AGCAAAATTCACCATCCCTGAGCG | 139 |
| AV22 | CCTGAAAGCCACGAAGGCTGATGA | 140 |
| AV23 | TGCCTCGCTGGATAAATCATCAGG | 141 |
| AV24 | CTGGATGCAGACACAAAGCAGAGC | 142 |
| AV25 | TGGCTACGGTACAAGCCGGACCCT | 143 |
| AV26 | AGCGCAGCCATGCAGGCATGTACC | 144 |
| AV27 | AAGCCCGTCTCAGCACCCTCCACA | 145 |
| AV28 | TGGTTGTGCACGAGCGAGACACTG | 146 |
| AV29 | GAAGGGTGGAGAACAGATGCGTCG | 147 |
| AC (Sol'n.151) | AGAGTCTCTCAGCTGGTACA | 148 |
| AC (HCA23) | GTC TCT GAG CTG GTA CAG GG | 149 |
| AC (5') | GAACCCTGACCCTGCCGTGTACC | 150 |
| AC (3') | ATCATAAATTCGGGTAGGATCC | 151 |

TABLE 4

| Name | Nucleotide Sequence (5'-3') | SEQ ID NO: |
|---|---|---|
| BV1 | GCA CAA CAG TTC CCT GAC TTG CAC | 152 |
| BV2 | TCA TCA ACC ATG CAA GGG TGA CGT | 153 |
| BV3 | GTC TCT AGA GAG AAG AAG GAG CGC | 154 |
| BV4 | ACA TAT GAG AGT GGA TTT GTC ATT | 155 |
| BV5.1 | ATA CTT CAG TGA GAG ACA GAG AAA C | 156 |
| BV5.2.3 | TTC CCT AAC TAT AGC TCT GAG CTG | 157 |
| BV6.1.3 | AGG CCT GAG GGA TCC GTC TC | 158 |
| BV7 | CCT GAA TGC CCC AAC AGC TCT C | 159 |
| BV8 | ATT TAG TTT AAC AAC AAC GTT CCG | 160 |
| BV9 | CCT AAA TCT CCA GAC AAA GCT CAC | 161 |
| BV10 | CTC CAA AAA CTC ATC CTG TAC CTT | 162 |
| BV11 | TCA ACA GTC TCC AGA ATA AGG ACG | 163 |
| BV12 (B) | ACT GAC AAA GGA GAA GTC TCA GAT | 164 |
| BV13.1 (B) | CAC TGA CCA AGG AGA AGT CCC CAA T | 165 |
| BV13.2 (B) | GTG AGT TGG TGA GGG TAC AAC TGC C | 166 |
| BV14 | GTC TCT CGA AAA GAG AAG AGG AAT | 167 |
| BV15 | AGT GTC TCT CGA CAG GCA CAG GCT | 168 |
| BV16 | AAA GAG TCT AAA CAG GAT GAG TCC | 169 |
| BV17(B) | CTA CTC ACA GAT AGT AAA TGA CTT TCA G | 170 |
| BV18 | GAT GAG TCA GGA ATG CCA AAG GAA | 171 |
| BV19 | CAA TGC CCC AAG AAC GCA CCC TGC | 172 |
| BV20 | AGC TCT GAG GTG CCC CAG AAT CTC | 173 |
| BV21 (C) | TGT GGC TTT TTG GTG CAA TCC TAT | 174 |
| BV22 | GTT TTA TGA AAA GAT GCA GAG CGA | 175 |
| BV23 | ATA ATG AAA TCT CAG AGA AGT CTG | 176 |
| BV24 | GCA GAC ACC CCT GAT AAC TTC | 177 |
| BC (HCB-E) | CGT AGA ATT CGA CTT GAC AGC GGA AGT GGT | 178 |
| BC (H3CB5) | CTG CTT CTG ATG GCT CAA ACA C | 179 |
| BC (5') | CGCTGTCAAGTCCAGTTCTA | 180 |
| BC (3') | TCTCTTGACCATGGCCATCA | 181 |

Treg assay: CD4+CD25+ and CD4+CD25− T cells were separated from 100 ml blood and each subpopulation was stimulated with anti-CD3+ anti-CD28 mAbs alone or in mixed cultures containing a fixed number (10,000) of CD4+ CD25− responder cells and varying numbers of CD4+CD25+ T cells to give 0%, 20%, 33%, 50%, 67% and 100% in triplicate cultures (see FIG. 5). After 3 days, the cells were harvested and assessed for proliferation and cytokine production (IFN-γ and IL-10) in culture supernatants by ELISA. The endpoint of each Treg assay is to verify a dose-dependent inhibition of Th1 function and to calculate the percentage of CD4+CD25+ T cells that produces 50% inhibition ($I_{50}$) of each parameter (see FIG. 5).

Example 2

Natural Recognition of TCR Determinants in Healthy Control Donors

It has been shown that: 1) that peptides including CDR2 (residues 38-58 with a core epitope extending from residues 46-52) appear to be the most immunogenic region of both AV and BV proteins; 2) that injection of a modified (Y49T) BV5S2 peptide into MS patients can induce significantly increased frequencies of BV5S2-reactive T cells in about half of vaccinated patients, resulting in reduced response to MBP and a significant trend towards clinical benefit in patients with response to vaccination; 3) that TCR-specific T cells can be activated by target Th1 cells expressing the cognate TCR, presumably through expression of internally processed TCR chains associated with upregulated MHC Class II molecules, or by APC pulsed with the specific TCR peptide, but not by T cells expressing a different TCR; 4) that once activated by whole cells or specific peptides, the TCR-reactive T cells secrete soluble inhibitory factors, including IL-10, that can inhibit activation and cytokine secretion both by target and bystander Th1 cell (see U.S. patent application Ser. No. 09/853,830; Vandenbark et al., *J. Neurosci. Res.* 66:171-176, 2001, which are herein incorporated by reference in their entirety). These mechanisms account for the broader effects of vaccination observed with BV5S2 peptide than would be predicted solely on the basis of BV5S2 expression by MBP-specific T cells, which occurs in <25% of MBP-reactive T cell clones. In addition, data suggest that native T cell responses to BV5S2 and other V genes normally present in healthy controls are deficient in about half of the MS patients (Vandenbark et al., *J. Neurosci. Res.* 66:171-176, 2001).

Figure 2:
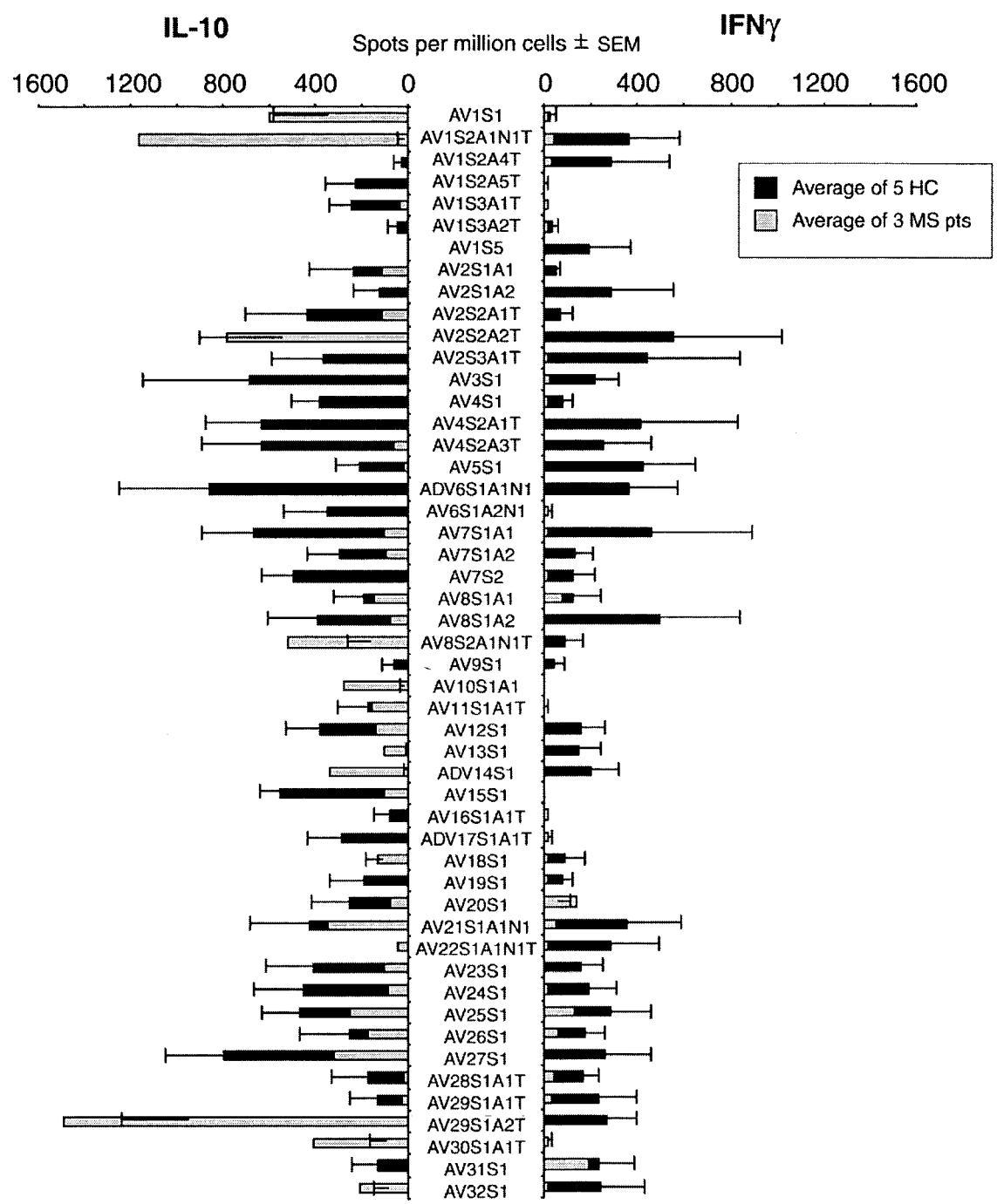
FIG. 2 is a bar graph showing cytokine production in response to AV CDR2 peptides. Solid bars represent mean frequencies per million PBMC±SEM of TCR AV specific IL-10 or IFN-γ-secreting cells (background subtracted) for 5 healthy controls. Superimposed gray bars represent mean frequencies for 2-3 MS patients (responses to only 15 AV peptides available in 1 patient). In some cases where mean frequency for MS donors is greater than HC (i.e. AV1S1), the solid bar is obscured, but the mean frequency for HC can be discerned by locating the origin of the error bar. Designations: A=beta chain; D=delta chain; V=variable region; AV1-32=family; S1-5=subfamily; A1-5=allele; N1-2=single nucleotide difference; T=tentative.
Figure 8:
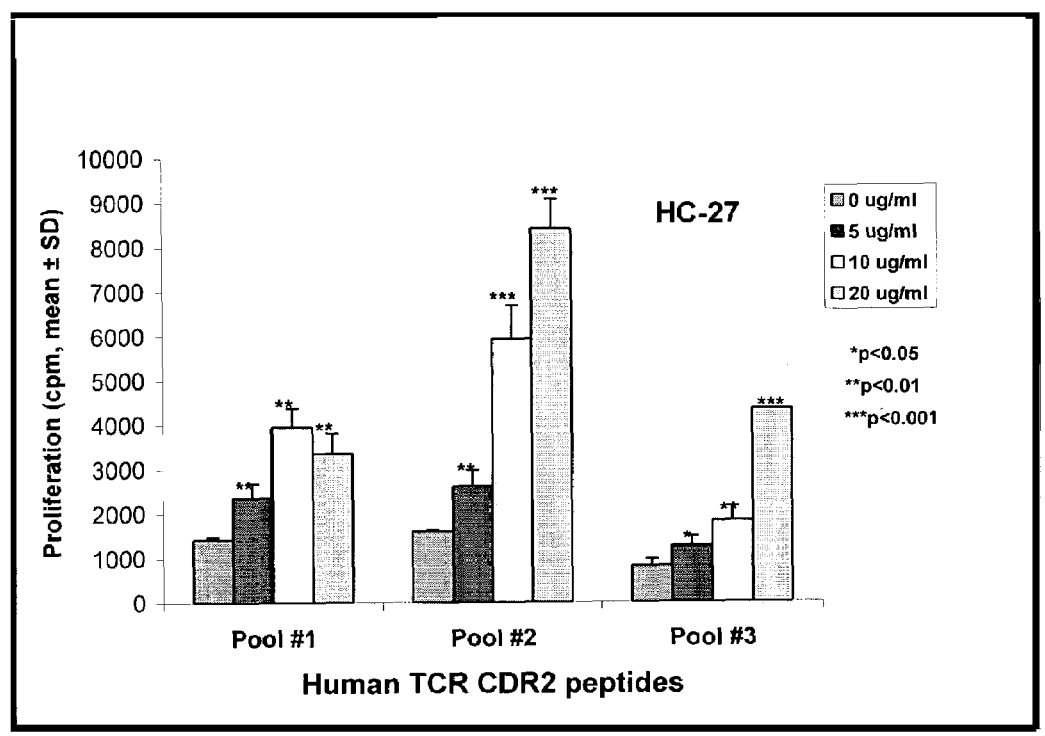
FIG. 8 is a bar graph showing proliferation response of T cell lines to pooled TCR CDR2 peptides from an HC donor. Proliferation response of T cell lines from an HC donor to 3 peptide pools as follows: Pool #1, IL-10-inducing 8 peptides (AV15S1, BV10S1P, BV11S1A1T, BV12S1A1N1, BV12S2A2T, BV13S7, BV19S20 and BV21S3A1T), Pool #2, IFN-g-inducing 3 peptides (ADV6S1A1N1, BV12S2A1T and BV12S2A2T), Pool #3, Proliferative 6 peptides (AV1S1, AV2S2A2T, AV29S1A2T, BV5S2A1T, BV7S1A1N1T and BV8S1). Pool 1 was chosen to discriminate IL-10 responses between MS patients and HC, Pool 2, to discriminate IFN-γ responses between MS patients and HC, and Pool 3 to induce proliferation responses in HC as well as MS patients. Note the proliferation inducing ability of all three pools.
Figure 9:
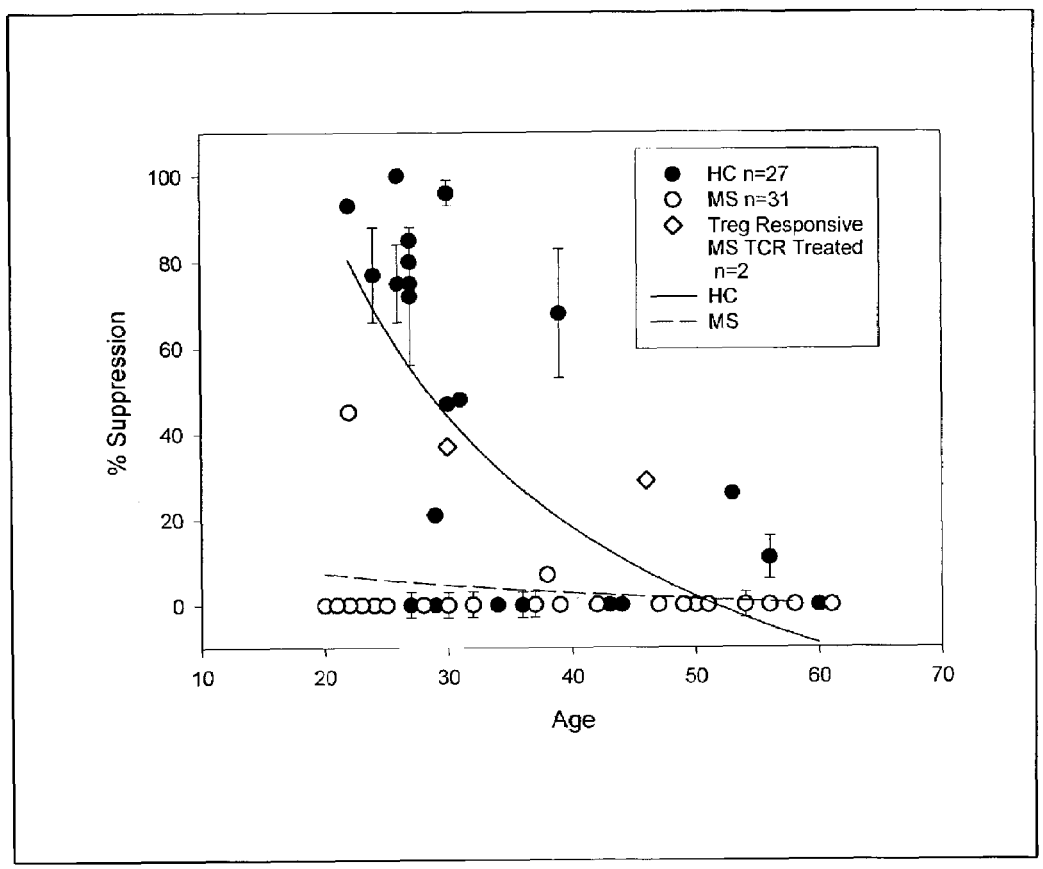
FIG. 9 is a line graph showing that Treg-induced suppression is absent or reduced in MS patients versus age-matched healthy controls (HC). Values indicate % suppression at the 1:2 ratio of CD4+CD25− indicator cells:CD4+CD25+ Treg cells obtained from MS and HC PBMC by bead sorting. Error bars indicate 2-6 repeat evaluations on indicated donors over a period of 1-12 months.

To evaluate native recognition of TCR determinants, the frequency of IL-10 and IFN-γ-secreting T cells from the blood of 5 healthy controls (3 females, 2 males, average age 28) was assessed using the ELISPOT assay to detect responses to a comprehensive panel of 113 unique CDR2 peptides representing nearly all of the AV and BV repertoires (see FIGS. 8 and 9 of Ref. (101), included in Appendix, for actual sequences). Only 3 peptides, AV1S4A1N1T, BV15S1 and BV20S1A1N1 could not be tested due to solubility and toxicity problems. As is shown in FIG. 1 (BV) and FIG. 2 (AV), peptide-specific T cells secreting either IL-10 or IFN-γ were detected in response to nearly all of the TCR peptides tested. Frequencies varied considerably from peptide to peptide and from donor to donor, but overall were not markedly different between males and females. It is noteworthy that the average frequency of IL-10-secreting T cells recognizing BV peptides was >600 cells/million PBMC, and for AV peptides, >300 cells/million. The most reactive IL-10-inducing BV peptide (>2000 cells/million PBMC) was BV10S1P (FIG. 1), a pseudogene presumed not to be present as a functional TCR, whereas the most reactive AV peptide (>1000 cells/million PBMC) was a rare AV29S1A2T allele (FIG. 2). Interestingly, BV10S1P induced minimal frequencies of IFN-γ-secreting cells, suggesting a strongly biased Th2 response. IFN-γ responses to TCR peptides were less vigorous than IL-10 responses, with an average frequency of 250 cells/million BV-reactive T cells and an average frequency of 182 cells/million AV-reactive T cells. The most reactive IFN-γ-inducing peptide (900 cells/million PBMC) was BV19S1P, another pseudogene. The strong recognition of relatively rare TCR sequences suggests an inverse correlation between TCR expression and TCR peptide recognition that may implicate TCR-reactive T cells as regulators of TCR repertoire formation, although it is yet unknown if both IL-10- and IFN-γ-secreting T cells possess regulatory function. As is shown in Table 5, total frequencies of IL-1 O-secreting T cells were higher than those of IFN-γ-secreting T cells for all 5 donors, and in most cases frequencies to BV peptides were higher than to AV peptides.

TABLE 5

IL-10 and IFN-γ Elispot frequencies to CDR2 peptides in Healthy Controls
(Numbers of cells per million PBMC producing cytokine in response to the CDR2 peptides):

|  | HC1 F age 25 | HC2 M age 37 | HC3 F age 25 | HC4 F age 23 | HC144 M age 29 | Average of 5 HC | SEM |
|---|---|---|---|---|---|---|---|
| IL-10 AV CDR2 Frequency | 8293 | 7817 | 19557 | 17444 | 22239 | 15070 | 3314 |
| IL-10 BV CDR2 Frequency | 26561 | 36729 | 53588 | 35529 | 40568 | 38595 | 4914 |
| Total IL-10 (AV + BV) CDR2 Frequency | 34855 | 44546 | 73145 | 52973 | 62807 | | |
| IFN-γ AV CDR2 Frequency | 9303 | 5091 | 20093 | 8878 | 2241 | 9121 | 3392 |
| IFN-γ BV CDR2 Frequency | 8933 | 6428 | 24712 | 31637 | 6777 | 15697 | 5845 |
| Total IFN-γ (AV + BV) CDR2 Frequency | 18236 | 11519 | 44805 | 40515 | 9018 | 24818 | 8351 |
| Total (AV + BV) Frequency | 53091 | 56065 | 117950 | 93488 | 71825 | 78484 | 13635 |

TABLE 6

IL-10 and IFN-γ ELISPOT frequencies to
CDR2 peptides in MS patients
(Numbers of cells per million PBMC producing
cytokine in response to the CDR2 peptides):

|  | MS193 (RR)* F age 42 (A) | MS74 (RR)* F age 61 (A) | MS186 (SP) M age 65 (A) | Average of all MS Donors | SEM |
|---|---|---|---|---|---|
| IL-10 AV CDR2 Frequency | 11891 | 7904 | 4025* | 7940 | 2781 |
| IL-10 BV CDR2 Frequency | 28867 | 22183 | 2484 | 17845† | 9699 |
| Total IL-10 (AV + BV) CDR2 Frequency | 40758 | 30087 | 6509 | 25785 | 12392 |
| IFN-γ AV CDR2 Frequency | 1349 | 1296 | 12* | 886 | 535 |
| IFN-γ BV CDR2 Frequency | 853 | 1993 | 260 | 1035 | 623 |
| Total IFN-γ (AV + BV) CDR2 Frequency | 2203 | 3289 | 272 | 1921 | 1081 |
| Total (AV + BV) Frequency | 42961 | 33376 | 6781 | 27706† | 13254 |

RR, relapsing remitting MS; *Symptomatic; SP, secondary progressive MS. (A) = Avonex.
*Normalized from partial screen of 15 AV peptides.
†Significantly ($p \leq 0.05$) reduced in MS patients versus HC.

The total frequencies of TCR-reactive T cells, calculated by summing the individual frequencies, showed only a two-fold range of responses among the 5 HC donors. These data suggest that on average, as much as 8% of total circulating T cells (78,484 cells/million PBMC) were responsive to TCR CDR2 sequences (Table 5), although this figure is probably somewhat inflated when one considers cross-reactivity among TCR peptides, and T cell clones that secrete both IL-10 and IFN-γ in response to a single peptide. If indeed these TCR reactive T cells possess Treg activity, CDR2-reactive T cells would represent a substantial portion of the CD4+CD25+ Treg population in healthy controls that has been estimated to be between 5 and 10% of T cells.

Example 3

Deficient TCR-Reactive T Cells in MS Patients

Figure 3:
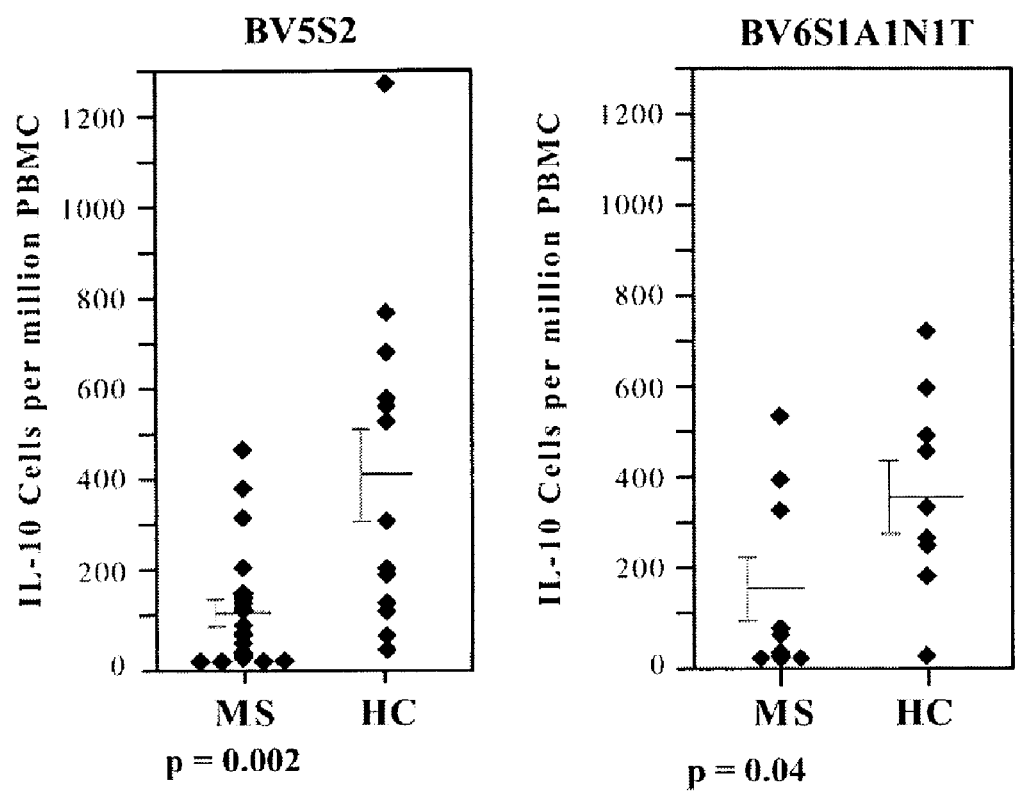
FIG. 3 is a scattergram of the frequency of IL-10 secreting cells in response to TCR peptides. The frequencies are shown for BV5S2 and BV6S1A1N1T specific T cells (background subtracted) for MS patients and healthy controls (HC). Bars in each column represent mean±SEM for each group. Note significantly reduced frequencies in MS patients.
Figure 4A:
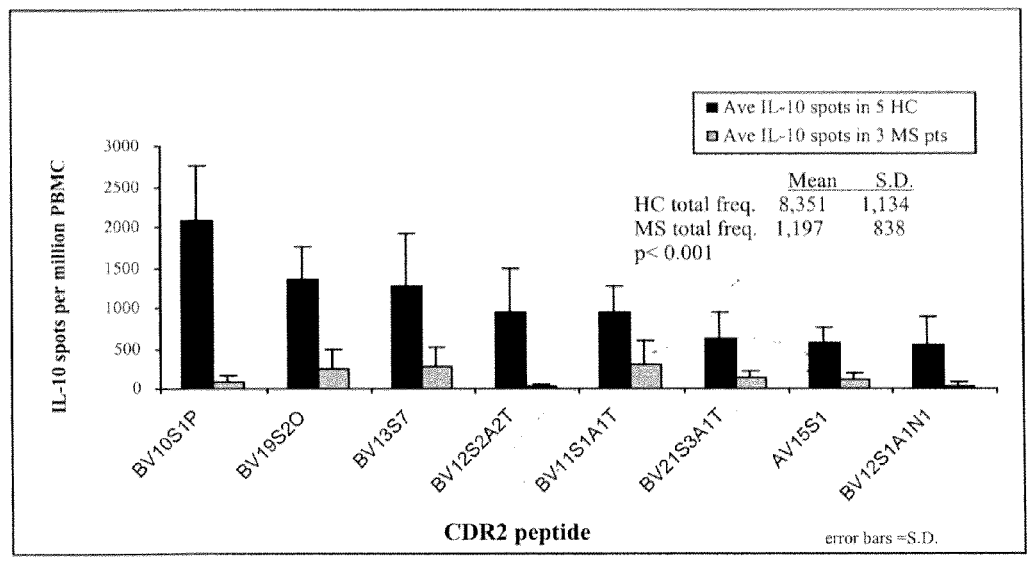
FIG. 4A is a bar graph showing the average IL-10 responses in healthy controls compared to MS patients. The peptides were recognized significantly better ($p<0.05$) by HC than MS patients.

It has been demonstrated that the frequencies of IL-10-secreting PBMC specific for CDR2 peptides from BV5S2 and BV6S1 were significantly lower in MS patients versus HC (FIG. 3). This analysis was expanded to the nearly complete panel of 113 AV and BV CDR2 peptides in 3 MS patients for comparison with the 5 HC presented above (FIGS. 1 and 2). The results show striking differences in both the magnitude and pattern of response in the MS patients versus healthy controls (HC). Note that the reduction in IL-10 responses to BV5 S2 and BV6S1 peptides shown previously (FIG. 3) was again evident in the expanded analysis (FIG. 1). Overall, the total frequency of T cells responding to the panel of CDR2 peptides was significantly reduced (p=0.03) by 65% compared to HC (27,706 cells/million in MS versus 78,484 cells/million in HC, Tables 1 and 2). This reduction was especially marked (>90%) in the frequencies of IFN-γ-secreting T cells in all three MS patients, but was also evident in IL-10-secreting T cells (>50% decrease versus HC), with a significant reduction (p=0.045) in response to BV peptides (17,845 cells/million in MS versus 38,595 cells/million in HC). Moreover, the pattern of response was clearly different in MS patients, showing overall reduced frequencies to most peptides (one example is shown in FIG. 4A). However, for a few peptides, the MS patients responded better than HC.

Figure 4B:
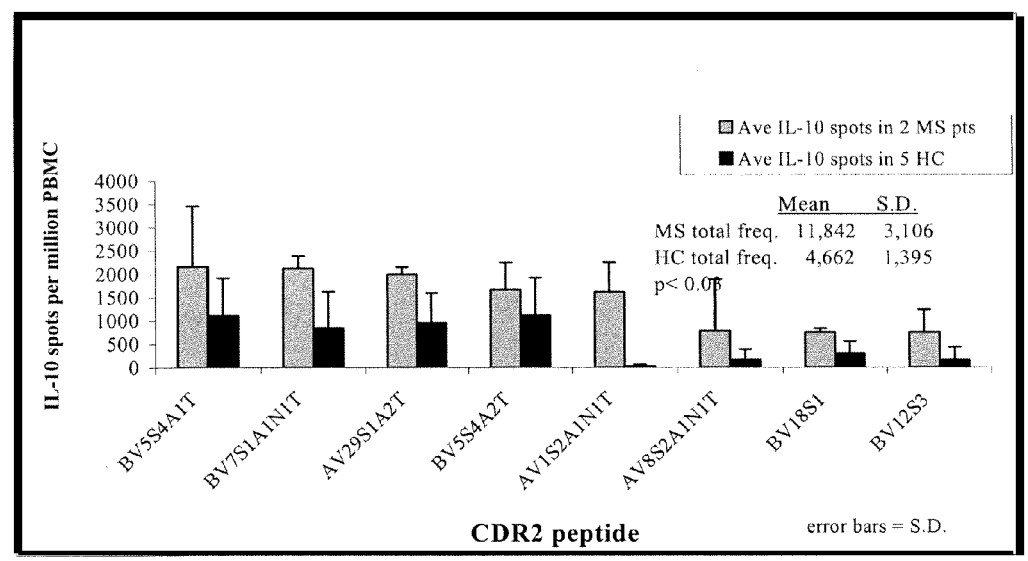
FIG. 4B is a bar graph showing the average IL-10 responses in symptomatic RRMS patients compared to healthy controls. These data identify discriminatory peptides that differ between healthy controls (HC) and MS patients. The peptides were recognized better by two symptomatic RRMS patients than HC. Note significant difference in group means for each comparison. A third SPMS patient responded better than HC to BV25S1A1T and AV1S2A1N1T peptides only.

For example, the two symptomatic RRMS patients, MS193 and MS74, were very reactive to AV1S2A1N1T (>1700 cells/million), whereas there was essentially no response in HC (<25 cells/million) (FIG. 4B). In combination, this group of eight peptides was recognized significantly better by these two MS patients than HC (p<0.03, FIG. 4B). The third SPMS patient (MS186), although having an overall response of only 6% versus HC, nonetheless had an increased response to BV25S1A1T (450 cells/million versus 150 cells/million in HC) and AV1S2A1N1T (300 cells/million versus <25 cells/million in HC, not shown). The AV29S1A2T peptide was highly reactive in MS patients (>1500 cells/million) and HC (about 1000 cells/million) (FIG. 2), as were the BV5S4A1T and BV5S4A2T alleles (>1000 cells/million in both MS patients and HC) (FIG. 1) that likely were cross-reactive (only an F for L difference at residue 8). Surprisingly, however, the MS patients responded poorly to the pseudogene peptides, BV10S1P and BV19S1P (FIG. 1). Taken together, these unique data demonstrate a broad deficiency of TCR reactive T cells, particularly those secreting IFN-γ, with a more profound deficit in the SPMS patient. Remarkably, there were strong perturbations in IL-10 responses to selected TCR peptides, especially in the symptomatic RRMS patients. These perturbations conceivably could reflect natural T-T interactions that occurred subsequent to the activation of a subset of pathogenic T cells that induced the relapses (e.g. BV5S4, BV7S1 and AV1 S2). It will now be of utmost importance to determine if elevated IL-10 responses to these peptides persist and ultimately limit the pathogenic response to bring about a state of remission. One might pre-suppose that vaccination with selected TCR peptides could amplify deficient TCR responses prior to relapses and thereby prevent or reduce activation of pathogenic T cells. If Treg activity is mediated in part by TCR-reactive T cells, as stated in our hypothesis, then specific activation with TCR peptides may result in a broad non-specific regulation of Th1 effector cells through cell-cell contact or by secretion of soluble inhibitory factors.

Example 4

Identification of a Subset of Discriminatory TCR Peptides that Reflect Deficient Anti-TCR Responses in MS Patients Versus HC To facilitate evaluations of additional MS patients and control donors, a subset of TCR peptides was identified that optimally discerned differences in IL-10 responses between HC and MS patients. Seven BV peptides and 1 AV peptide were found that individually were recognized significantly better by all of the HC than the MS patients (FIG. 4A). Further comparison revealed a total frequency of 8,351±1,134 IL-10 secreting T cells/million PBMC in the 5 HC versus 1,197±838 in MS patients. This difference was highly significant (p<0.001) and discriminating (a net difference of 7154 cells/million PBMC), even though the sampling of patients was very small. Thus, it is clear that use of the peptide subset both reflected and enhanced our ability to detect the general deficiency in TCR-reactive IL-10 secreting T cells in MS initially detected by the complete set of CDR2 peptides (p<0.001 for subset versus p=0.03 for complete set of peptides comparing total HC versus MS IL-10 frequencies). The limit of 1.96 standard deviations below the mean of the HC values, 6083 cells/million PBMC, represents the 95% confidence interval, below which responses can be identified that are significantly deficient in future patients tested individually with the peptide subset.

Using a similar approach for analyzing IFN-γ responses to TCR peptides, only 2 BV peptides (BV12S2A1T and BV12S2A2T) and one AV peptide (ADV6S1A1N1) were found that induced IFN-γ-secreting T cells in all 5 HC but that were poorly recognized by MS patients. The two BV12S2 alleles were also quite similar to each other, with only one difference in sequence in CDR2 (A1=Q; A2=K at position 16), but they produced distinct responses in individual donors). Although differences in recognition of each individual IFN-γ-inducing peptide were not significant in HC versus MS donors, the difference in the total frequency (994±528 in HC versus 13±21 in MS) was significant (=0.021) and discriminating (a net difference of 981 cells/million). However, because of the large variation in response among HC, a lower limit to detect deficient responses was not established.

Example 5

TCR-Reactive T Cells Possess Treg Activity

Figure 5A:
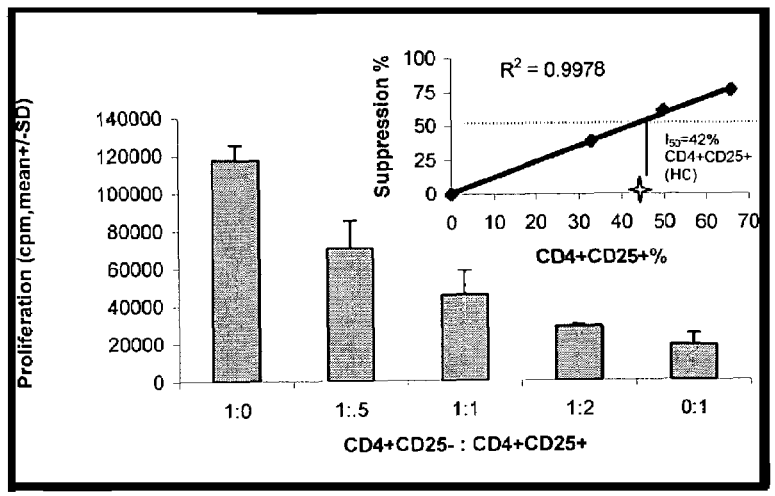
FIG. 5A is a bar graph of Treg activity from CD4+CD25+ T cells freshly sorted from the blood of a healthy control and mixed at the indicated ratios with autologous sorted CD4+CD25− T cells. These cells were stimulated with plate-bound anti-CD3/anti-CD28 mAb for 72 hours and assessed for proliferation. $I_{50}$ value (42%=0.72 ratio of CD4+CD25+ T cells:CD4+CD25− T cells) represents the percentage of CD4+CD25+ Treg cells that induced 50% suppression of CD4+CD25− T cell response. Note that the CD4+CD25+ T cells alone (0:1 ratio) had very low proliferation to stimulation, but induced a dose-dependent inhibition of CD4+CD25 − T cells.
Figure 5B:
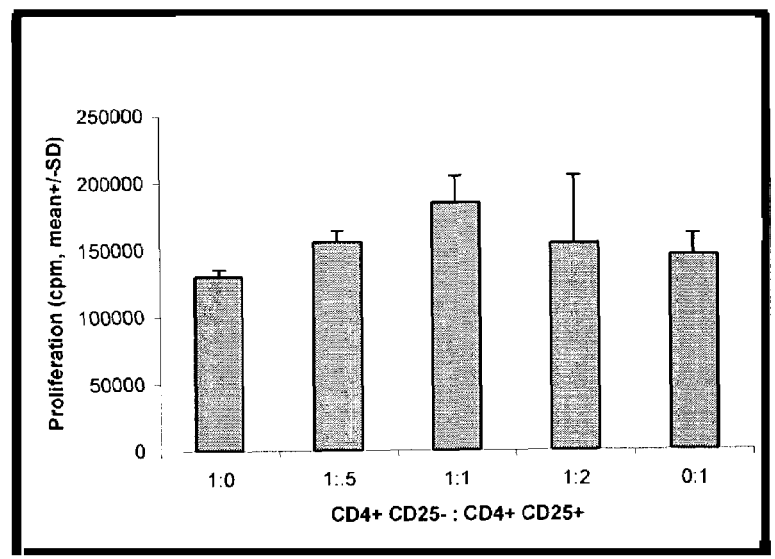
FIG. 5B is a bar graph of Treg activity from the same assay carried out on sorted T cell populations from an MS patient. Note full response of CD4+CD25+ T cells alone to stimulation, and complete lack of inhibition of CD4+CD25− T cells at all cell mixtures ($I_{50}$ could not be determined).
Figure 5C:
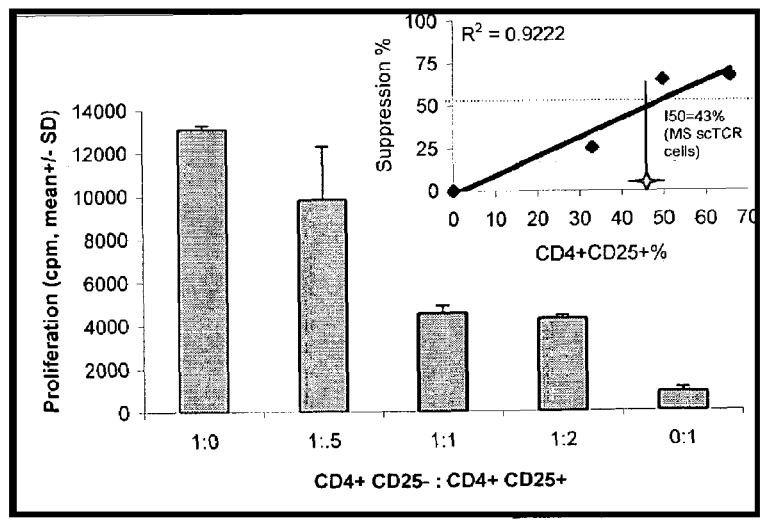
FIG. 5C is a bar graph of Treg activity from the same assay carried out using a CD4+CD25+ T cell line specific for single chain (AV23:BV6S1) TCR molecule from an MS donor previously vaccinated with TCR peptides to inhibit autologous CD4+CD25− cells. Note low response of the line to stimulation and a dose-dependent inhibition ($I_{50}$=43%=0.75 ratio) of autologous CD4+CD25− indicator cells, similar to panel 5A.

A standard procedure was recently developed for assessing inhibitory activity of CD4+CD25+ Treg cells in vitro. This assay involves separation of CD4+ T cells from PBMC using magnetic beads (giving >95% purity), and further separation of CD25+ versus CD25− T cells from the purified CD4+ T cells, giving >90% purity of the CD25+ T cells and >98% purity of the CD25− T cells. These cell populations are cultured alone or are mixed at varying ratios using a constant number of CD4+CD25− responder T cells, and stimulated with plate-bound anti-CD3+anti-CD28 mAbs for 3 days, and are then assessed for proliferation responses using $^3$H-Tdy uptake. Consistent with previous studies in healthy controls, the CD4+CD25− T cells alone gave a robust response to stimulation, whereas the CD4+CD25+ T cells alone had a drastically reduced response to stimulation (FIG. 5A). Moreover, there was a dose-dependent inhibition of the response of CD4+CD25− responder cells in the presence of increasing percentages of CD4+CD25+ Treg cells. By plotting the percent CD4+CD25+ cells versus the percent inhibition, the $I_{50}$ value (% CD4+CD25+ Treg cells giving 50% inhibition of CD4+CD25− indicator cells) was calculated for one HC as 42% (FIG. 5A). The mean $I_{50}$ for 3 HC was 49±11%. Using the same protocol, it was found that CD4+CD25+ T cells from an MS patient not only responded fully to stimulation with anti-CD3+anti-CD28 mAbs (unlike CD4+CD25+ T cells from HC, which were unresponsive), but also were unable to inhibit responses of CD4+CD25− T cells (FIG. 5B). Although many more patients need to be evaluated, these results are the first to indicate that an MS patient lacks detectable Treg activity, in support of our hypothesis.

Having worked out the assay for Treg activity, the inhibitory activity of a TCR-reactive T cell line specific for a recombinant single chain AV23/BV6S1 TCR molecule (7× stimulation over background) was then evaluated. This CD4+CD25+ TCR-reactive T cell line had a low response to anti-CD3/CD28 stimulation and suppressed autologous CD4+CD25− responder cells in a dose-dependent manner ($I_{50}$=43% TCR-reactive T cells, FIG. 5C). These results clearly establish that TCR-reactive T cells possess Treg activity comparable to that found in CD4+CD25+ T cells from PBMC. Although additional experiments are needed, this is a key finding demonstrating that TCR-reactive T cells define a subset of Treg cells. It is noteworthy that the TCR-reactive T cell lines could be selected and expanded in IL-2, but in the Treg assay, these same cells failed to proliferate when stimulated with anti-CD3/CD28 mAbs, as reported for freshly isolated Treg cells. Without being bound by theory, this observation supports the idea that Treg cells can proliferate and expand in vivo to self antigens (i.e. TCR determinants), but attain inhibitory activity at some stage of maturation that precludes continued proliferation.

Example 6

Ongoing TCR Vaccination Study in MS

A new trial was initiated to evaluate immunological, clinical, and MRI changes in MS patients over a period of 6 months during vaccination with a cocktail of three TCR CDR2 peptides, (Y49T)BV5S2, BV6S5, and BV13 μl, corresponding to TCR V genes predominantly expressed by MBP-specific T cells. Overall, a total of 60 relapsing and secondary progressive MS patients were enrolled, and of these, 25 receive 4 weekly injections followed by 5 monthly injections of the cocktail i.d. in buffer, 25 receive 6 monthly injections of the peptide cocktail in Incomplete Freund's adjuvant (IFA), an oil-in-water emulsion that boosts antigenicity, and 10 receive 6 monthly injections of IFA alone.

Figure 6:
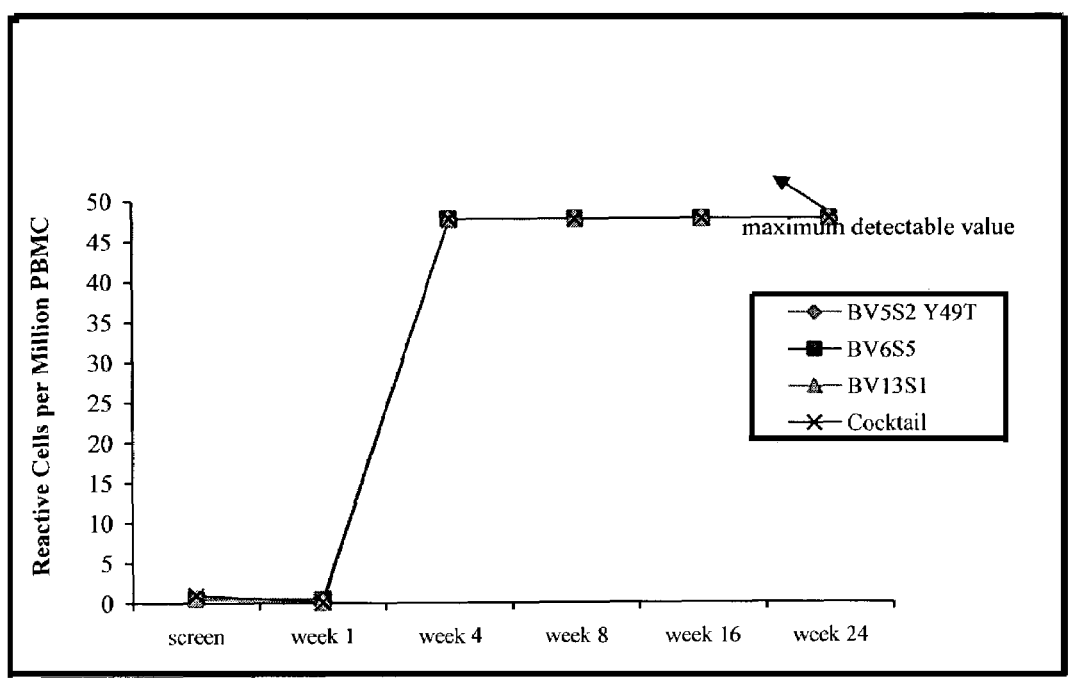
FIG. 6 is a graph demonstrating that peptide vaccination increases frequency of TCR Reactive T cells. Anti-TCR responses of an MS patient to monthly injections of a cocktail of the 3 indicated BV CDR2 peptides are shown. Response was assessed using the limiting dilution assay to determine the frequency of proliferating peptide-specific T cells for each individual peptide and for the cocktail. Note maximal response (frequency>47 cells/million PBMC) to all peptides beginning 4 weeks after the first injection of peptide cocktail that persisted through week 24 (four weeks after the last injection).

Analysis of proliferation and cytokine T cell frequencies of 20 of these patients revealed a robust T cell response to vaccination in approximately 60% of the patients (see FIG. 6). ELISPOT evaluations of IL-10 and IFN-γ frequencies in response to the full panel of 113 CDR2 peptides are performed, as well as an assay of Treg activity prior to vaccination in an additional 30 patients to provide a baseline for comparison with a post-vaccination evaluation.

There is considerable evidence to indicate that T cell recognition of TCR determinants represents a powerful innate regulatory network that can inhibit activation of inflammatory T cells. The nature and outcome of such T-T interactions has been difficult to study in humans, due to the complexity and number of V gene sequences, and the difficulty in defining precise TCR determinants. As disclosed herein, TCR determinants from most of the known CDR2 are unusually immunogenic, triggering release of IL-10 and/or IFN-γ by T cells from healthy donors. However, these same TCR peptides produced very different patterns of responses in some MS patients, and their recognition was drastically reduced in others, suggesting a general inability to regulate Th1 cells expressing the cognate V genes. Interestingly, vaccination with TCR peptides boosts anti-TCR T cell responses in a subset of patients, resulting in reduced responses to neuroantigens and often stabilization or reversal of clinical deficits. Without being bound by theory, TCR reactive T cells define a subset of Treg cells that are deficient in MS patients. This is supported by data showing robust TCR-reactive T cells and Treg activity in HC, but greatly reduced TCR-reactivity and lack of Treg activity in the first MS patients tested.

Example 7

Unmasking of TCR Vaccination Trial

As described above, the ability of a cocktail of 3 TCR peptides (CDR2 sequences from BV5S2, BV6S5, and BV13S1) to induce proliferation and cytokine responses has been tested. The peptide cocktail is injected either in incomplete Freund's adjuvant (IFA) or saline, and another group of patients received saline/IFA alone. Based on the very robust T cell frequencies observed in a number of MS patients, the trial was unblinded to determine if responses fell into one or the other peptide treatment group. Among the 21 patients evaluated, 0/4 receiving saline/IFA alone, 1/8 receiving peptide/saline, but 9/9 receiving peptide/IFA had robust and highly significant responses to one or more peptides in the cocktail ($p<0.001$).

These results demonstrated that the peptides in IFA were much more immunogenic than in saline, and allowed additional experiments to be designed to evaluate additional immunological parameters. Thus, in one embodiment, peptides in IFA are administered to a subject of interest to provide the maximum immunization.

In addition, it was found that TCR-specific T cell lines selected from patients successfully vaccinated with our peptide cocktail have potent Treg activity, and that one patient with a strong TCR response by LDA also began to show Treg activity in PBMC (see below).

Example 8

Treg Activity in PBMC and TCR-Specific T Cell Lines from MS Patients

Figure 7A:
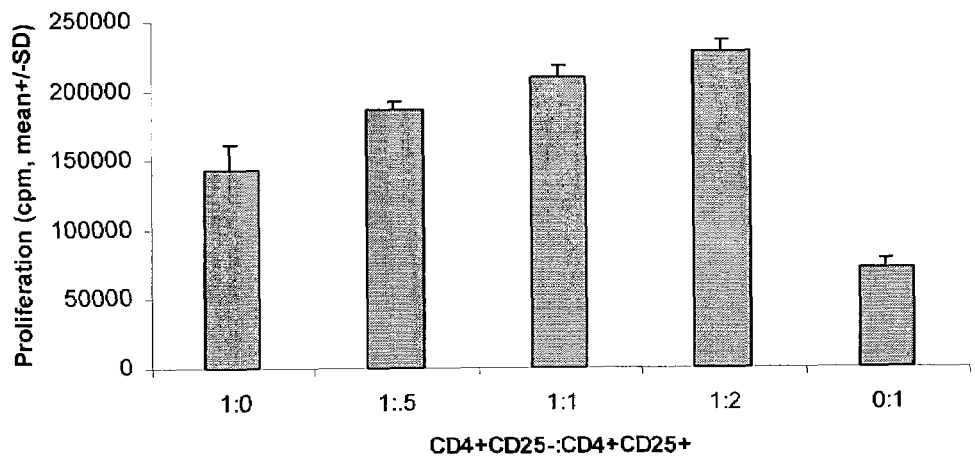
FIG. 7A is a bar graph of MS-102 (IFA) PBMC Treg assay ($I_{50}$ not calculatable).

Data is described above from one MS patient who completely lacked Treg activity in PBMC, from one HC who had strong Treg activity, and from a T cell line specific for a single chain TCR (AV23/BV6) that also had strong Treg activity. Treg activity was also analyzed in two additional MS patients from a clinical trial. Patient MS-102 received saline/IFA alone (no peptide), and as expected had no proliferation activity in response to any of the 3 peptides in the vaccine (CDR2 peptides from BV5S2, BV6S5, and BV13S1). At the end of the study, Treg assay was performed (FIG. 7A). This assay demonstrated that the CD4+CD25+ subfraction not only responded strongly to stimulation with anti-CD3/CD28 (unlike HC donors whose CD4+CD25+ Treg cells had low proliferation response to anti-CD3/CD28), but also completely failed to inhibit the activation of the CD4+CD25− indicator cells.

Figure 7B:
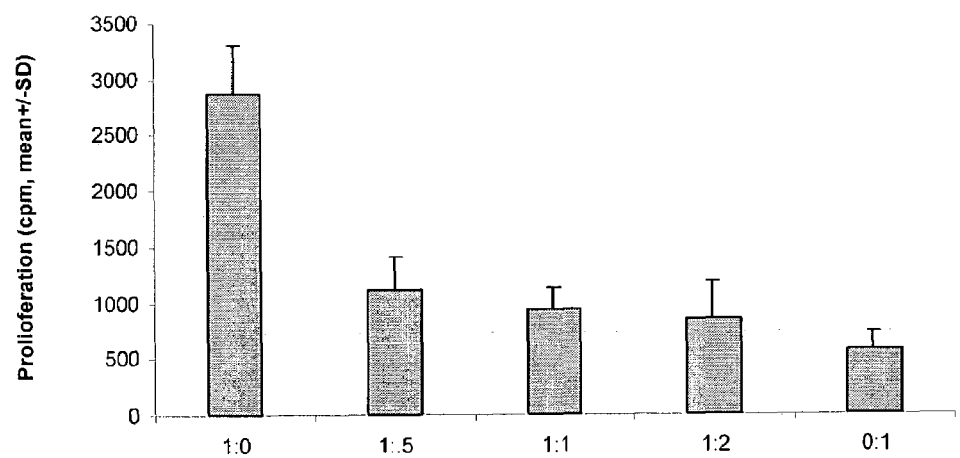
FIG. 7B is a bar graph of MS-111 (peptide/IFA) peptide specific CD4+CD25+ T cell line Treg assay.

A second patient, MS-111, was selected who had maximal LDA responses to vaccination (see FIG. 6). At the end of the 24 week trial, a T cell line was selected that was specific for the cocktail of 3 injected peptides. This T cell line had superior inhibitory properties, producing 50% inhibition in vitro at a ratio of 1:40 Treg cells:CD4+CD25− indicator cells ($I_{50}$=0.024, FIG. 7B). In comparison, PBMC from HC typically produce 50% inhibition at about a 1:1 ratio, ranging from 40-60% Treg cells in the mixed culture (the mean $I_{50}$ for 3 HC=49±11=1:1.04 ratio). For example, Treg activity in PBMC from a healthy control (see FIG. 5A) had an $I_{50}$=42%=1:1.38 ratio of Treg cells to CD4+CD25− indicator cells, and a T cell line specific for scTCR produced about the same level of Treg activity ($I_{50}$=43%=1:1.32 ratio, FIG. 5C). In contrast, a Th 1 T cell line selected against Tetanus toxoid antigen did not have any detectable Treg activity.

This data (FIG. 7B) is a demonstration that T cells specific for CDR2 peptides possess Treg activity. Interestingly, Treg activity assessed in PBMC from Patient MS-111 at exit from the trial (at the same time the T cell line was selected) was nearly within the normal range ($I_{50}$=77%=3.3:1 ratio of Treg:, FIG. 7C), indicating that successful TCR peptide vaccination is associated with Treg activity in vivo.

Example 9

Selection of TCR Peptide-Specific T Cell Lines from HC Donors

As described above, two different pools of peptides were identified of use for discriminating either IL-10 (see FIG. 4A) or IFN-γ responses (see above) between HC and MS patients. Furthermore, a pool of peptides were identified to induce proliferation responses in both HC and MS patients, which can be used to select T cell lines in order to evaluate Treg activity from un-vaccinated donors. These 3 pools of peptides were tested for their ability to induce proliferative responses in an HC donor (FIG. 8). As is shown in the FIG. 8, all 3 pools produced significant proliferation responses in early T cell lines from HC-27. These data confirm the ability of the peptide pools to stimulate TCR-reactive T cells in un-vaccinated donors. CD4+CD25+ T cells from the T cell line selected against Pool #1 from an HC had Treg activity ($I_{50}$=3.4 ratio), demonstrating that TCR reactive T cells from HC also possess inhibitory properties.

Example 10

Determination if TCR Reactive T Cells Define a Subset of CD4+CD25+ Treg Cells

Treg activity induced by response to TCR determinants is tested in CD4+CD25+ and CD4+CD45RO+ versus other T cell subpopulations. Cytokines involved and requirement for cell-cell contact for suppression are evaluated.

CD4+CD25+ can be separated from CD4+CD25− T cells from the blood of HC using magnetic beads. These two populations are tested for response to the discriminatory subset of eight IL-10-inducing and 3 IFN-γ-inducing peptides identified above. As shown in FIG. 5, CD4+CD25+ T cells obtained using magnetic beads possess strong inhibitory activity when mixed with CD4+CD25− T cells and then stimulated with anti-CD3/CD28 mAbs.

Because of the relatively large number of cells needed, buffy coats are used. Each buffy coat contains cells from about 550 ml blood, yields about 800 million PBMC, of which 40% (320 million) are CD4+ T cells, and about 5% of these (15-20 million) are CD4+CD25+ T cells, with the remaining CD4+ T cells (about 300 million) being CD4+CD25−. For each experiment, the CD4+CD25+ T cells are tested for inhibitory Treg activity against anti-CD3/CD28 mAb stimulated CD4+CD25– T cells. This assay requires about 2 million CD4+CD25+ T cells from each donor. For each TCR peptide to be tested, three replicate wells containing 250,000 separated T cells are set up, in addition to 50,000 T cell depleted APCs (using anti-CD3-coated beads) in ELISPOT plates for assessment of IL-10 or IFN-γ-secreting T cells. For each cytokine to be tested, six wells receiving no peptide as a negative control are also included, and three wells receiving anti-CD3 mAb as a positive control. Thus, for each cytokine, 24 wells (6 million CD4+CD25+ and 6 million CD4+CD25– T cells) are needed. A parallel assay is carried out using unseparated cells to determine what level of Treg reactivity is present initially. A similar approach is used to separate CD4+CD45RO+ versus CD4+CD45RO– T cells prior to ELISPOT testing for response to the selected panel of highly reactive TCR peptides to determine if TCR reactive T cells reside mainly in the naive (CD45RO–) or memory (CD45RO+) populations.

Example 11

Determination if MS Patients with Deficient TCR Reactivity also have Deficient Treg Activity As disclosed herein, strikingly altered or deficient IL-10 responses to TCR peptides were found with a significantly reduced frequency of TCR-reactive IFN-γ-producing T cells in all 3 MS patients tested. Currently, it is unknown if MS patients with deficient TCR-reactivity also have reduced Treg activity, but this is expected if TCR-reactive T cells constitute a significant portion of the Treg cells. Thus, both TCR and Treg activity in MS patients and HC from the same sampling of blood is compared directly.

For TCR recognition, IL-10 and IFN-γ ELISPOT assays using the subset of 8 discriminatory IL-10-inducing peptides identified above (FIG. 4A) and 3 IFN-γ-inducing peptides (ADV6S1A1N1, BV12S2A1T and BV12S2A2T) is carried out that optimally reflect deficient responses in MS patients. The assay utilizes triplicate cultures of 250,000 PBMC/well for each peptide and negative (medium) and positive (ConA) controls (about 18 million PBMC). Responses are quantified by determining the frequency of TCR reactive T cells above background for each peptide. For each HC or MS donor, the total IL-10 and IFN-γ frequencies are determined separately and compared for the two groups. Total IL-10 frequencies <6083 cells/million for the subset of peptides is considered a significantly reduced response, as determined above.

For the Treg assay, CD4+CD25+ and CD4+CD25– T cells are separated from 100 ml blood and each subpopulation is stimulated with anti-CD3+anti-CD28 mAbs alone or in mixed cultures containing a fixed number (10,000) of CD4+ CD25– responder cells and varying numbers of CD4+CD25+ T cells to give 0%, 20%, 33%, 50%, 67% and 100% in triplicate cultures (see FIG. 5). After 3 days, the cells are harvested and assessed for proliferation and cytokine production (IFN-γ and IL-13) in culture supernatants by ELISA. The endpoint of each Treg assay is to verify a dose-dependent inhibition of Th1 function and to calculate the percentage of CD4+CD25+ T cells that produces 50% inhibition ($I_{50}$) of each parameter (see FIG. 5).

As disclosed herein, Treg activity was demonstrated in 3 HC that was lacking in one MS patient. Thus, simultaneous TCR and Treg assays on ten RRMS patients (not on disease modifying agents) and ten age and gender matched HC are carried out. MS patients have decreased ELISPOT responses to the set of discriminatory peptides selected, and it is determined if this decreased TCR response correlates with decreased Treg activity compared to HC.

It is necessary to test only a subset of the CDR2 peptides for this comparison in order to use available numbers of PBMC. Practically, blood donations are limited to about 120 ml, and the small percentage of CD4+CD25+ T cells in blood requires at least 100 ml of blood for the Treg assay, leaving only about 20 ml for the ELISPOT assay. Although the MS patients may react strongly to a few different peptides that are not tested, the subset used is generally representative of peptides that are recognized differently by MS versus HC, and taken together, these peptides should detect and quantify deficient TCR reactivity.

Example 12

Evaluation of Treg Activity in Subjects with Multiple Sclerosis

An evaluation of Treg responses in a total of 33 MS patients and 26 healthy control (HC) donors was carried out. For this study, blood was obtained by venipuncture from twenty-six HC donors (9 males and 17 females) and 33 MS patients (12 males and 21 females) after obtaining informed consent. The HC subjects had a mean age of 34 years (range, 22 to 60 years), and the MS patients had a mean age of 39 years (range, 20 to 61 years).

Blood was collected into heparinized tubes and mononuclear cells separated by Ficoll density centrifugation. The indicator (CD4+CD25–) and suppressor (CD4+CD25+) cells were isolated from 100 million PBMC. These cells were first incubated for 45 minutes at 4° C. with anti-CD8, anti-CD19, anti-CD56, and anti-CD11b mAbs (Caltag, Burlingame, Calif.), at the following concentration: (# of PBMC×percent of CD8+ T cells, B cells, NK cells and Macrophages×4 ul). After washing twice the cells were incubated for another 45 minutes with 400 ul of magnetic beads (Dynal, Oslo, Norway) at 4° C. After placing on the magnet for two minutes, the negatively selected CD4+ T cells were collected and 25 ul of anti-CD25 mAb (Caltag, Burlingame, Calif.) was added. After a 45 minute incubation at 4° C. the cells were washed and 50 ul of magnetic beads added and incubated at 4° C. for another 45 minutes. The CD4+CD25– fraction was collected by placing the tube on the magnet and removing the supernatant. The CD4+CD25+ T cell fraction was removed from the magnetic beads by vortexing for two minutes and then placing the tube back on the magnet. A similar procedure was used for sorting CD45RO+ versus CD45RO– T cells from the CD4+CD25– fraction obtained above, using anti-CD45RO mAb (Caltag).

Suppression assays were performed in 96-well round bottom plates (Becton Dickinson, Franklin Lakes, N.J.) in a final volume of 200 μl/well of 1% type AB human Serum complete media (Biowhittaker, Walkersville, Md.). Prior to assay setup the 96 well plates were incubated with 0.2 μg/well of anti-CD3 and anti-CD28 antibodies (Caltag Labs, Burlingame, Calif.) overnight at 4° C. All wells were washed before assay setup. The CD4+CD25– cells were plated at $2.0 \times 10^4$/well alone or in combination with CD4+CD25+ cells in triplicates at $1.0 \times 10^4$, $2.0 \times 10^4$, and $4.0 \times 10^4$/well. Thus the cells were co-cultured at ratios of: 1:0, 1:0.5, 1:1, 1:2, and 0:1. On day 6, 0.5 μCi of $^3$H-thymidine (NEN, Boston, Mass.) was added to each well for the final 16 hours of culture. The cells were then harvested on glass fiber filters and assessed for uptake of the labeled thymidine by liquid scintillation. Percent suppression was determined at each mixed cell ratio compared to responses of CD4+CD25+ (suppressor cells) and CD4+ CD25− T cells (indicator T cells) alone as follows:

Mean cpm (indicator cells)−mean cpm (mixed cell culture) mean cpm (indicator cells)−mean cpm (suppressor cells)

The percent suppression was plotted versus increasing percentage of suppressor:indicator cells and a regression line was calculated. $I_{50}$ values were determined as the ratio of suppressor:indicator cells that produced 50% suppression. In some instances, the data were presented only for the 1:2 ratio of indicator:suppressor cells.

CD4+CD25+ T cells from younger HC donors were strongly inhibitory at a 1:2 ratio of indicator:regulatory T cells, but the inhibition declined with age. In contrast, CD4+ CD25+ T cells from MS patients of all ages (tested concurrently with HC donors) had reduced or absent inhibitory activity versus autologous CD4+CD25− indicator cells. In total, Treg activity was detected in 12/26 HC donors versus 3/33 MS patients (p<0.002, Fisher's exact test). In donors under the age of 32, Treg responses were detected in 10/16 HC donors versus 1/13 MS patients (p<0.006). Treg activity was not detectable in 5 treatment-naive donors or in 18 of 19 MS patients receiving standard therapies, including IFN-β-1a (Avonex or Rebif), IFN-β-1b (Betaseron), or Glutiramer Acetate (GA). The one moderately suppressive MS patient in this category was receiving Avonex. This lack of suppressive Treg activity in the CD4+CD25+ T cell fraction was consistent upon retesting in four of the non-suppressive MS donors (indicated by error bars in FIG. 9). Additionally, no Treg activity was found in four MS patients from a recent TCR peptide vaccination trial who received placebo (IFA/saline) or a weak formulation of a trivalent TCR peptide vaccine in saline. However, two out of four MS patients from this trial who had been successfully vaccinated with the more potent formulation of the TCR peptide vaccine given in IFA did have detectable suppressive activity (FIG. 9).

To verify that the lack of suppression by MS CD4+CD25+ T cells was not due to the method used to obtain the T cells, FACS-sorted CD4+CD25+$^{hi}$ T cells were also used. These cells are known to possess the greatest suppressive activity, to inhibit FACS-sorted CD4+CD25− indicator cells.

Briefly, PBMCs were isolated from peripheral blood by Ficoll (Amersham Phrmacia Biotech AB, Uppsala, Sweden) density gradient centrifugation. The indicator (CD4+CD25−) and suppressor (CD4+CD25+$^{high\ or\ low}$) cell fractions were isolated from $150 \times 10^6$ PBMC. These cell fractions were sorted using a FACS Vantage (Becton Dickinson Biosciences, San Jose, Calif.). One hundred fifty million PBMCs were incubated with 0.4 ml each anti-CD4 FITC and anti-CD25PE (BD Pharmingen, San Diego, Calif.) for 20 minutes at 4° C. On the forward versus side scatter plot the sort regions were constrained to the lymphocyte population. Sorted cells were collected into serum containing medium, washed, and assessed for Treg activity under the same conditions as for magnetic bead sorted cells.

Figure 10:
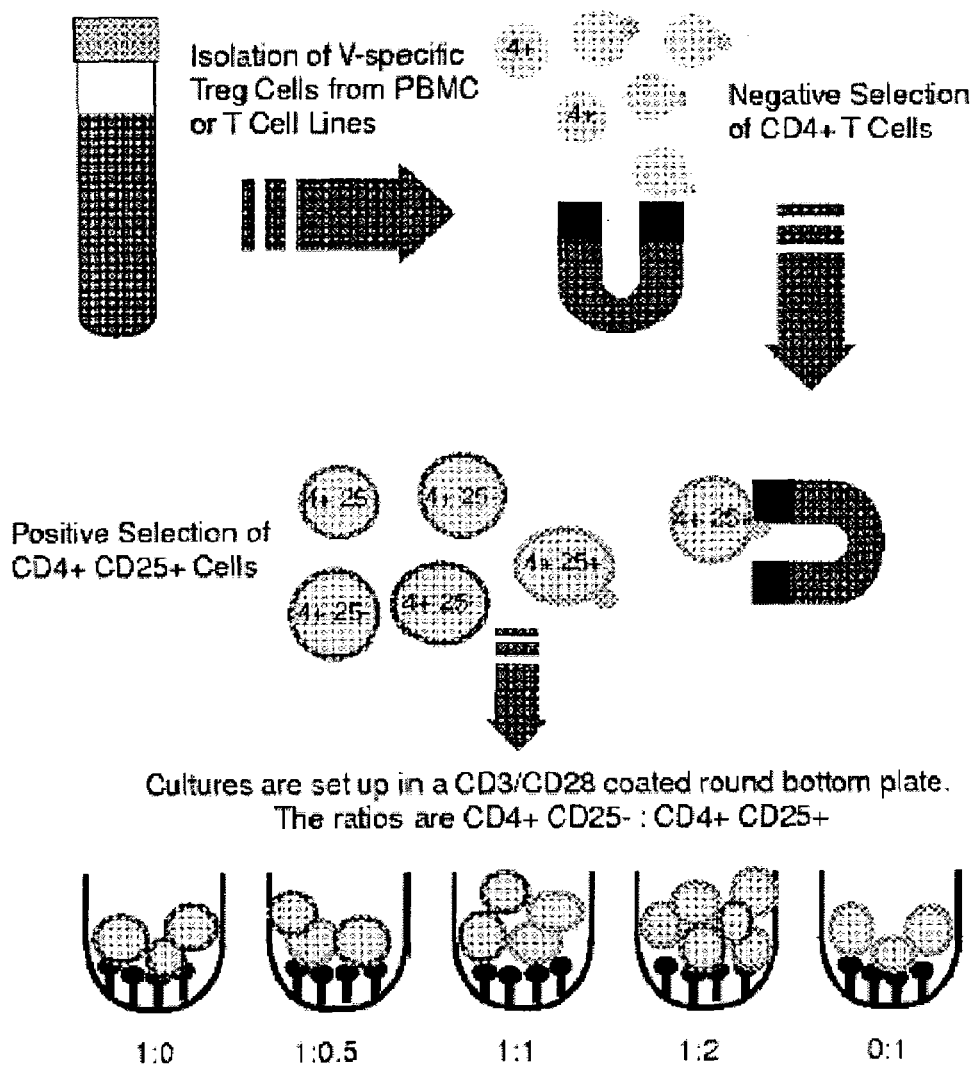
FIG. 10 is a schematic diagram of an assay for Treg activity.

For the Treg suppression assays (see FIG. 10), prior to assay setup, wells from a 96-well round bottom plate were coated with 0.05 ug/well of anti-CD3 overnight at 4° C. All wells were washed before assay setup. The CD4+CD25− cells were plated at $3.0 \times 10^4$ cells/well. While the CD4+ CD25+$^{low\ or\ high}$ cell fractions were plated in triplicates at $1.5 \times 10^4$, $3.0 \times 10^4$, and $6.0 \times 10^4$ cells/well. Thus the cells fractions were co-cultured at ratios of: 1:0, 1:0.5, 1:1, 1:2, and 0:1. Irradiated PBMCs were added to all wells as APC at $3 \times 10^5$/well. Proliferation responses were assessed as described for the bead sorted suppression assay above. MS donors without suppressive activity using magnetic bead sorted cells also did not have detectable suppressive activity using FACS-sorted cells.

Example 13

Treg Activity in T Cell Lines

Figure 11:
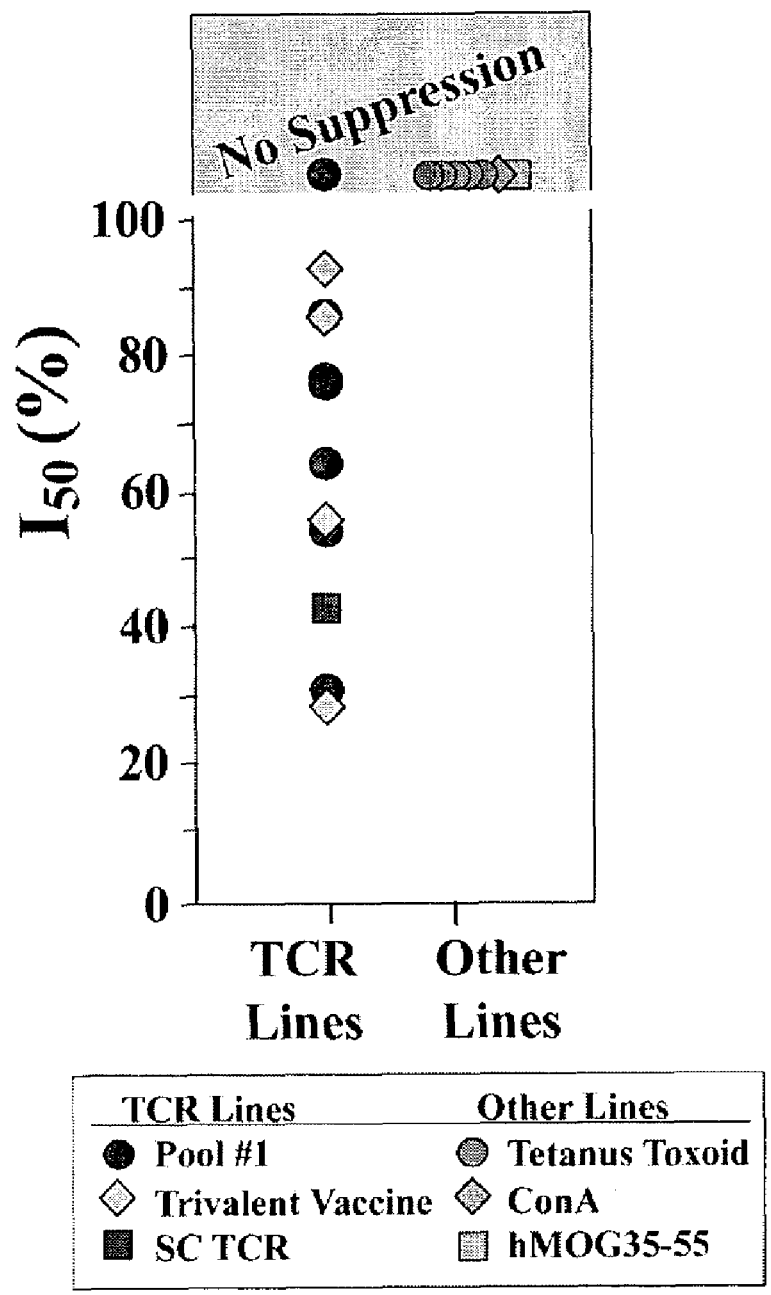
FIG. 11 is a plot showing that Treg activity was detected in 11/12 TCR-reactive T cell lines but in 0/7 T cell lines reactive to non-TCR antigens or ConA ($p<0.001$).

Treg activity was found in CD4+CD25+ T cells from 11 of 12 T cell lines specific for a variety of CDR2 peptides, with $I_{50}$ values ranging from 28% to 92%, whereas no Treg activity was found in 7 T cell lines specific for recall or myelin antigens (FIG. 11). Treg activity observed in the TCR-reactive T cell lines was also cell-cell contact dependent, and reversed completely by addition of IL-2 and antibodies to CTLA-4, GITR, IL-10, and IL-17, but not TGF-β, indicating that the T line cells possessed Treg characteristics identical to PBMC Treg cells. These results establish that CD4+CD25+ TCR-reactive T cells but not other CD4+CD25+ T cells possess Treg activity comparable to that found in CD4+CD25+ T cells from PBMC.

It will be apparent that the precise details of the methods or compositions described may be varied or modified without departing from the spirit of the described invention. We claim all such modifications and variations that fall within the scope and spirit of the claims below.

I claim:

1. A method of identifying a T cell receptor (TCR) variable (V) peptide of interest as being of use as a therapeutic agent in a subject affected with an autoimmune disease, comprising:
    a) contacting T cells from the subject with the autoimmune disease with TCR V beta peptides, TCR V alpha peptides, or both TCR V beta peptides and TCR V alpha peptides in vitro, wherein the TCR V beta peptides and the TCR V alpha peptides comprise a complementarity determining region 2 (CDR2) peptide,
    b) detecting cytokine expression by the T cells, wherein detecting cytokine expression comprises detecting expression of interleukin (IL)-10, to select a TCR V peptide of interest that produces altered expression of IL-10 by the T cells from the subject with the autoimmune disease as compared to T cells from a healthy control subject that does not have the autoimmune disease, wherein altered IL-10 expression is indicated by at least a 50% higher expression of IL-10 by T cells from the subject with the autoimmune disease as compared to expression of IL-10 by T cells from the healthy control subject; and
    c) assessing the regulatory activity of CD4+CD25+ T cells isolated from the subject with the autoimmune disease, wherein the CD4+CD25+ T cells are specifically elicited in response to the TCR V peptide of interest,
    wherein an increase in the regulatory activity of the CD4+CD25+ T cells elicited in response to the TCR V peptide of interest identifies the TCR V peptide of interest as being of use as a therapeutic agent.

2. The method of claim 1, wherein the autoimmune disease is multiple sclerosis, Rheumatoid arthritis, systemic lupus erythematosis, type I diabetes, non-obese diabetes, myasthenia gravis, Grave's disease, Hashimoto's thyroiditis, or psonasis.

3. The method of claim 2, wherein the autoimmune disease is multiple sclerosis.

4. The method of claim 1, wherein the method comprises contacting T cells with TCR V beta peptides.

5. The method of claim 1, wherein the method comprises contacting T cells with TCR V alpha peptides.

6. The method of claim 1, wherein expression of IL-10 is determined by an immunospot assay.

7. The method of claim 1, wherein assessing the regulatory activity of the CD4+CD25+ T cells comprises
    contacting CD4+ T cells with the TCR V peptide of interest to produce regulatory CD4+CD25+ T cells;
    contacting the regulatory CD4+CD25+ T cells with CD4+ CD25− indicator T cells; and
    determining the proliferation of the CD4+CD25− indicator T cells or the release of inflammatory cytokines by the CD4+CD25− indicator cells after stimulation of a T cell receptor on the CD4+CD25− indicator cells.

8. The method of claim 7, wherein the stimulation of the T cell receptor comprises contacting the CD4+CD25− indicator cells with an antibody that specifically binds CD3 and an antibody that specifically binds CD28 or contacting the CD4+ CD25− cells with a specific antigen.

9. The method of claim 7, wherein a decrease in the proliferation of the CD4+CD25− indicator T cells in the presence of the regulatory CD4+CD25+ T cells as compared to the proliferation of the CD4+CD25− indicator cells in the absence of the regulatory CD4+CD25+ T cells indicates that the TCR V peptide elicits regulatory activity.

10. The method of claim 1, wherein the TCR V alpha peptides and the TCR V beta peptides are 15 to 30 amino acids in length.

11. The method of claim 1, wherein the TCR V alpha peptides comprise an individual TCR V alpha peptide consisting of an amino acid sequence set forth as one of SEQ ID NOs: 1-51.

12. The method of claim 1, wherein the TCR V beta peptides comprise an individual TCR V beta peptide consisting of an amino acid sequence set forth as one of SEQ ID NOs: 52-116.

13. A method of identifying a T cell receptor (TCR) variable (V) peptide of interest as being of use as a therapeutic agent in a subject affected with an autoimmune disease, comprising:
    a) contacting T cells from the subject with the autoimmune disease with TCR V beta peptides, TCR V alpha peptides, or both TCR V beta peptides and TCR V alpha peptides, wherein the TCR V beta peptides and the TCR V alpha peptides comprise a complementarity determining region 2 (CDR2) peptide;
    b) detecting interleukin (IL)-10 expression by the T cells to select a TCR V peptide of interest that produces altered expression of interleukin (IL)-10 by the T cells from the subject with the autoimmune disease as compared to T cells from a healthy control subject that does not have the autoimmune disease, wherein altered IL-10 expression is indicated by at least a 50% higher expression of IL-10 by T cells from the subject with the autoimmune disease as compared to expression of IL-10 by T cells from the healthy control subject; and
    c) assessing the regulatory activity of CD4+CD25+ T cells isolated from the subject with the autoimmune disease, wherein the CD4+CD25+ T cells are specifically elicited in response to the TCR V peptide of interest,
    wherein altered IL- 10 expression and an increase in the regulatory activity of the CD4+CD25+ T cells elicited in response to the TCR V peptide of interest identifies the TCR V peptide of interest as being of use as a therapeutic agent.

14. The method of claim 13, wherein assessing the regulatory activity of the CD4+CD25+ T cells comprises contacting CD4+ T cells with the TCR V peptide of interest to produce regulatory CD4+CD25+ T cells;

contacting the regulatory CD4+CD25+ T cells with CD4+CD25− indicator T cells; and determining the proliferation of the CD4+CD25− indicator T cells or the release of inflammatory cytokines by the CD4+CD25− indicator cells after stimulation of a T cell receptor on the CD4+CD25− indicator cells.

* * * * *

UNITED STATES PATENT AND TRADEMARK OFFICE
CERTIFICATE OF CORRECTION

PATENT NO. : 7,462,486 B2
APPLICATION NO. : 10/438729
DATED : December 9, 2008
INVENTOR(S) : Arthur A. Vandenbark It is certified that error appears in the above-identified patent and that said Letters Patent is hereby corrected as shown below:

Title Page; item (56) In Other Publications:

Please insert the following references which were submitted in an Information Disclosure Statement on October 13, 2006, and initialed by the Examiner on December 21, 2006, but were not listed in the patent:

Bebo et al., "Androgens Alter the Cytokine Profile and Reduce Encephalitogenicity of Myelin-reactive T-Cells," *J. Immunol.* 162:35 (1998)

Bebo et al., "Gender Differences in Experimental Autoimmune Encephalomyelitis Develop During the Induction of the Immune response to Encephalitogenic Peptides," *J. Neurosci. Res.* 52:420-429 (1998)

Bourdette et al., "Basic Protein-Specific T-Cell Lines That Induce Experimental Autoimmune Encephalomyelitis in SJL/J Mice: Comparison with Lewis Rat Lines," *Cell Immunol.* 112:351 (1988)

Carlsten et al., "Additive effects of suboptimal doses of estrogen and cortisone on the suppression of T lymphocyte dependent inflammatory responses in mice," *Infamm Res.* 45:26-30 (1996)

Correale et al., "Steroid Hormone Regulations of Cytokine Secretion by Proteolipid Protein-Specific CD4+ T Cells Clones Isolated from Multiple Sclerosis Patients and Normal Control Subjects," *J. Immunol.* 161:3365-3374 (1998)

Dalton et al., "Multiple Defects of Immune Cell Function in Mice with Disrupted Interferon-γ Genes," *Science* 259:1739-1742 (1993)

Signed and Sealed this
Seventh Day of June, 2011

David J. Kappos
*Director of the United States Patent and Trademark Office*

Goverman et al., "Transgenic Mice that Express a Myelin Basic Protein-Specific T Cell Receptor Develop Spontaneous Autoimmunity," Cell 72:551-560 (1993)

Hashim et al., Antibodies Specific for VB8 Receptor Peptide Suppress Experimental Autoimmune Encephalomyelitis," J. Immunol. 144:4621-4627 (1990)

Jansson et al., "Estrogen induces a potent suppression of experimental autoimmune encephalomyelitis and collagen-induced arthritis in mice," Journal of Neuroimmunology 53:203-207 (1994)

Kumar et al., "The Involvement of T Cell Receptor Peptide-specific Regulatory CD4+ T Cells in Recovery from Antigen-induced Autoimmune Disease," J. Exp. Med. 178:909-916 (1993)

Martin et al., "Immunotherapy of multiple sclerosis: Where are we? Where should we go?" Nat. Immunol. 2:785-788 (2001)

Offner et al., "Vaccination with BV8S2 Protein Amplifies TCR-Specific Regulation and Protection Against Experimental Autoimmune Encephalomyelitis in TCR BV8S2 Transgenic Mice," J. Immunol. 161:2178-2186 (1998)

Offner et al., "Estrogen potentiates treatment with T-cell receptor protein of female mice with experimental encephalomyelitis," Journal of Clinical Investigation 105(10):1465-1472 (2000)

Roselli et al., "Sex Differences in Androgen Responsiveness in the Rat Brain: Regional Differences in the Induction of Aromatase Activity," Endocrine 64:139 (1996)

Rovaris et al., The role of non-conventional MR techniques to study multiple sclerosis patients," J. Neurol. Sci. 186 Suppl. 1:S3-9 (2001)

Sicotte et al., "Treatment of Multiple Sclerosis with the Pregnancy Hormone Estriol," Ann. Neurol 52:421-428 (2002)

Steinman et al., "Virtues and pitfalls of EAE for the development of therapies for multiple sclerosis," Trends in Immunology 26:565-571 (2005)

Vaniene et al., "Neonatal Injection of Lewis Rats with Recombinant Vβ8.2 Induces T Cell but not B Cell Tolerance and Increased Severity of Experimental Autoimmune Encephalomyelitis," J. Neurosci. Res. 45:475-486 (1996)

Zipp et al., "Diversity of the anti-T-cell receptor immune response and its implications for T-cell vaccination therapy of multiple sclerosis," Brain 121:1395-1407 (1998)

In the Specification:

Column 10, line 27: "Conservative"" should read --"Conservative"--

Column 10, line 53: "prepare by" should read --prepared by--

Column 18, line 3: "separate" should read --separated--

Column 28, table 5: –53665– has been omitted, and should be added to line 3, column 7

Column 28, table 5: –7502– has been omitted, and should be added to line 3, column 8

Column 31, line 37: "donors)." should read --donors.--

Column 37, lines 3-6: "mean cpm (indicator cells)–mean cpm (mixed cell culture) mean cpm (indicator cells)–mean cpm (suppressor cells)" should appear as:
    --<u>Mean cpm (indicator cells) – mean cpm (mixed cell culture)</u>
    mean cpm (indicator cells) – mean cpm (suppressor cells)--